(12) United States Patent
Lenting et al.

(10) Patent No.: US 11,560,436 B2
(45) Date of Patent: Jan. 24, 2023

(54) ANTI-VWF D'D3 SINGLE-DOMAIN ANTIBODIES FUSE TO CLOTTING FACTORS

(71) Applicants: INSERM (INSTITUT NATIONAL DE LA SANTE ET DE LA RECHERCHE MEDICALE), Paris (FR); UNIVERSITE PARIS-SACLAY, Saint Aubin (FR)

(72) Inventors: Petrus Lenting, Kremlin-Bicetre (FR); Gabriel Ayme, Le Kremlin Bicetre (FR); Cecile Denis, Le Kremlin-Bicetre (FR); Olivier Christophe, Le Kremlin-Bicetre (FR)

(73) Assignees: INSERM (INSTITUT NATIONAL DE LA SANTE ET DE LA RECHERCHE MEDICALE), Paris (FR); UNIVERSITE PARIS-SACLAY, Saint Aubin (FR)

(*) Notice: Subject to any disclaimer, the term of this patent is extended or adjusted under 35 U.S.C. 154(b) by 378 days.

(21) Appl. No.: 16/818,463

(22) Filed: Mar. 13, 2020

(65) Prior Publication Data
US 2020/0207869 A1 Jul. 2, 2020

Related U.S. Application Data

(62) Division of application No. 16/072,784, filed as application No. PCT/EP2017/051569 on Jan. 25, 2017, now Pat. No. 10,626,186.

(30) Foreign Application Priority Data

Jan. 26, 2016 (EP) .................................. 16305071

(51) Int. Cl.
| | | |
|---|---|---|
| C07K 16/36 | (2006.01) | |
| C07K 14/755 | (2006.01) | |
| C07K 14/745 | (2006.01) | |
| A61P 7/04 | (2006.01) | |
| A61K 39/00 | (2006.01) | |
| C12N 15/62 | (2006.01) | |

(52) U.S. Cl.
CPC .............. *C07K 16/36* (2013.01); *A61P 7/04* (2018.01); *C07K 14/745* (2013.01); *C07K 14/755* (2013.01); *C12N 15/62* (2013.01); *A61K 2039/505* (2013.01); *C07K 2317/33* (2013.01); *C07K 2317/565* (2013.01); *C07K 2317/569* (2013.01); *C07K 2317/92* (2013.01); *C07K 2317/94* (2013.01); *C07K 2319/31* (2013.01)

(58) Field of Classification Search
CPC ..... C07K 16/36; C07K 14/745; C07K 14/755
See application file for complete search history.

*Primary Examiner* — Elly-Gerald Stoica
(74) *Attorney, Agent, or Firm* — WC&F IP

(57) ABSTRACT

The invention relates to isolated single-domain antibodies (sdAb) directed against von Willebrand Factor (VWF) D'D3 domain and chimeric polypeptides comprising thereof such as blood clotting factors and their uses in therapy such as in the prevention and treatment of hemostatic disorders. The invention also relates to a method of extending or increasing half-life of a therapeutic polypeptide comprising a step of adding to the polypeptide sequence of said therapeutic polypeptide at least one sdAb directed against VWF D'D3 domain.

Figure 1:
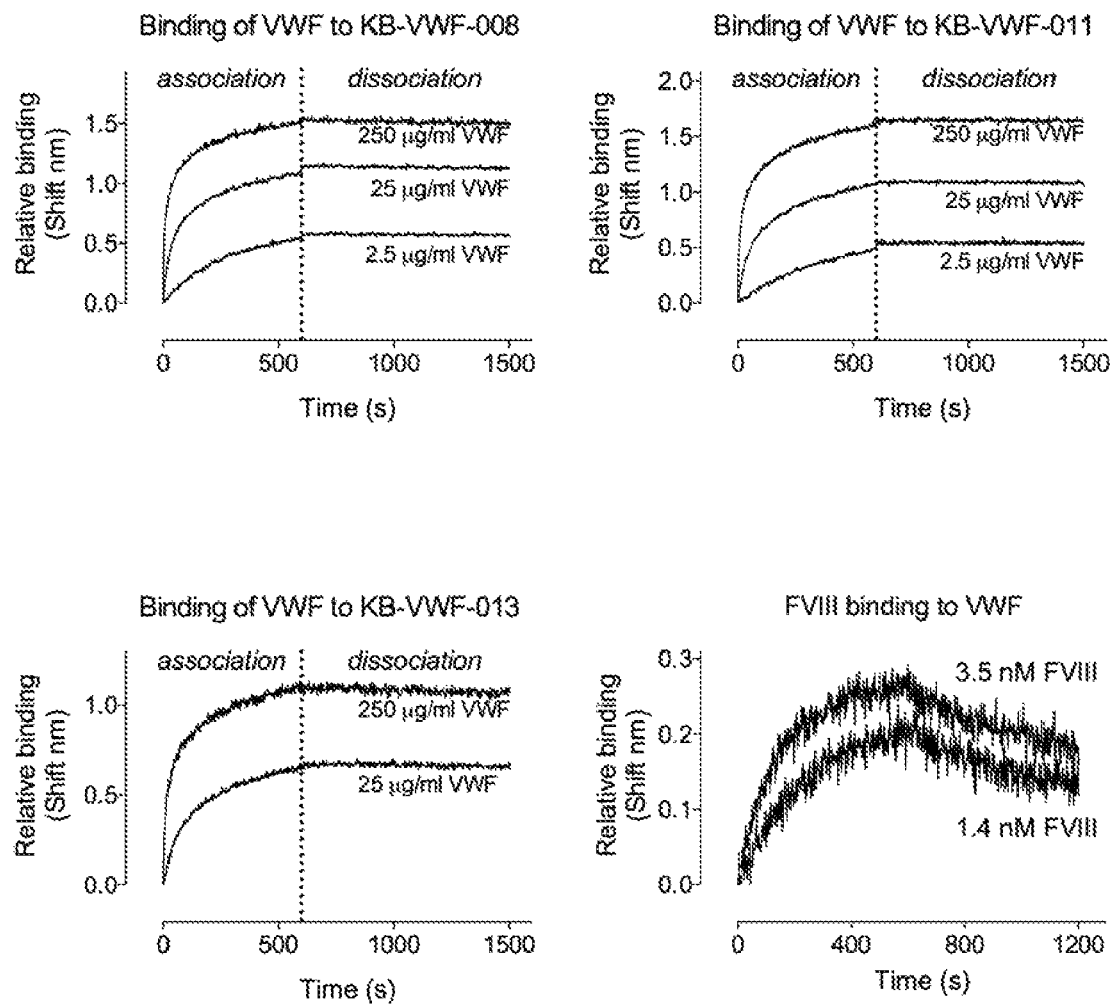

10 Claims, 5 Drawing Sheets
Specification includes a Sequence Listing.

SEQUENCE LISTING

<160> NUMBER OF SEQ ID NOS: 23

<210> SEQ ID NO 1
<211> LENGTH: 9
<212> TYPE: PRT
<213> ORGANISM: Artificial
<220> FEATURE:
<223> OTHER INFORMATION: Synthetic KB-VWF-013 CDR1SEQ ID NO: 1

<400> SEQUENCE: 1

Gly Arg Thr Phe Ile Arg Tyr Ala Met
1               5

<210> SEQ ID NO 2
<211> LENGTH: 16
<212> TYPE: PRT
<213> ORGANISM: Artificial
<220> FEATURE:
<223> OTHER INFORMATION: Synthetic KB-VWF-013 CDR2 SEQ ID NO: 2

<400> SEQUENCE: 2

Ile Pro Gln Ser Gly Gly Arg Ser Tyr Tyr Ala Asp Ser Val Lys Gly
1               5                   10                  15

```
<210> SEQ ID NO 3
<211> LENGTH: 19
<212> TYPE: PRT
<213> ORGANISM: Artificial
<220> FEATURE:
<223> OTHER INFORMATION: Synthetic KB-VWF-013 CDR3 SEQ ID NO: 3

<400> SEQUENCE: 3

Thr Ser Thr Tyr Tyr Gly Arg Ser Ala Tyr Ser Ser His Ser Gly Gly
1               5                   10                  15

Tyr Asp Tyr

<210> SEQ ID NO 4
<211> LENGTH: 128
<212> TYPE: PRT
<213> ORGANISM: Artificial
<220> FEATURE:
<223> OTHER INFORMATION: Synthetic KB-VWF-013 SEQ ID NO: 4

<400> SEQUENCE: 4

Gln Val Gln Leu Val Gln Ser Gly Gly Gly Leu Val Gln Ala Gly Asp
1               5                   10                  15

Ser Leu Arg Leu Ser Cys Ala Ala Ser Gly Arg Thr Phe Ile Arg Tyr
            20                  25                  30

Ala Met Ala Trp Phe Arg Gln Ala Pro Gly Lys Glu Arg Glu Phe Val
        35                  40                  45

Ala Ala Ile Pro Gln Ser Gly Gly Arg Ser Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Ser Cys
                85                  90                  95

Ala Ala Thr Ser Thr Tyr Tyr Gly Arg Ser Ala Tyr Ser Ser His Ser
            100                 105                 110

Gly Gly Tyr Asp Tyr Trp Gly Gln Gly Thr Gln Val Thr Val Ser Ser
        115                 120                 125

<210> SEQ ID NO 5
<211> LENGTH: 10
<212> TYPE: PRT
<213> ORGANISM: Artificial
<220> FEATURE:
<223> OTHER INFORMATION: Synthetic KB-VWF-008 CDR1 SEQ ID NO:5

<400> SEQUENCE: 5

Gly Arg Thr Phe Ser Asp Tyr Ala Met Gly
1               5                   10

<210> SEQ ID NO 6
<211> LENGTH: 16
<212> TYPE: PRT
<213> ORGANISM: Artificial
<220> FEATURE:
<223> OTHER INFORMATION: Synthetic KB-VWF-008 CDR2 SEQ ID NO: 6

<400> SEQUENCE: 6

Ile Asn Arg Ser Gly Gly Arg Leu Ser Tyr Ala Glu Ser Val Asn Asp
1               5                   10                  15

<210> SEQ ID NO 7
<211> LENGTH: 16
<212> TYPE: PRT
<213> ORGANISM: Artificial
```

```
<220> FEATURE:
<223> OTHER INFORMATION: Synthetic KB-VWF-008 CDR3 SEQ ID NO: 7

<400> SEQUENCE: 7

Arg Thr Asn Trp Asn Pro Pro Arg Pro Leu Pro Glu Glu Tyr Asn Tyr
1               5                   10                  15

<210> SEQ ID NO 8
<211> LENGTH: 125
<212> TYPE: PRT
<213> ORGANISM: Artificial
<220> FEATURE:
<223> OTHER INFORMATION: Synthetic KB-VWF-008 SEQ ID NO: 8

<400> SEQUENCE: 8

Gln Val Gln Leu Val Gln Ser Gly Gly Gly Leu Val Gln Ala Gly Asp
1               5                   10                  15

Ser Leu Lys Leu Ser Cys Ala Ala Ser Gly Arg Thr Phe Ser Asp Tyr
                20                  25                  30

Ala Met Gly Cys Ile Leu Gln Asn Pro Gly Lys Glu Arg Asp Phe Val
            35                  40                  45

Ala Ser Ile Asn Arg Ser Gly Gly Arg Leu Ser Tyr Ala Glu Ser Val
        50                  55                  60

Asn Asp Leu Phe Thr Ile Ser Val Asp Asn Ala Lys Asn Met Leu Tyr
65                  70                  75                  80

Leu Gln Met Asn Ser Leu Lys Pro Glu Asp Thr Ala Val His Tyr Cys
                85                  90                  95

Val Leu Arg Thr Asn Trp Asn Pro Pro Arg Pro Leu Pro Glu Glu Tyr
            100                 105                 110

Asn Tyr Trp Gly Gln Glu Thr Gln Val Thr Val Ser Ser
        115                 120                 125

<210> SEQ ID NO 9
<211> LENGTH: 10
<212> TYPE: PRT
<213> ORGANISM: Artificial
<220> FEATURE:
<223> OTHER INFORMATION: Synthetic KB-VWF-011 CDR1 SEQ ID NO:9

<400> SEQUENCE: 9

Gly Gly Thr Phe Ser Asn Tyr Ala Met Gly
1               5                   10

<210> SEQ ID NO 10
<211> LENGTH: 16
<212> TYPE: PRT
<213> ORGANISM: Artificial
<220> FEATURE:
<223> OTHER INFORMATION: Synthetic KB-VWF-011 CDR2 SEQ ID NO: 10

<400> SEQUENCE: 10

Ile Ser Arg Ser Gly His Arg Thr Asp Tyr Ala Asp Ser Ala Lys Gly
1               5                   10                  15

<210> SEQ ID NO 11
<211> LENGTH: 15
<212> TYPE: PRT
<213> ORGANISM: Artificial
<220> FEATURE:
<223> OTHER INFORMATION: Synthetic KB-VWF-011 CDR3 SEQ ID NO: 11
```

<400> SEQUENCE: 11

Arg Ser Asp Trp Ser Ile Ala Thr Thr Ala Thr Ser Tyr Asp Tyr
1               5                   10                  15

<210> SEQ ID NO 12
<211> LENGTH: 124
<212> TYPE: PRT
<213> ORGANISM: Artificial
<220> FEATURE:
<223> OTHER INFORMATION: Synthetic KB-VWF-011SEQ ID NO: 12

<400> SEQUENCE: 12

Gln Val Gln Leu Val Gln Ser Gly Gly Gly Leu Val Gln Ala Gly Asp
1               5                   10                  15

Ser Leu Arg Leu Ser Cys Ala Ala Ser Gly Gly Thr Phe Ser Asn Tyr
            20                  25                  30

Ala Met Gly Trp Phe Arg Gln Thr Pro Gly Lys Glu Arg Glu Phe Val
        35                  40                  45

Ala Arg Ile Ser Arg Ser Gly His Arg Thr Asp Tyr Ala Asp Ser Ala
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Arg Ser Asp Trp Ser Ile Ala Thr Thr Ala Thr Ser Tyr Asp
            100                 105                 110

Tyr Trp Gly Gln Gly Thr Gln Val Thr Val Ser Ser
        115                 120

<210> SEQ ID NO 13
<211> LENGTH: 1726
<212> TYPE: PRT
<213> ORGANISM: Artificial
<220> FEATURE:
<223> OTHER INFORMATION: Synthetic SEQ ID NO: 13

<400> SEQUENCE: 13

Met Gln Ile Glu Leu Ser Thr Cys Phe Phe Leu Cys Leu Leu Arg Phe
1               5                   10                  15

Cys Phe Ser Ala Thr Arg Arg Tyr Tyr Leu Gly Ala Val Glu Leu Ser
            20                  25                  30

Trp Asp Tyr Met Gln Ser Asp Leu Gly Glu Leu Pro Val Asp Ala Arg
        35                  40                  45

Phe Pro Pro Arg Val Pro Lys Ser Phe Pro Phe Asn Thr Ser Val Val
    50                  55                  60

Tyr Lys Lys Thr Leu Phe Val Glu Phe Thr Asp His Leu Phe Asn Ile
65                  70                  75                  80

Ala Lys Pro Arg Pro Pro Trp Met Gly Leu Leu Gly Pro Thr Ile Gln
                85                  90                  95

Ala Glu Val Tyr Asp Thr Val Val Ile Thr Leu Lys Asn Met Ala Ser
            100                 105                 110

His Pro Val Ser Leu His Ala Val Gly Val Ser Tyr Trp Lys Ala Ser
        115                 120                 125

Glu Gly Ala Glu Tyr Asp Asp Gln Thr Ser Gln Arg Glu Lys Glu Asp
    130                 135                 140

Asp Lys Val Phe Pro Gly Gly Ser His Thr Tyr Val Trp Gln Val Leu
145                 150                 155                 160

-continued

Lys Glu Asn Gly Pro Met Ala Ser Asp Pro Leu Cys Leu Thr Tyr Ser
                165                 170                 175

Tyr Leu Ser His Val Asp Leu Val Lys Asp Leu Asn Ser Gly Leu Ile
            180                 185                 190

Gly Ala Leu Leu Val Cys Arg Glu Gly Ser Leu Ala Lys Glu Lys Thr
        195                 200                 205

Gln Thr Leu His Lys Phe Ile Leu Leu Phe Ala Val Phe Asp Glu Gly
    210                 215                 220

Lys Ser Trp His Ser Glu Thr Lys Asn Ser Leu Met Gln Asp Arg Asp
225                 230                 235                 240

Ala Ala Ser Ala Arg Ala Trp Pro Lys Met His Thr Val Asn Gly Tyr
                245                 250                 255

Val Asn Arg Ser Leu Pro Gly Leu Ile Gly Cys His Arg Lys Ser Val
            260                 265                 270

Tyr Trp His Val Ile Gly Met Gly Thr Thr Pro Glu Val His Ser Ile
        275                 280                 285

Phe Leu Glu Gly His Thr Phe Leu Val Arg Asn His Arg Gln Ala Ser
    290                 295                 300

Leu Glu Ile Ser Pro Ile Thr Phe Leu Thr Ala Gln Thr Leu Leu Met
305                 310                 315                 320

Asp Leu Gly Gln Phe Leu Leu Phe Cys His Ile Ser Ser His Gln His
                325                 330                 335

Asp Gly Met Glu Ala Tyr Val Lys Val Asp Ser Cys Pro Glu Glu Pro
            340                 345                 350

Gln Leu Arg Met Lys Asn Asn Glu Ala Glu Asp Tyr Asp Asp Asp
        355                 360                 365

Leu Thr Asp Ser Glu Met Asp Val Val Arg Phe Asp Asp Asp Asn Ser
    370                 375                 380

Pro Ser Phe Ile Gln Ile Arg Ser Val Ala Lys Lys His Pro Lys Thr
385                 390                 395                 400

Trp Val His Tyr Ile Ala Ala Glu Glu Glu Asp Trp Asp Tyr Ala Pro
                405                 410                 415

Leu Val Leu Ala Pro Asp Asp Arg Ser Tyr Lys Ser Gln Tyr Leu Asn
            420                 425                 430

Asn Gly Pro Gln Arg Ile Gly Arg Lys Tyr Lys Lys Val Arg Phe Met
        435                 440                 445

Ala Tyr Thr Asp Glu Thr Phe Lys Thr Arg Glu Ala Ile Gln His Glu
    450                 455                 460

Ser Gly Ile Leu Gly Pro Leu Leu Tyr Gly Glu Val Gly Asp Thr Leu
465                 470                 475                 480

Leu Ile Ile Phe Lys Asn Gln Ala Ser Arg Pro Tyr Asn Ile Tyr Pro
                485                 490                 495

His Gly Ile Thr Asp Val Arg Pro Leu Tyr Ser Arg Arg Leu Pro Lys
            500                 505                 510

Gly Val Lys His Leu Lys Asp Phe Pro Ile Leu Pro Gly Glu Ile Phe
        515                 520                 525

Lys Tyr Lys Trp Thr Val Thr Val Glu Asp Gly Pro Thr Lys Ser Asp
    530                 535                 540

Pro Arg Cys Leu Thr Arg Tyr Tyr Ser Ser Phe Val Asn Met Glu Arg
545                 550                 555                 560

Asp Leu Ala Ser Gly Leu Ile Gly Pro Leu Leu Ile Cys Tyr Lys Glu
                565                 570                 575

```
Ser Val Asp Gln Arg Gly Asn Gln Ile Met Ser Asp Lys Arg Asn Val
            580                 585                 590

Ile Leu Phe Ser Val Phe Asp Glu Asn Arg Ser Trp Tyr Leu Thr Glu
            595                 600                 605

Asn Ile Gln Arg Phe Leu Pro Asn Pro Ala Gly Val Gln Leu Glu Asp
            610                 615                 620

Pro Glu Phe Gln Ala Ser Asn Ile Met His Ser Ile Asn Gly Tyr Val
625                 630                 635                 640

Phe Asp Ser Leu Gln Leu Ser Val Cys Leu His Glu Val Ala Tyr Trp
            645                 650                 655

Tyr Ile Leu Ser Ile Gly Ala Gln Thr Asp Phe Leu Ser Val Phe Phe
            660                 665                 670

Ser Gly Tyr Thr Phe Lys His Lys Met Val Tyr Glu Asp Thr Leu Thr
            675                 680                 685

Leu Phe Pro Phe Ser Gly Glu Thr Val Phe Met Ser Met Glu Asn Pro
            690                 695                 700

Gly Leu Trp Ile Leu Gly Cys His Asn Ser Asp Phe Arg Asn Arg Gly
705                 710                 715                 720

Met Thr Ala Leu Leu Lys Val Ser Ser Cys Asp Lys Asn Thr Gly Asp
            725                 730                 735

Tyr Tyr Glu Asp Ser Tyr Glu Asp Ile Ser Ala Tyr Leu Leu Ser Lys
            740                 745                 750

Asn Asn Ala Ile Glu Pro Arg Ser Phe Ser Gly Gly Ser Gln Val
            755                 760                 765

Gln Leu Val Gln Ser Gly Gly Gly Leu Val Gln Ala Gly Asp Ser Leu
            770                 775                 780

Arg Leu Ser Cys Ala Ala Ser Gly Arg Thr Phe Ile Arg Tyr Ala Met
785                 790                 795                 800

Ala Trp Phe Arg Gln Ala Pro Gly Lys Glu Arg Glu Phe Val Ala Ala
            805                 810                 815

Ile Pro Gln Ser Gly Gly Arg Ser Tyr Tyr Ala Asp Ser Val Lys Gly
            820                 825                 830

Arg Phe Thr Ile Ser Arg Asp Asn Ala Lys Asn Thr Val Tyr Leu Gln
            835                 840                 845

Met Asn Ser Leu Lys Pro Glu Asp Thr Ala Val Tyr Ser Cys Ala Ala
850                 855                 860

Thr Ser Thr Tyr Tyr Gly Arg Ser Ala Tyr Ser Ser His Ser Gly Gly
865                 870                 875                 880

Tyr Asp Tyr Trp Gly Gln Gly Thr Gln Val Thr Val Ser Ser Gly Gly
            885                 890                 895

Gly Ser Gly Gly Gly Ser Gly Gly Ser Gly Gly Gly Ser Gln Val
                900                 905                 910

Gln Leu Val Gln Ser Gly Gly Gly Leu Val Gln Ala Gly Asp Ser Leu
            915                 920                 925

Arg Leu Ser Cys Ala Ala Ser Gly Arg Thr Phe Ile Arg Tyr Ala Met
            930                 935                 940

Ala Trp Phe Arg Gln Ala Pro Gly Lys Glu Arg Glu Phe Val Ala Ala
945                 950                 955                 960

Ile Pro Gln Ser Gly Gly Arg Ser Tyr Tyr Ala Asp Ser Val Lys Gly
            965                 970                 975

Arg Phe Thr Ile Ser Arg Asp Asn Ala Lys Asn Thr Val Tyr Leu Gln
            980                 985                 990
```

```
Met Asn Ser Leu Lys Pro Glu Asp Thr Ala Val Tyr Ser Cys Ala Ala
        995                 1000                1005

Thr Ser Thr Tyr Tyr Gly Arg Ser Ala Tyr Ser Ser His Ser Gly
    1010                1015                1020

Gly Tyr Asp Tyr Trp Gly Gln Gly Thr Gln Val Thr Val Ser Ser
    1025                1030                1035

Gly Gly Gly Ser Glu Ile Thr Arg Thr Thr Leu Gln Ser Asp Gln
    1040                1045                1050

Glu Glu Ile Asp Tyr Asp Asp Thr Ile Ser Val Glu Met Lys Lys
    1055                1060                1065

Glu Asp Phe Asp Ile Tyr Asp Glu Asp Glu Asn Gln Ser Pro Arg
    1070                1075                1080

Ser Phe Gln Lys Lys Thr Arg His Tyr Phe Ile Ala Ala Val Glu
    1085                1090                1095

Arg Leu Trp Asp Tyr Gly Met Ser Ser Ser Pro His Val Leu Arg
    1100                1105                1110

Asn Arg Ala Gln Ser Gly Ser Val Pro Gln Phe Lys Lys Val Val
    1115                1120                1125

Phe Gln Glu Phe Thr Asp Gly Ser Phe Thr Gln Pro Leu Tyr Arg
    1130                1135                1140

Gly Glu Leu Asn Glu His Leu Gly Leu Leu Gly Pro Tyr Ile Arg
    1145                1150                1155

Ala Glu Val Glu Asp Asn Ile Met Val Thr Phe Arg Asn Gln Ala
    1160                1165                1170

Ser Arg Pro Tyr Ser Phe Tyr Ser Ser Leu Ile Ser Tyr Glu Glu
    1175                1180                1185

Asp Gln Arg Gln Gly Ala Glu Pro Arg Lys Asn Phe Val Lys Pro
    1190                1195                1200

Asn Glu Thr Lys Thr Tyr Phe Trp Lys Val Gln His His Met Ala
    1205                1210                1215

Pro Thr Lys Asp Glu Phe Asp Cys Lys Ala Trp Ala Tyr Phe Ser
    1220                1225                1230

Asp Val Asp Leu Glu Lys Asp Val His Ser Gly Leu Ile Gly Pro
    1235                1240                1245

Leu Leu Val Cys His Thr Asn Thr Leu Asn Pro Ala His Gly Arg
    1250                1255                1260

Gln Val Thr Val Gln Glu Phe Ala Leu Phe Phe Thr Ile Phe Asp
    1265                1270                1275

Glu Thr Lys Ser Trp Tyr Phe Thr Glu Asn Met Glu Arg Asn Cys
    1280                1285                1290

Arg Ala Pro Cys Asn Ile Gln Met Glu Asp Pro Thr Phe Lys Glu
    1295                1300                1305

Asn Tyr Arg Phe His Ala Ile Asn Gly Tyr Ile Met Asp Thr Leu
    1310                1315                1320

Pro Gly Leu Val Met Ala Gln Asp Gln Arg Ile Arg Trp Tyr Leu
    1325                1330                1335

Leu Ser Met Gly Ser Asn Glu Asn Ile His Ser Ile His Phe Ser
    1340                1345                1350

Gly His Val Phe Thr Val Arg Lys Lys Glu Glu Tyr Lys Met Ala
    1355                1360                1365

Leu Tyr Asn Leu Tyr Pro Gly Val Phe Glu Thr Val Glu Met Leu
    1370                1375                1380
```

Pro Ser Lys Ala Gly Ile Trp Arg Val Glu Cys Leu Ile Gly Glu
    1385                1390                1395

His Leu His Ala Gly Met Ser Thr Leu Phe Leu Val Tyr Ser Asn
    1400                1405                1410

Lys Cys Gln Thr Pro Leu Gly Met Ala Ser Gly His Ile Arg Asp
    1415                1420                1425

Phe Gln Ile Thr Ala Ser Gly Gln Tyr Gly Gln Trp Ala Pro Lys
    1430                1435                1440

Leu Ala Arg Leu His Tyr Ser Gly Ser Ile Asn Ala Trp Ser Thr
    1445                1450                1455

Lys Glu Pro Phe Ser Trp Ile Lys Val Asp Leu Leu Ala Pro Met
    1460                1465                1470

Ile Ile His Gly Ile Lys Thr Gln Gly Ala Arg Gln Lys Phe Ser
    1475                1480                1485

Ser Leu Tyr Ile Ser Gln Phe Ile Ile Met Tyr Ser Leu Asp Gly
    1490                1495                1500

Lys Lys Trp Gln Thr Tyr Arg Gly Asn Ser Thr Gly Thr Leu Met
    1505                1510                1515

Val Phe Phe Gly Asn Val Asp Ser Ser Gly Ile Lys His Asn Ile
    1520                1525                1530

Phe Asn Pro Pro Ile Ile Ala Arg Tyr Ile Arg Leu His Pro Thr
    1535                1540                1545

His Tyr Ser Ile Arg Ser Thr Leu Arg Met Glu Trp Met Gly Cys
    1550                1555                1560

Asp Leu Asn Ser Cys Ser Met Pro Leu Gly Met Glu Ser Lys Ala
    1565                1570                1575

Ile Ser Asp Ala Gln Ile Thr Ala Ser Ser Tyr Phe Thr Asn Met
    1580                1585                1590

Phe Ala Thr Trp Ser Pro Ser Lys Ala Arg Leu His Leu Gln Gly
    1595                1600                1605

Arg Ser Asn Ala Trp Arg Pro Gln Val Asn Asn Pro Lys Glu Trp
    1610                1615                1620

Leu Gln Val Asp Phe Gln Lys Thr Met Lys Val Thr Gly Val Thr
    1625                1630                1635

Thr Gln Gly Val Lys Ser Leu Leu Thr Ser Met Tyr Val Lys Glu
    1640                1645                1650

Phe Leu Ile Ser Ser Ser Gln Asp Gly His Gln Trp Thr Leu Phe
    1655                1660                1665

Phe Gln Asn Gly Lys Val Lys Val Phe Gln Gly Asn Gln Asp Ser
    1670                1675                1680

Phe Thr Pro Val Val Asn Ser Leu Asp Pro Pro Leu Leu Thr Arg
    1685                1690                1695

Tyr Leu Arg Ile His Pro Gln Ser Trp Val His Gln Ile Ala Leu
    1700                1705                1710

Arg Met Glu Val Leu Gly Cys Glu Ala Gln Asp Leu Tyr
    1715                1720                1725

<210> SEQ ID NO 14
<211> LENGTH: 761
<212> TYPE: PRT
<213> ORGANISM: Artificial
<220> FEATURE:
<223> OTHER INFORMATION: Synthetic FVII-KB13-bv SEQ ID NO: 14

<400> SEQUENCE: 14

```
Met Val Ser Gln Ala Leu Arg Leu Leu Cys Leu Leu Leu Gly Leu Gln
1               5                   10                  15

Gly Cys Leu Ala Ala Gly Gly Val Ala Lys Ala Ser Gly Gly Glu Thr
            20                  25                  30

Arg Asp Met Pro Trp Lys Pro Gly His Arg Val Phe Val Thr Gln
        35                  40                  45

Glu Glu Ala His Gly Val Leu His Arg Arg Arg Ala Asn Ala Phe
50                  55                  60

Leu Glu Glu Leu Arg Pro Gly Ser Leu Glu Arg Glu Cys Lys Glu Glu
65                  70                  75                  80

Gln Cys Ser Phe Glu Glu Ala Arg Glu Ile Phe Lys Asp Ala Glu Arg
                85                  90                  95

Thr Lys Leu Phe Trp Ile Ser Tyr Ser Asp Gly Asp Gln Cys Ala Ser
            100                 105                 110

Ser Pro Cys Gln Asn Gly Gly Ser Cys Lys Asp Gln Leu Gln Ser Tyr
        115                 120                 125

Ile Cys Phe Cys Leu Pro Ala Phe Glu Gly Arg Asn Cys Glu Thr His
    130                 135                 140

Lys Asp Asp Gln Leu Ile Cys Val Asn Glu Asn Gly Gly Cys Glu Gln
145                 150                 155                 160

Tyr Cys Ser Asp His Thr Gly Thr Lys Arg Ser Cys Arg Cys His Glu
                165                 170                 175

Gly Tyr Ser Leu Leu Ala Asp Gly Val Ser Cys Thr Pro Thr Val Glu
            180                 185                 190

Tyr Pro Cys Gly Lys Ile Pro Ile Leu Glu Lys Arg Asn Ala Ser Lys
        195                 200                 205

Pro Gln Gly Arg Ile Val Gly Gly Lys Val Cys Pro Lys Gly Glu Cys
    210                 215                 220

Pro Gln Val Leu Leu Leu Val Asn Gly Ala Gln Leu Cys Gly Gly Thr
225                 230                 235                 240

Leu Ile Asn Thr Ile Trp Val Val Ser Ala Ala His Cys Phe Asp Lys
                245                 250                 255

Ile Lys Asn Trp Arg Asn Leu Ile Ala Val Leu Gly Glu His Asp Leu
            260                 265                 270

Ser Glu His Asp Gly Asp Glu Gln Ser Arg Arg Val Ala Gln Val Ile
        275                 280                 285

Ile Pro Ser Thr Tyr Val Pro Gly Thr Thr Asn His Asp Ile Ala Leu
    290                 295                 300

Leu Arg Leu His Gln Pro Val Val Leu Thr Asp His Val Val Pro Leu
305                 310                 315                 320

Cys Leu Pro Glu Arg Thr Phe Ser Glu Arg Thr Leu Ala Phe Val Arg
                325                 330                 335

Phe Ser Leu Val Ser Gly Trp Gly Gln Leu Leu Asp Arg Gly Ala Thr
            340                 345                 350

Ala Leu Glu Leu Met Val Leu Asn Val Pro Arg Leu Met Thr Gln Asp
        355                 360                 365

Cys Leu Gln Gln Ser Arg Lys Val Gly Asp Ser Pro Asn Ile Thr Glu
    370                 375                 380

Tyr Met Phe Cys Ala Gly Tyr Ser Asp Gly Ser Lys Asp Ser Cys Lys
385                 390                 395                 400
```

-continued

Gly Asp Ser Gly Gly Pro His Ala Thr His Tyr Arg Gly Thr Trp Tyr
            405                 410                 415
Leu Thr Gly Ile Val Ser Trp Gly Gln Gly Cys Ala Thr Val Gly His
            420                 425                 430
Phe Gly Val Tyr Thr Arg Val Ser Gln Tyr Ile Glu Trp Leu Gln Lys
            435                 440                 445
Leu Met Arg Ser Glu Pro Arg Pro Gly Val Leu Leu Arg Ala Pro Phe
450                 455                 460
Pro Leu Thr Pro Arg Gly Val Arg Leu Gly Gly Ser Gly Gly
465                 470                 475                 480
Ser Gly Gly Ser Gly Gly Ser Gln Val Gln Leu Val Gln Ser
            485                 490                 495
Gly Gly Gly Leu Val Gln Ala Gly Asp Ser Leu Arg Leu Ser Cys Ala
            500                 505                 510
Ala Ser Gly Arg Thr Phe Ile Arg Tyr Ala Met Ala Trp Phe Arg Gln
            515                 520                 525
Ala Pro Gly Lys Glu Arg Glu Phe Val Ala Ala Ile Pro Gln Ser Gly
            530                 535                 540
Gly Arg Ser Tyr Tyr Ala Asp Ser Val Lys Gly Arg Phe Thr Ile Ser
545                 550                 555                 560
Arg Asp Asn Ala Lys Asn Thr Val Tyr Leu Gln Met Asn Ser Leu Lys
            565                 570                 575
Pro Glu Asp Thr Ala Val Tyr Ser Cys Ala Ala Thr Ser Thr Tyr Tyr
            580                 585                 590
Gly Arg Ser Ala Tyr Ser Ser His Ser Gly Gly Tyr Asp Tyr Trp Gly
            595                 600                 605
Gln Gly Thr Gln Val Thr Val Ser Ser Gly Gly Gly Ser Gly Gly
            610                 615                 620
Ser Gly Gly Ser Gly Gly Ser Gln Val Gln Leu Val Gln Ser
625                 630                 635                 640
Gly Gly Gly Leu Val Gln Ala Gly Asp Ser Leu Arg Leu Ser Cys Ala
            645                 650                 655
Ala Ser Gly Arg Thr Phe Ile Arg Tyr Ala Met Ala Trp Phe Arg Gln
            660                 665                 670
Ala Pro Gly Lys Glu Arg Glu Phe Val Ala Ala Ile Pro Gln Ser Gly
            675                 680                 685
Gly Arg Ser Tyr Tyr Ala Asp Ser Val Lys Gly Arg Phe Thr Ile Ser
            690                 695                 700
Arg Asp Asn Ala Lys Asn Thr Val Tyr Leu Gln Met Asn Ser Leu Lys
705                 710                 715                 720
Pro Glu Asp Thr Ala Val Tyr Ser Cys Ala Ala Thr Ser Thr Tyr Tyr
            725                 730                 735
Gly Arg Ser Ala Tyr Ser Ser His Ser Gly Gly Tyr Asp Tyr Trp Gly
            740                 745                 750
Gln Gly Thr Gln Val Thr Val Ser Ser
            755                 760

<210> SEQ ID NO 15
<211> LENGTH: 12
<212> TYPE: PRT
<213> ORGANISM: Artificial
<220> FEATURE:
<223> OTHER INFORMATION: Synthetic SEQ ID NO: 15

<400> SEQUENCE: 15

Glu Asp Gln Val Asp Pro Arg Leu Ile Asp Gly Lys
1               5                   10

<210> SEQ ID NO 16
<211> LENGTH: 1746
<212> TYPE: PRT
<213> ORGANISM: Artificial
<220> FEATURE:
<223> OTHER INFORMATION: Synthetic FVIII_KB0013bv(6GGGS) SEQ ID NO: 16

<400> SEQUENCE: 16

Met Gln Ile Glu Leu Ser Thr Cys Phe Phe Leu Cys Leu Leu Arg Phe
1               5                   10                  15

Cys Phe Ser Ala Thr Arg Arg Tyr Tyr Leu Gly Ala Val Glu Leu Ser
            20                  25                  30

Trp Asp Tyr Met Gln Ser Asp Leu Gly Glu Leu Pro Val Asp Ala Arg
        35                  40                  45

Phe Pro Pro Arg Val Pro Lys Ser Phe Pro Phe Asn Thr Ser Val Val
    50                  55                  60

Tyr Lys Lys Thr Leu Phe Val Glu Phe Thr Asp His Leu Phe Asn Ile
65                  70                  75                  80

Ala Lys Pro Arg Pro Pro Trp Met Gly Leu Leu Gly Pro Thr Ile Gln
                85                  90                  95

Ala Glu Val Tyr Asp Thr Val Val Ile Thr Leu Lys Asn Met Ala Ser
            100                 105                 110

His Pro Val Ser Leu His Ala Val Gly Val Ser Tyr Trp Lys Ala Ser
        115                 120                 125

Glu Gly Ala Glu Tyr Asp Asp Gln Thr Ser Gln Arg Glu Lys Glu Asp
    130                 135                 140

Asp Lys Val Phe Pro Gly Gly Ser His Thr Tyr Val Trp Gln Val Leu
145                 150                 155                 160

Lys Glu Asn Gly Pro Met Ala Ser Asp Pro Leu Cys Leu Thr Tyr Ser
                165                 170                 175

Tyr Leu Ser His Val Asp Leu Val Lys Asp Leu Asn Ser Gly Leu Ile
            180                 185                 190

Gly Ala Leu Leu Val Cys Arg Glu Gly Ser Leu Ala Lys Glu Lys Thr
        195                 200                 205

Gln Thr Leu His Lys Phe Ile Leu Leu Phe Ala Val Phe Asp Glu Gly
    210                 215                 220

Lys Ser Trp His Ser Glu Thr Lys Asn Ser Leu Met Gln Asp Arg Asp
225                 230                 235                 240

Ala Ala Ser Ala Arg Ala Trp Pro Lys Met His Thr Val Asn Gly Tyr
                245                 250                 255

Val Asn Arg Ser Leu Pro Gly Leu Ile Gly Cys His Arg Lys Ser Val
            260                 265                 270

Tyr Trp His Val Ile Gly Met Gly Thr Thr Pro Glu Val His Ser Ile
        275                 280                 285

Phe Leu Glu Gly His Thr Phe Leu Val Arg Asn His Arg Gln Ala Ser
    290                 295                 300

Leu Glu Ile Ser Pro Ile Thr Phe Leu Thr Ala Gln Thr Leu Leu Met
305                 310                 315                 320

Asp Leu Gly Gln Phe Leu Leu Phe Cys His Ile Ser Ser His Gln His
                325                 330                 335

```
Asp Gly Met Glu Ala Tyr Val Lys Val Asp Ser Cys Pro Glu Pro
            340                 345                 350

Gln Leu Arg Met Lys Asn Asn Glu Glu Ala Glu Asp Tyr Asp Asp
            355                 360                 365

Leu Thr Asp Ser Glu Met Asp Val Val Arg Phe Asp Asp Asn Ser
            370                 375                 380

Pro Ser Phe Ile Gln Ile Arg Ser Val Ala Lys Lys His Pro Lys Thr
385                 390                 395                 400

Trp Val His Tyr Ile Ala Ala Glu Glu Asp Trp Asp Tyr Ala Pro
                405                 410                 415

Leu Val Leu Ala Pro Asp Asp Arg Ser Tyr Lys Ser Gln Tyr Leu Asn
            420                 425                 430

Asn Gly Pro Gln Arg Ile Gly Arg Lys Tyr Lys Lys Val Arg Phe Met
            435                 440                 445

Ala Tyr Thr Asp Glu Thr Phe Lys Thr Arg Glu Ala Ile Gln His Glu
            450                 455                 460

Ser Gly Ile Leu Gly Pro Leu Leu Tyr Gly Glu Val Gly Asp Thr Leu
465                 470                 475                 480

Leu Ile Ile Phe Lys Asn Gln Ala Ser Arg Pro Tyr Asn Ile Tyr Pro
                485                 490                 495

His Gly Ile Thr Asp Val Arg Pro Leu Tyr Ser Arg Arg Leu Pro Lys
                500                 505                 510

Gly Val Lys His Leu Lys Asp Phe Pro Ile Leu Pro Gly Glu Ile Phe
            515                 520                 525

Lys Tyr Lys Trp Thr Val Thr Val Glu Asp Gly Pro Thr Lys Ser Asp
530                 535                 540

Pro Arg Cys Leu Thr Arg Tyr Tyr Ser Ser Phe Val Asn Met Glu Arg
545                 550                 555                 560

Asp Leu Ala Ser Gly Leu Ile Gly Pro Leu Leu Ile Cys Tyr Lys Glu
                565                 570                 575

Ser Val Asp Gln Arg Gly Asn Gln Ile Met Ser Asp Lys Arg Asn Val
            580                 585                 590

Ile Leu Phe Ser Val Phe Asp Glu Asn Arg Ser Trp Tyr Leu Thr Glu
            595                 600                 605

Asn Ile Gln Arg Phe Leu Pro Asn Pro Ala Gly Val Gln Leu Glu Asp
610                 615                 620

Pro Glu Phe Gln Ala Ser Asn Ile Met His Ser Ile Asn Gly Tyr Val
625                 630                 635                 640

Phe Asp Ser Leu Gln Leu Ser Val Cys Leu His Glu Val Ala Tyr Trp
                645                 650                 655

Tyr Ile Leu Ser Ile Gly Ala Gln Thr Asp Phe Leu Ser Val Phe Phe
            660                 665                 670

Ser Gly Tyr Thr Phe Lys His Lys Met Val Tyr Glu Asp Thr Leu Thr
            675                 680                 685

Leu Phe Pro Phe Ser Gly Glu Thr Val Phe Met Ser Met Glu Asn Pro
            690                 695                 700

Gly Leu Trp Ile Leu Gly Cys His Asn Ser Asp Phe Arg Asn Arg Gly
705                 710                 715                 720

Met Thr Ala Leu Leu Lys Val Ser Ser Cys Asp Lys Asn Thr Gly Asp
                725                 730                 735

Tyr Tyr Glu Asp Ser Tyr Glu Asp Ile Ser Ala Tyr Leu Leu Ser Lys
            740                 745                 750
```

```
Asn Asn Ala Ile Glu Pro Arg Ser Phe Ser Gly Gly Ser Gln Val
        755                 760                 765

Gln Leu Val Gln Ser Gly Gly Leu Val Gln Ala Gly Asp Ser Leu
        770                 775                 780

Arg Leu Ser Cys Ala Ala Ser Gly Arg Thr Phe Ile Arg Tyr Ala Met
785                 790                 795                 800

Ala Trp Phe Arg Gln Ala Pro Gly Lys Glu Arg Glu Phe Val Ala Ala
                805                 810                 815

Ile Pro Gln Ser Gly Gly Arg Ser Tyr Tyr Ala Asp Ser Val Lys Gly
                820                 825                 830

Arg Phe Thr Ile Ser Arg Asp Asn Ala Lys Asn Thr Val Tyr Leu Gln
                835                 840                 845

Met Asn Ser Leu Lys Pro Glu Asp Thr Ala Val Tyr Ser Cys Ala Ala
        850                 855                 860

Thr Ser Thr Tyr Tyr Gly Arg Ser Ala Tyr Ser Ser His Ser Gly Gly
865                 870                 875                 880

Tyr Asp Tyr Trp Gly Gln Gly Thr Gln Val Thr Val Ser Ser Gly Gly
                    885                 890                 895

Gly Ser Gly Gly Gly Ser Gly Gly Ser Gly Gly Ser Gln Val
            900                 905                 910

Gln Leu Val Gln Ser Gly Gly Leu Val Gln Ala Gly Asp Ser Leu
        915                 920                 925

Arg Leu Ser Cys Ala Ala Ser Gly Arg Thr Phe Ile Arg Tyr Ala Met
    930                 935                 940

Ala Trp Phe Arg Gln Ala Pro Gly Lys Glu Arg Glu Phe Val Ala Ala
945                 950                 955                 960

Ile Pro Gln Ser Gly Gly Arg Ser Tyr Tyr Ala Asp Ser Val Lys Gly
                965                 970                 975

Arg Phe Thr Ile Ser Arg Asp Asn Ala Lys Asn Thr Val Tyr Leu Gln
                980                 985                 990

Met Asn Ser Leu Lys Pro Glu Asp  Thr Ala Val Tyr Ser  Cys Ala Ala
        995                  1000                 1005

Thr Ser  Thr Tyr Tyr Gly Arg  Ser Ala Tyr Ser Ser  His Ser Gly
    1010                 1015                 1020

Gly Tyr  Asp Tyr Trp Gly Gln  Gly Thr Gln Val Thr  Val Ser Ser
    1025                 1030                 1035

Gly Gly  Gly Ser Gly Gly Gly  Ser Gly Gly Ser  Gly Gly Gly
    1040                 1045                 1050

Ser Gly  Gly Gly Ser Gly Gly  Gly Ser Glu Ile Thr  Arg Thr Thr
    1055                 1060                 1065

Leu Gln  Ser Asp Gln Glu Glu  Ile Asp Tyr Asp Asp  Thr Ile Ser
    1070                 1075                 1080

Val Glu  Met Lys Lys Glu Asp  Phe Asp Ile Tyr Asp  Glu Asp Glu
    1085                 1090                 1095

Asn Gln  Ser Pro Arg Ser Phe  Gln Lys Lys Thr Arg  His Tyr Phe
    1100                 1105                 1110

Ile Ala  Ala Val Glu Arg Leu  Trp Asp Tyr Gly Met  Ser Ser Ser
    1115                 1120                 1125

Pro His  Val Leu Arg Asn Arg  Ala Gln Ser Gly Ser  Val Pro Gln
    1130                 1135                 1140

Phe Lys  Lys Val Val Phe Gln  Glu Phe Thr Asp Gly  Ser Phe Thr
    1145                 1150                 1155
```

```
Gln Pro Leu Tyr Arg Gly Glu Leu Asn Glu His Leu Gly Leu Leu
1160                1165                1170

Gly Pro Tyr Ile Arg Ala Glu Val Glu Asp Asn Ile Met Val Thr
1175                1180                1185

Phe Arg Asn Gln Ala Ser Arg Pro Tyr Ser Phe Tyr Ser Ser Leu
1190                1195                1200

Ile Ser Tyr Glu Glu Asp Gln Arg Gln Gly Ala Glu Pro Arg Lys
1205                1210                1215

Asn Phe Val Lys Pro Asn Glu Thr Lys Thr Tyr Phe Trp Lys Val
1220                1225                1230

Gln His His Met Ala Pro Thr Lys Asp Glu Phe Asp Cys Lys Ala
1235                1240                1245

Trp Ala Tyr Phe Ser Asp Val Asp Leu Glu Lys Asp Val His Ser
1250                1255                1260

Gly Leu Ile Gly Pro Leu Leu Val Cys His Thr Asn Thr Leu Asn
1265                1270                1275

Pro Ala His Gly Arg Gln Val Thr Val Gln Glu Phe Ala Leu Phe
1280                1285                1290

Phe Thr Ile Phe Asp Glu Thr Lys Ser Trp Tyr Phe Thr Glu Asn
1295                1300                1305

Met Glu Arg Asn Cys Arg Ala Pro Cys Asn Ile Gln Met Glu Asp
1310                1315                1320

Pro Thr Phe Lys Glu Asn Tyr Arg Phe His Ala Ile Asn Gly Tyr
1325                1330                1335

Ile Met Asp Thr Leu Pro Gly Leu Val Met Ala Gln Asp Gln Arg
1340                1345                1350

Ile Arg Trp Tyr Leu Leu Ser Met Gly Ser Asn Glu Asn Ile His
1355                1360                1365

Ser Ile His Phe Ser Gly His Val Phe Thr Val Arg Lys Lys Glu
1370                1375                1380

Glu Tyr Lys Met Ala Leu Tyr Asn Leu Tyr Pro Gly Val Phe Glu
1385                1390                1395

Thr Val Glu Met Leu Pro Ser Lys Ala Gly Ile Trp Arg Val Glu
1400                1405                1410

Cys Leu Ile Gly Glu His Leu His Ala Gly Met Ser Thr Leu Phe
1415                1420                1425

Leu Val Tyr Ser Asn Lys Cys Gln Thr Pro Leu Gly Met Ala Ser
1430                1435                1440

Gly His Ile Arg Asp Phe Gln Ile Thr Ala Ser Gly Gln Tyr Gly
1445                1450                1455

Gln Trp Ala Pro Lys Leu Ala Arg Leu His Tyr Ser Gly Ser Ile
1460                1465                1470

Asn Ala Trp Ser Thr Lys Glu Pro Phe Ser Trp Ile Lys Val Asp
1475                1480                1485

Leu Leu Ala Pro Met Ile Ile His Gly Ile Lys Thr Gln Gly Ala
1490                1495                1500

Arg Gln Lys Phe Ser Ser Leu Tyr Ile Ser Gln Phe Ile Ile Met
1505                1510                1515

Tyr Ser Leu Asp Gly Lys Lys Trp Gln Thr Tyr Arg Gly Asn Ser
1520                1525                1530

Thr Gly Thr Leu Met Val Phe Phe Gly Asn Val Asp Ser Ser Gly
1535                1540                1545
```

```
Ile Lys His Asn Ile Phe Asn Pro Pro Ile Ile Ala Arg Tyr Ile
    1550                1555                1560

Arg Leu His Pro Thr His Tyr Ser Ile Arg Ser Thr Leu Arg Met
    1565                1570                1575

Glu Trp Met Gly Cys Asp Leu Asn Ser Cys Ser Met Pro Leu Gly
    1580                1585                1590

Met Glu Ser Lys Ala Ile Ser Asp Ala Gln Ile Thr Ala Ser Ser
    1595                1600                1605

Tyr Phe Thr Asn Met Phe Ala Thr Trp Ser Pro Ser Lys Ala Arg
    1610                1615                1620

Leu His Leu Gln Gly Arg Ser Asn Ala Trp Arg Pro Gln Val Asn
    1625                1630                1635

Asn Pro Lys Glu Trp Leu Gln Val Asp Phe Gln Lys Thr Met Lys
    1640                1645                1650

Val Thr Gly Val Thr Thr Gln Gly Val Lys Ser Leu Leu Thr Ser
    1655                1660                1665

Met Tyr Val Lys Glu Phe Leu Ile Ser Ser Ser Gln Asp Gly His
    1670                1675                1680

Gln Trp Thr Leu Phe Phe Gln Asn Gly Lys Val Lys Val Phe Gln
    1685                1690                1695

Gly Asn Gln Asp Ser Phe Thr Pro Val Val Asn Ser Leu Asp Pro
    1700                1705                1710

Pro Leu Leu Thr Arg Tyr Leu Arg Ile His Pro Gln Ser Trp Val
    1715                1720                1725

His Gln Ile Ala Leu Arg Met Glu Val Leu Gly Cys Glu Ala Gln
    1730                1735                1740

Asp Leu Tyr
    1745

<210> SEQ ID NO 17
<211> LENGTH: 1746
<212> TYPE: PRT
<213> ORGANISM: Artificial
<220> FEATURE:
<223> OTHER INFORMATION: Synthetic FVIII_KB0013bv(6GGGS)_Y1680F SEQ ID
      NO: 17

<400> SEQUENCE: 17

Met Gln Ile Glu Leu Ser Thr Cys Phe Phe Leu Cys Leu Leu Arg Phe
1               5                   10                  15

Cys Phe Ser Ala Thr Arg Arg Tyr Tyr Leu Gly Ala Val Glu Leu Ser
                20                  25                  30

Trp Asp Tyr Met Gln Ser Asp Leu Gly Glu Leu Pro Val Asp Ala Arg
            35                  40                  45

Phe Pro Pro Arg Val Pro Lys Ser Phe Pro Phe Asn Thr Ser Val Val
        50                  55                  60

Tyr Lys Lys Thr Leu Phe Val Glu Phe Thr Asp His Leu Phe Asn Ile
65                  70                  75                  80

Ala Lys Pro Arg Pro Pro Trp Met Gly Leu Leu Gly Pro Thr Ile Gln
                85                  90                  95

Ala Glu Val Tyr Asp Thr Val Val Ile Thr Leu Lys Asn Met Ala Ser
            100                 105                 110

His Pro Val Ser Leu His Ala Val Gly Val Ser Tyr Trp Lys Ala Ser
        115                 120                 125
```

```
Glu Gly Ala Glu Tyr Asp Asp Gln Thr Ser Gln Arg Glu Lys Glu Asp
    130                 135                 140

Asp Lys Val Phe Pro Gly Gly Ser His Thr Tyr Val Trp Gln Val Leu
145                 150                 155                 160

Lys Glu Asn Gly Pro Met Ala Ser Asp Pro Leu Cys Leu Thr Tyr Ser
                165                 170                 175

Tyr Leu Ser His Val Asp Leu Val Lys Asp Leu Asn Ser Gly Leu Ile
            180                 185                 190

Gly Ala Leu Leu Val Cys Arg Glu Gly Ser Leu Ala Lys Glu Lys Thr
        195                 200                 205

Gln Thr Leu His Lys Phe Ile Leu Leu Phe Ala Val Phe Asp Glu Gly
    210                 215                 220

Lys Ser Trp His Ser Glu Thr Lys Asn Ser Leu Met Gln Asp Arg Asp
225                 230                 235                 240

Ala Ala Ser Ala Arg Ala Trp Pro Lys Met His Thr Val Asn Gly Tyr
                245                 250                 255

Val Asn Arg Ser Leu Pro Gly Leu Ile Gly Cys His Arg Lys Ser Val
            260                 265                 270

Tyr Trp His Val Ile Gly Met Gly Thr Thr Pro Glu Val His Ser Ile
        275                 280                 285

Phe Leu Glu Gly His Thr Phe Leu Val Arg Asn His Arg Gln Ala Ser
    290                 295                 300

Leu Glu Ile Ser Pro Ile Thr Phe Leu Thr Ala Gln Thr Leu Leu Met
305                 310                 315                 320

Asp Leu Gly Gln Phe Leu Leu Phe Cys His Ile Ser Ser His Gln His
                325                 330                 335

Asp Gly Met Glu Ala Tyr Val Lys Val Asp Ser Cys Pro Glu Glu Pro
            340                 345                 350

Gln Leu Arg Met Lys Asn Asn Glu Glu Ala Glu Asp Tyr Asp Asp Asp
        355                 360                 365

Leu Thr Asp Ser Glu Met Asp Val Val Arg Phe Asp Asp Asp Asn Ser
    370                 375                 380

Pro Ser Phe Ile Gln Ile Arg Ser Val Ala Lys Lys His Pro Lys Thr
385                 390                 395                 400

Trp Val His Tyr Ile Ala Ala Glu Glu Glu Asp Trp Asp Tyr Ala Pro
                405                 410                 415

Leu Val Leu Ala Pro Asp Asp Arg Ser Tyr Lys Ser Gln Tyr Leu Asn
            420                 425                 430

Asn Gly Pro Gln Arg Ile Gly Arg Lys Tyr Lys Lys Val Arg Phe Met
        435                 440                 445

Ala Tyr Thr Asp Glu Thr Phe Lys Thr Arg Glu Ala Ile Gln His Glu
    450                 455                 460

Ser Gly Ile Leu Gly Pro Leu Leu Tyr Gly Glu Val Gly Asp Thr Leu
465                 470                 475                 480

Leu Ile Ile Phe Lys Asn Gln Ala Ser Arg Pro Tyr Asn Ile Tyr Pro
                485                 490                 495

His Gly Ile Thr Asp Val Arg Pro Leu Tyr Ser Arg Arg Leu Pro Lys
            500                 505                 510

Gly Val Lys His Leu Lys Asp Phe Pro Ile Leu Pro Gly Glu Ile Phe
        515                 520                 525

Lys Tyr Lys Trp Thr Val Thr Val Glu Asp Gly Pro Thr Lys Ser Asp
    530                 535                 540
```

```
Pro Arg Cys Leu Thr Arg Tyr Tyr Ser Ser Phe Val Asn Met Glu Arg
545                 550                 555                 560

Asp Leu Ala Ser Gly Leu Ile Gly Pro Leu Leu Ile Cys Tyr Lys Glu
            565                 570                 575

Ser Val Asp Gln Arg Gly Asn Gln Ile Met Ser Asp Lys Arg Asn Val
        580                 585                 590

Ile Leu Phe Ser Val Phe Asp Glu Asn Arg Ser Trp Tyr Leu Thr Glu
    595                 600                 605

Asn Ile Gln Arg Phe Leu Pro Asn Pro Ala Gly Val Gln Leu Glu Asp
610                 615                 620

Pro Glu Phe Gln Ala Ser Asn Ile Met His Ser Ile Asn Gly Tyr Val
625                 630                 635                 640

Phe Asp Ser Leu Gln Leu Ser Val Cys Leu His Glu Val Ala Tyr Trp
            645                 650                 655

Tyr Ile Leu Ser Ile Gly Ala Gln Thr Asp Phe Leu Ser Val Phe Phe
            660                 665                 670

Ser Gly Tyr Thr Phe Lys His Lys Met Val Tyr Glu Asp Thr Leu Thr
        675                 680                 685

Leu Phe Pro Phe Ser Gly Glu Thr Val Phe Met Ser Met Glu Asn Pro
690                 695                 700

Gly Leu Trp Ile Leu Gly Cys His Asn Ser Asp Phe Arg Asn Arg Gly
705                 710                 715                 720

Met Thr Ala Leu Leu Lys Val Ser Ser Cys Asp Lys Asn Thr Gly Asp
            725                 730                 735

Tyr Tyr Glu Asp Ser Tyr Glu Asp Ile Ser Ala Tyr Leu Leu Ser Lys
        740                 745                 750

Asn Asn Ala Ile Glu Pro Arg Ser Phe Ser Gly Gly Ser Gln Val
            755                 760                 765

Gln Leu Val Gln Ser Gly Gly Gly Leu Val Gln Ala Gly Asp Ser Leu
    770                 775                 780

Arg Leu Ser Cys Ala Ala Ser Gly Arg Thr Phe Ile Arg Tyr Ala Met
785                 790                 795                 800

Ala Trp Phe Arg Gln Ala Pro Gly Lys Glu Arg Glu Phe Val Ala Ala
            805                 810                 815

Ile Pro Gln Ser Gly Gly Arg Ser Tyr Tyr Ala Asp Ser Val Lys Gly
        820                 825                 830

Arg Phe Thr Ile Ser Arg Asp Asn Ala Lys Asn Thr Val Tyr Leu Gln
            835                 840                 845

Met Asn Ser Leu Lys Pro Glu Asp Thr Ala Val Tyr Ser Cys Ala Ala
850                 855                 860

Thr Ser Thr Tyr Tyr Gly Arg Ser Ala Tyr Ser Ser His Ser Gly Gly
865                 870                 875                 880

Tyr Asp Tyr Trp Gly Gln Gly Thr Gln Val Thr Val Ser Ser Gly Gly
            885                 890                 895

Gly Ser Gly Gly Gly Ser Gly Gly Gly Ser Gly Gly Gly Ser Gln Val
        900                 905                 910

Gln Leu Val Gln Ser Gly Gly Gly Leu Val Gln Ala Gly Asp Ser Leu
    915                 920                 925

Arg Leu Ser Cys Ala Ala Ser Gly Arg Thr Phe Ile Arg Tyr Ala Met
930                 935                 940

Ala Trp Phe Arg Gln Ala Pro Gly Lys Glu Arg Glu Phe Val Ala Ala
945                 950                 955                 960
```

-continued

Ile Pro Gln Ser Gly Gly Arg Ser Tyr Tyr Ala Asp Ser Val Lys Gly
                965                 970                 975

Arg Phe Thr Ile Ser Arg Asp Asn Ala Lys Asn Thr Val Tyr Leu Gln
                980                 985                 990

Met Asn Ser Leu Lys Pro Glu Asp Thr Ala Val Tyr Ser Cys Ala Ala
                995                 1000                1005

Thr Ser Thr Tyr Tyr Gly Arg Ser Ala Tyr Ser Ser His Ser Gly
    1010                1015                1020

Gly Tyr Asp Tyr Trp Gly Gln Gly Thr Gln Val Thr Val Ser Ser
    1025                1030                1035

Gly Gly Gly Ser Gly Gly Gly Ser Gly Gly Gly Ser Gly Gly Gly
    1040                1045                1050

Ser Gly Gly Ser Gly Gly Gly Ser Glu Ile Thr Arg Thr Thr
    1055                1060                1065

Leu Gln Ser Asp Gln Glu Glu Ile Asp Tyr Asp Asp Thr Ile Ser
    1070                1075                1080

Val Glu Met Lys Lys Glu Asp Phe Asp Ile Phe Asp Glu Asp Glu
    1085                1090                1095

Asn Gln Ser Pro Arg Ser Phe Gln Lys Lys Thr Arg His Tyr Phe
    1100                1105                1110

Ile Ala Ala Val Glu Arg Leu Trp Asp Tyr Gly Met Ser Ser Ser
    1115                1120                1125

Pro His Val Leu Arg Asn Arg Ala Gln Ser Gly Ser Val Pro Gln
    1130                1135                1140

Phe Lys Lys Val Val Phe Gln Glu Phe Thr Asp Gly Ser Phe Thr
    1145                1150                1155

Gln Pro Leu Tyr Arg Gly Glu Leu Asn Glu His Leu Gly Leu Leu
    1160                1165                1170

Gly Pro Tyr Ile Arg Ala Glu Val Glu Asp Asn Ile Met Val Thr
    1175                1180                1185

Phe Arg Asn Gln Ala Ser Arg Pro Tyr Ser Phe Tyr Ser Ser Leu
    1190                1195                1200

Ile Ser Tyr Glu Glu Asp Gln Arg Gln Gly Ala Glu Pro Arg Lys
    1205                1210                1215

Asn Phe Val Lys Pro Asn Glu Thr Lys Thr Tyr Phe Trp Lys Val
    1220                1225                1230

Gln His His Met Ala Pro Thr Lys Asp Glu Phe Asp Cys Lys Ala
    1235                1240                1245

Trp Ala Tyr Phe Ser Asp Val Asp Leu Glu Lys Asp Val His Ser
    1250                1255                1260

Gly Leu Ile Gly Pro Leu Leu Val Cys His Thr Asn Thr Leu Asn
    1265                1270                1275

Pro Ala His Gly Arg Gln Val Thr Val Gln Glu Phe Ala Leu Phe
    1280                1285                1290

Phe Thr Ile Phe Asp Glu Thr Lys Ser Trp Tyr Phe Thr Glu Asn
    1295                1300                1305

Met Glu Arg Asn Cys Arg Ala Pro Cys Asn Ile Gln Met Glu Asp
    1310                1315                1320

Pro Thr Phe Lys Glu Asn Tyr Arg Phe His Ala Ile Asn Gly Tyr
    1325                1330                1335

Ile Met Asp Thr Leu Pro Gly Leu Val Met Ala Gln Asp Gln Arg
    1340                1345                1350

```
Ile Arg Trp Tyr Leu Leu Ser Met Gly Ser Asn Glu Asn Ile His
1355                1360                1365

Ser Ile His Phe Ser Gly His Val Phe Thr Val Arg Lys Lys Glu
1370                1375                1380

Glu Tyr Lys Met Ala Leu Tyr Asn Leu Tyr Pro Gly Val Phe Glu
1385                1390                1395

Thr Val Glu Met Leu Pro Ser Lys Ala Gly Ile Trp Arg Val Glu
1400                1405                1410

Cys Leu Ile Gly Glu His Leu His Ala Gly Met Ser Thr Leu Phe
1415                1420                1425

Leu Val Tyr Ser Asn Lys Cys Gln Thr Pro Leu Gly Met Ala Ser
1430                1435                1440

Gly His Ile Arg Asp Phe Gln Ile Thr Ala Ser Gly Gln Tyr Gly
1445                1450                1455

Gln Trp Ala Pro Lys Leu Ala Arg Leu His Tyr Ser Gly Ser Ile
1460                1465                1470

Asn Ala Trp Ser Thr Lys Glu Pro Phe Ser Trp Ile Lys Val Asp
1475                1480                1485

Leu Leu Ala Pro Met Ile Ile His Gly Ile Lys Thr Gln Gly Ala
1490                1495                1500

Arg Gln Lys Phe Ser Ser Leu Tyr Ile Ser Gln Phe Ile Ile Met
1505                1510                1515

Tyr Ser Leu Asp Gly Lys Lys Trp Gln Thr Tyr Arg Gly Asn Ser
1520                1525                1530

Thr Gly Thr Leu Met Val Phe Phe Gly Asn Val Asp Ser Ser Gly
1535                1540                1545

Ile Lys His Asn Ile Phe Asn Pro Pro Ile Ile Ala Arg Tyr Ile
1550                1555                1560

Arg Leu His Pro Thr His Tyr Ser Ile Arg Ser Thr Leu Arg Met
1565                1570                1575

Glu Trp Met Gly Cys Asp Leu Asn Ser Cys Ser Met Pro Leu Gly
1580                1585                1590

Met Glu Ser Lys Ala Ile Ser Asp Ala Gln Ile Thr Ala Ser Ser
1595                1600                1605

Tyr Phe Thr Asn Met Phe Ala Thr Trp Ser Pro Ser Lys Ala Arg
1610                1615                1620

Leu His Leu Gln Gly Arg Ser Asn Ala Trp Arg Pro Gln Val Asn
1625                1630                1635

Asn Pro Lys Glu Trp Leu Gln Val Asp Phe Gln Lys Thr Met Lys
1640                1645                1650

Val Thr Gly Val Thr Thr Gln Gly Val Lys Ser Leu Leu Thr Ser
1655                1660                1665

Met Tyr Val Lys Glu Phe Leu Ile Ser Ser Ser Gln Asp Gly His
1670                1675                1680

Gln Trp Thr Leu Phe Phe Gln Asn Gly Lys Val Lys Val Phe Gln
1685                1690                1695

Gly Asn Gln Asp Ser Phe Thr Pro Val Val Asn Ser Leu Asp Pro
1700                1705                1710

Pro Leu Leu Thr Arg Tyr Leu Arg Ile His Pro Gln Ser Trp Val
1715                1720                1725
```

His Gln Ile Ala Leu Arg Met Glu Val Leu Gly Cys Glu Ala Gln
    1730                1735                1740

Asp Leu Tyr
    1745

<210> SEQ ID NO 18
<211> LENGTH: 1753
<212> TYPE: PRT
<213> ORGANISM: Artificial
<220> FEATURE:
<223> OTHER INFORMATION: Synthetic FVIII_BD_Cter-0013bv SEQ ID NO: 18

<400> SEQUENCE: 18

Met Gln Ile Glu Leu Ser Thr Cys Phe Phe Leu Cys Leu Leu Arg Phe
1               5                   10                  15

Cys Phe Ser Ala Thr Arg Arg Tyr Tyr Leu Gly Ala Val Glu Leu Ser
            20                  25                  30

Trp Asp Tyr Met Gln Ser Asp Leu Gly Glu Leu Pro Val Asp Ala Arg
        35                  40                  45

Phe Pro Pro Arg Val Pro Lys Ser Phe Pro Phe Asn Thr Ser Val Val
    50                  55                  60

Tyr Lys Lys Thr Leu Phe Val Glu Phe Thr Asp His Leu Phe Asn Ile
65                  70                  75                  80

Ala Lys Pro Arg Pro Pro Trp Met Gly Leu Leu Gly Pro Thr Ile Gln
                85                  90                  95

Ala Glu Val Tyr Asp Thr Val Val Ile Thr Leu Lys Asn Met Ala Ser
            100                 105                 110

His Pro Val Ser Leu His Ala Val Gly Val Ser Tyr Trp Lys Ala Ser
        115                 120                 125

Glu Gly Ala Glu Tyr Asp Asp Gln Thr Ser Gln Arg Glu Lys Glu Asp
    130                 135                 140

Asp Lys Val Phe Pro Gly Gly Ser His Thr Tyr Val Trp Gln Val Leu
145                 150                 155                 160

Lys Glu Asn Gly Pro Met Ala Ser Asp Pro Leu Cys Leu Thr Tyr Ser
                165                 170                 175

Tyr Leu Ser His Val Asp Leu Val Lys Asp Leu Asn Ser Gly Leu Ile
            180                 185                 190

Gly Ala Leu Leu Val Cys Arg Glu Gly Ser Leu Ala Lys Glu Lys Thr
        195                 200                 205

Gln Thr Leu His Lys Phe Ile Leu Leu Phe Ala Val Phe Asp Glu Gly
    210                 215                 220

Lys Ser Trp His Ser Glu Thr Lys Asn Ser Leu Met Gln Asp Arg Asp
225                 230                 235                 240

Ala Ala Ser Ala Arg Ala Trp Pro Lys Met His Thr Val Asn Gly Tyr
                245                 250                 255

Val Asn Arg Ser Leu Pro Gly Leu Ile Gly Cys His Arg Lys Ser Val
            260                 265                 270

Tyr Trp His Val Ile Gly Met Gly Thr Thr Pro Glu Val His Ser Ile
        275                 280                 285

Phe Leu Glu Gly His Thr Phe Leu Val Arg Asn His Arg Gln Ala Ser
    290                 295                 300

Leu Glu Ile Ser Pro Ile Thr Phe Leu Thr Ala Gln Thr Leu Leu Met
305                 310                 315                 320

Asp Leu Gly Gln Phe Leu Leu Phe Cys His Ile Ser Ser His Gln His
                325                 330                 335

```
Asp Gly Met Glu Ala Tyr Val Lys Val Asp Ser Cys Pro Glu Pro
            340                 345                 350

Gln Leu Arg Met Lys Asn Asn Glu Ala Glu Asp Tyr Asp Asp Asp
        355                 360                 365

Leu Thr Asp Ser Glu Met Asp Val Val Arg Phe Asp Asp Asn Ser
    370                 375                 380

Pro Ser Phe Ile Gln Ile Arg Ser Val Ala Lys Lys His Pro Lys Thr
385                 390                 395                 400

Trp Val His Tyr Ile Ala Ala Glu Glu Glu Asp Trp Asp Tyr Ala Pro
                405                 410                 415

Leu Val Leu Ala Pro Asp Asp Arg Ser Tyr Lys Ser Gln Tyr Leu Asn
            420                 425                 430

Asn Gly Pro Gln Arg Ile Gly Arg Lys Tyr Lys Lys Val Arg Phe Met
        435                 440                 445

Ala Tyr Thr Asp Glu Thr Phe Lys Thr Arg Glu Ala Ile Gln His Glu
    450                 455                 460

Ser Gly Ile Leu Gly Pro Leu Leu Tyr Gly Glu Val Gly Asp Thr Leu
465                 470                 475                 480

Leu Ile Ile Phe Lys Asn Gln Ala Ser Arg Pro Tyr Asn Ile Tyr Pro
                485                 490                 495

His Gly Ile Thr Asp Val Arg Pro Leu Tyr Ser Arg Arg Leu Pro Lys
            500                 505                 510

Gly Val Lys His Leu Lys Asp Phe Pro Ile Leu Pro Gly Glu Ile Phe
        515                 520                 525

Lys Tyr Lys Trp Thr Val Thr Val Glu Asp Gly Pro Thr Lys Ser Asp
    530                 535                 540

Pro Arg Cys Leu Thr Arg Tyr Tyr Ser Ser Phe Val Asn Met Glu Arg
545                 550                 555                 560

Asp Leu Ala Ser Gly Leu Ile Gly Pro Leu Leu Ile Cys Tyr Lys Glu
                565                 570                 575

Ser Val Asp Gln Arg Gly Asn Gln Ile Met Ser Asp Lys Arg Asn Val
            580                 585                 590

Ile Leu Phe Ser Val Phe Asp Glu Asn Arg Ser Trp Tyr Leu Thr Glu
        595                 600                 605

Asn Ile Gln Arg Phe Leu Pro Asn Pro Ala Gly Val Gln Leu Glu Asp
    610                 615                 620

Pro Glu Phe Gln Ala Ser Asn Ile Met His Ser Ile Asn Gly Tyr Val
625                 630                 635                 640

Phe Asp Ser Leu Gln Leu Ser Val Cys Leu His Glu Val Ala Tyr Trp
                645                 650                 655

Tyr Ile Leu Ser Ile Gly Ala Gln Thr Asp Phe Leu Ser Val Phe Phe
            660                 665                 670

Ser Gly Tyr Thr Phe Lys His Lys Met Val Tyr Glu Asp Thr Leu Thr
        675                 680                 685

Leu Phe Pro Phe Ser Gly Glu Thr Val Phe Met Ser Met Glu Asn Pro
    690                 695                 700

Gly Leu Trp Ile Leu Gly Cys His Asn Ser Asp Phe Arg Asn Arg Gly
705                 710                 715                 720

Met Thr Ala Leu Leu Lys Val Ser Ser Cys Asp Lys Asn Thr Gly Asp
                725                 730                 735

Tyr Tyr Glu Asp Ser Tyr Glu Asp Ile Ser Ala Tyr Leu Leu Ser Lys
            740                 745                 750
```

```
Asn Asn Ala Ile Glu Pro Arg Ser Phe Ser Gln Asn Pro Val Leu
        755                 760                 765

Lys Arg His Gln Arg Glu Ile Thr Arg Thr Thr Leu Gln Ser Asp Gln
770                 775                 780

Glu Glu Ile Asp Tyr Asp Asp Thr Ile Ser Val Glu Met Lys Lys Glu
785                 790                 795                 800

Asp Phe Asp Ile Tyr Asp Glu Asp Glu Asn Gln Ser Pro Arg Ser Phe
                805                 810                 815

Gln Lys Lys Thr Arg His Tyr Phe Ile Ala Ala Val Glu Arg Leu Trp
            820                 825                 830

Asp Tyr Gly Met Ser Ser Pro His Val Leu Arg Asn Arg Ala Gln
        835                 840                 845

Ser Gly Ser Val Pro Gln Phe Lys Lys Val Val Phe Gln Glu Phe Thr
850                 855                 860

Asp Gly Ser Phe Thr Gln Pro Leu Tyr Arg Gly Glu Leu Asn Glu His
865                 870                 875                 880

Leu Gly Leu Leu Gly Pro Tyr Ile Arg Ala Glu Val Glu Asp Asn Ile
                885                 890                 895

Met Val Thr Phe Arg Asn Gln Ala Ser Arg Pro Tyr Ser Phe Tyr Ser
            900                 905                 910

Ser Leu Ile Ser Tyr Glu Glu Asp Gln Arg Gln Gly Ala Glu Pro Arg
        915                 920                 925

Lys Asn Phe Val Lys Pro Asn Glu Thr Lys Thr Tyr Phe Trp Lys Val
        930                 935                 940

Gln His His Met Ala Pro Thr Lys Asp Glu Phe Asp Cys Lys Ala Trp
945                 950                 955                 960

Ala Tyr Phe Ser Asp Val Asp Leu Glu Lys Asp Val His Ser Gly Leu
                965                 970                 975

Ile Gly Pro Leu Leu Val Cys His Thr Asn Thr Leu Asn Pro Ala His
            980                 985                 990

Gly Arg Gln Val Thr Val Gln Glu Phe Ala Leu Phe Phe Thr Ile Phe
        995                 1000                1005

Asp Glu Thr Lys Ser Trp Tyr Phe Thr Glu Asn Met Glu Arg Asn
   1010                1015                1020

Cys Arg Ala Pro Cys Asn Ile Gln Met Glu Asp Pro Thr Phe Lys
   1025                1030                1035

Glu Asn Tyr Arg Phe His Ala Ile Asn Gly Tyr Ile Met Asp Thr
   1040                1045                1050

Leu Pro Gly Leu Val Met Ala Gln Asp Gln Arg Ile Arg Trp Tyr
   1055                1060                1065

Leu Leu Ser Met Gly Ser Asn Glu Asn Ile His Ser Ile His Phe
   1070                1075                1080

Ser Gly His Val Phe Thr Val Arg Lys Lys Glu Glu Tyr Lys Met
   1085                1090                1095

Ala Leu Tyr Asn Leu Tyr Pro Gly Val Phe Glu Thr Val Glu Met
   1100                1105                1110

Leu Pro Ser Lys Ala Gly Ile Trp Arg Val Glu Cys Leu Ile Gly
   1115                1120                1125

Glu His Leu His Ala Gly Met Ser Thr Leu Phe Leu Val Tyr Ser
   1130                1135                1140

Asn Lys Cys Gln Thr Pro Leu Gly Met Ala Ser Gly His Ile Arg
   1145                1150                1155
```

```
Asp Phe Gln Ile Thr Ala Ser Gly Gln Tyr Gly Gln Trp Ala Pro
    1160                1165                1170

Lys Leu Ala Arg Leu His Tyr Ser Gly Ser Ile Asn Ala Trp Ser
    1175                1180                1185

Thr Lys Glu Pro Phe Ser Trp Ile Lys Val Asp Leu Leu Ala Pro
    1190                1195                1200

Met Ile Ile His Gly Ile Lys Thr Gln Gly Ala Arg Gln Lys Phe
    1205                1210                1215

Ser Ser Leu Tyr Ile Ser Gln Phe Ile Ile Met Tyr Ser Leu Asp
    1220                1225                1230

Gly Lys Lys Trp Gln Thr Tyr Arg Gly Asn Ser Thr Gly Thr Leu
    1235                1240                1245

Met Val Phe Phe Gly Asn Val Asp Ser Ser Gly Ile Lys His Asn
    1250                1255                1260

Ile Phe Asn Pro Pro Ile Ile Ala Arg Tyr Ile Arg Leu His Pro
    1265                1270                1275

Thr His Tyr Ser Ile Arg Ser Thr Leu Arg Met Glu Trp Met Gly
    1280                1285                1290

Cys Asp Leu Asn Ser Cys Ser Met Pro Leu Gly Met Glu Ser Lys
    1295                1300                1305

Ala Ile Ser Asp Ala Gln Ile Thr Ala Ser Ser Tyr Phe Thr Asn
    1310                1315                1320

Met Phe Ala Thr Trp Ser Pro Ser Lys Ala Arg Leu His Leu Gln
    1325                1330                1335

Gly Arg Ser Asn Ala Trp Arg Pro Gln Val Asn Asn Pro Lys Glu
    1340                1345                1350

Trp Leu Gln Val Asp Phe Gln Lys Thr Met Lys Val Thr Gly Val
    1355                1360                1365

Thr Thr Gln Gly Val Lys Ser Leu Leu Thr Ser Met Tyr Val Lys
    1370                1375                1380

Glu Phe Leu Ile Ser Ser Ser Gln Asp Gly His Gln Trp Thr Leu
    1385                1390                1395

Phe Phe Gln Asn Gly Lys Val Lys Val Phe Gln Gly Asn Gln Asp
    1400                1405                1410

Ser Phe Thr Pro Val Val Asn Ser Leu Asp Pro Pro Leu Leu Thr
    1415                1420                1425

Arg Tyr Leu Arg Ile His Pro Gln Ser Trp Val His Gln Ile Ala
    1430                1435                1440

Leu Arg Met Glu Val Leu Gly Cys Glu Ala Gln Asp Leu Tyr Leu
    1445                1450                1455

Thr Pro Arg Gly Val Arg Leu Gly Gly Gly Ser Gly Gly Gly Ser
    1460                1465                1470

Gly Gly Gly Ser Gly Gly Gly Ser Gln Val Gln Leu Val Gln Ser
    1475                1480                1485

Gly Gly Gly Leu Val Gln Ala Gly Asp Ser Leu Arg Leu Ser Cys
    1490                1495                1500

Ala Ala Ser Gly Arg Thr Phe Ile Arg Tyr Ala Met Ala Trp Phe
    1505                1510                1515

Arg Gln Ala Pro Gly Lys Glu Arg Glu Phe Val Ala Ala Ile Pro
    1520                1525                1530

Gln Ser Gly Gly Arg Ser Tyr Tyr Ala Asp Ser Val Lys Gly Arg
    1535                1540                1545
```

```
Phe Thr Ile Ser Arg Asp Asn Ala Lys Asn Thr Val Tyr Leu Gln
    1550                1555                1560

Met Asn Ser Leu Lys Pro Glu Asp Thr Ala Val Tyr Ser Cys Ala
    1565                1570                1575

Ala Thr Ser Thr Tyr Tyr Gly Arg Ser Ala Tyr Ser Ser His Ser
    1580                1585                1590

Gly Gly Tyr Asp Tyr Trp Gly Gln Gly Thr Gln Val Thr Val Ser
    1595                1600                1605

Ser Gly Gly Gly Ser Gly Gly Gly Ser Gly Gly Gly Ser Gly Gly
    1610                1615                1620

Gly Ser Gln Val Gln Leu Val Gln Ser Gly Gly Gly Leu Val Gln
    1625                1630                1635

Ala Gly Asp Ser Leu Arg Leu Ser Cys Ala Ala Ser Gly Arg Thr
    1640                1645                1650

Phe Ile Arg Tyr Ala Met Ala Trp Phe Arg Gln Ala Pro Gly Lys
    1655                1660                1665

Glu Arg Glu Phe Val Ala Ala Ile Pro Gln Ser Gly Gly Arg Ser
    1670                1675                1680

Tyr Tyr Ala Asp Ser Val Lys Gly Arg Phe Thr Ile Ser Arg Asp
    1685                1690                1695

Asn Ala Lys Asn Thr Val Tyr Leu Gln Met Asn Ser Leu Lys Pro
    1700                1705                1710

Glu Asp Thr Ala Val Tyr Ser Cys Ala Ala Thr Ser Thr Tyr Tyr
    1715                1720                1725

Gly Arg Ser Ala Tyr Ser Ser His Ser Gly Gly Tyr Asp Tyr Trp
    1730                1735                1740

Gly Gln Gly Thr Gln Val Thr Val Ser Ser
    1745                1750

<210> SEQ ID NO 19
<211> LENGTH: 1753
<212> TYPE: PRT
<213> ORGANISM: Artificial
<220> FEATURE:
<223> OTHER INFORMATION: Synthetic FVIII_BD_Cter-0013bv_Y1680F SEQ ID
      NO: 19

<400> SEQUENCE: 19

Met Gln Ile Glu Leu Ser Thr Cys Phe Phe Leu Cys Leu Leu Arg Phe
1               5                   10                  15

Cys Phe Ser Ala Thr Arg Arg Tyr Tyr Leu Gly Ala Val Glu Leu Ser
            20                  25                  30

Trp Asp Tyr Met Gln Ser Asp Leu Gly Glu Leu Pro Val Asp Ala Arg
        35                  40                  45

Phe Pro Pro Arg Val Pro Lys Ser Phe Pro Phe Asn Thr Ser Val Val
    50                  55                  60

Tyr Lys Lys Thr Leu Phe Val Glu Phe Thr Asp His Leu Phe Asn Ile
65                  70                  75                  80

Ala Lys Pro Arg Pro Pro Trp Met Gly Leu Leu Gly Pro Thr Ile Gln
                85                  90                  95

Ala Glu Val Tyr Asp Thr Val Val Ile Thr Leu Lys Asn Met Ala Ser
            100                 105                 110

His Pro Val Ser Leu His Ala Val Gly Val Ser Tyr Trp Lys Ala Ser
        115                 120                 125

Glu Gly Ala Glu Tyr Asp Asp Gln Thr Ser Gln Arg Glu Lys Glu Asp
    130                 135                 140
```

```
Asp Lys Val Phe Pro Gly Gly Ser His Thr Tyr Val Trp Gln Val Leu
145                 150                 155                 160

Lys Glu Asn Gly Pro Met Ala Ser Asp Pro Leu Cys Leu Thr Tyr Ser
            165                 170                 175

Tyr Leu Ser His Val Asp Leu Val Lys Asp Leu Asn Ser Gly Leu Ile
        180                 185                 190

Gly Ala Leu Leu Val Cys Arg Glu Gly Ser Leu Ala Lys Glu Lys Thr
        195                 200                 205

Gln Thr Leu His Lys Phe Ile Leu Leu Phe Ala Val Phe Asp Glu Gly
    210                 215                 220

Lys Ser Trp His Ser Glu Thr Lys Asn Ser Leu Met Gln Asp Arg Asp
225                 230                 235                 240

Ala Ala Ser Ala Arg Ala Trp Pro Lys Met His Thr Val Asn Gly Tyr
                245                 250                 255

Val Asn Arg Ser Leu Pro Gly Leu Ile Gly Cys His Arg Lys Ser Val
            260                 265                 270

Tyr Trp His Val Ile Gly Met Gly Thr Thr Pro Glu Val His Ser Ile
        275                 280                 285

Phe Leu Glu Gly His Thr Phe Leu Val Arg Asn His Arg Gln Ala Ser
    290                 295                 300

Leu Glu Ile Ser Pro Ile Thr Phe Leu Thr Ala Gln Thr Leu Leu Met
305                 310                 315                 320

Asp Leu Gly Gln Phe Leu Leu Phe Cys His Ile Ser Ser His Gln His
                325                 330                 335

Asp Gly Met Glu Ala Tyr Val Lys Val Asp Ser Cys Pro Glu Glu Pro
            340                 345                 350

Gln Leu Arg Met Lys Asn Asn Glu Glu Ala Glu Asp Tyr Asp Asp Asp
        355                 360                 365

Leu Thr Asp Ser Glu Met Asp Val Val Arg Phe Asp Asp Asp Asn Ser
370                 375                 380

Pro Ser Phe Ile Gln Ile Arg Ser Val Ala Lys Lys His Pro Lys Thr
385                 390                 395                 400

Trp Val His Tyr Ile Ala Ala Glu Glu Glu Asp Trp Asp Tyr Ala Pro
                405                 410                 415

Leu Val Leu Ala Pro Asp Asp Arg Ser Tyr Lys Ser Gln Tyr Leu Asn
            420                 425                 430

Asn Gly Pro Gln Arg Ile Gly Arg Lys Tyr Lys Lys Val Arg Phe Met
        435                 440                 445

Ala Tyr Thr Asp Glu Thr Phe Lys Thr Arg Glu Ala Ile Gln His Glu
    450                 455                 460

Ser Gly Ile Leu Gly Pro Leu Leu Tyr Gly Glu Val Gly Asp Thr Leu
465                 470                 475                 480

Leu Ile Ile Phe Lys Asn Gln Ala Ser Arg Pro Tyr Asn Ile Tyr Pro
                485                 490                 495

His Gly Ile Thr Asp Val Arg Pro Leu Tyr Ser Arg Arg Leu Pro Lys
            500                 505                 510

Gly Val Lys His Leu Lys Asp Phe Pro Ile Leu Pro Gly Glu Ile Phe
        515                 520                 525

Lys Tyr Lys Trp Thr Val Thr Val Glu Asp Gly Pro Thr Lys Ser Asp
    530                 535                 540

Pro Arg Cys Leu Thr Arg Tyr Tyr Ser Ser Phe Val Asn Met Glu Arg
545                 550                 555                 560
```

```
Asp Leu Ala Ser Gly Leu Ile Gly Pro Leu Ile Cys Tyr Lys Glu
                565                 570                 575
Ser Val Asp Gln Arg Gly Asn Gln Ile Met Ser Asp Lys Arg Asn Val
            580                 585                 590
Ile Leu Phe Ser Val Phe Asp Glu Asn Arg Ser Trp Tyr Leu Thr Glu
            595                 600                 605
Asn Ile Gln Arg Phe Leu Pro Asn Pro Ala Gly Val Gln Leu Glu Asp
            610                 615                 620
Pro Glu Phe Gln Ala Ser Asn Ile Met His Ser Ile Asn Gly Tyr Val
625                 630                 635                 640
Phe Asp Ser Leu Gln Leu Ser Val Cys Leu His Glu Val Ala Tyr Trp
                645                 650                 655
Tyr Ile Leu Ser Ile Gly Ala Gln Thr Asp Phe Leu Ser Val Phe Phe
                660                 665                 670
Ser Gly Tyr Thr Phe Lys His Lys Met Val Tyr Glu Asp Thr Leu Thr
                675                 680                 685
Leu Phe Pro Phe Ser Gly Glu Thr Val Phe Met Ser Met Glu Asn Pro
            690                 695                 700
Gly Leu Trp Ile Leu Gly Cys His Asn Ser Asp Phe Arg Asn Arg Gly
705                 710                 715                 720
Met Thr Ala Leu Leu Lys Val Ser Ser Cys Asp Lys Asn Thr Gly Asp
                725                 730                 735
Tyr Tyr Glu Asp Ser Tyr Glu Asp Ile Ser Ala Tyr Leu Leu Ser Lys
                740                 745                 750
Asn Asn Ala Ile Glu Pro Arg Ser Phe Ser Gln Asn Pro Pro Val Leu
            755                 760                 765
Lys Arg His Gln Arg Glu Ile Thr Arg Thr Thr Leu Gln Ser Asp Gln
            770                 775                 780
Glu Glu Ile Asp Tyr Asp Asp Thr Ile Ser Val Glu Met Lys Lys Glu
785                 790                 795                 800
Asp Phe Asp Ile Phe Asp Glu Asp Glu Asn Gln Ser Pro Arg Ser Phe
                805                 810                 815
Gln Lys Lys Thr Arg His Tyr Phe Ile Ala Ala Val Glu Arg Leu Trp
            820                 825                 830
Asp Tyr Gly Met Ser Ser Ser Pro His Val Leu Arg Asn Arg Ala Gln
            835                 840                 845
Ser Gly Ser Val Pro Gln Phe Lys Lys Val Val Phe Gln Glu Phe Thr
            850                 855                 860
Asp Gly Ser Phe Thr Gln Pro Leu Tyr Arg Gly Glu Leu Asn Glu His
865                 870                 875                 880
Leu Gly Leu Leu Gly Pro Tyr Ile Arg Ala Glu Val Glu Asp Asn Ile
                885                 890                 895
Met Val Thr Phe Arg Asn Gln Ala Ser Arg Pro Tyr Ser Phe Tyr Ser
                900                 905                 910
Ser Leu Ile Ser Tyr Glu Glu Asp Gln Arg Gln Gly Ala Glu Pro Arg
            915                 920                 925
Lys Asn Phe Val Lys Pro Asn Glu Thr Lys Thr Tyr Phe Trp Lys Val
            930                 935                 940
Gln His His Met Ala Pro Thr Lys Asp Glu Phe Asp Cys Lys Ala Trp
945                 950                 955                 960
Ala Tyr Phe Ser Asp Val Asp Leu Glu Lys Asp Val His Ser Gly Leu
                965                 970                 975
```

```
Ile Gly Pro Leu Leu Val Cys His Thr Asn Thr Leu Asn Pro Ala His
            980                 985                 990

Gly Arg Gln Val Thr Val Gln Glu Phe Ala Leu Phe Phe Thr Ile Phe
            995                1000                1005

Asp Glu Thr Lys Ser Trp Tyr Phe Thr Glu Asn Met Glu Arg Asn
        1010                1015                1020

Cys Arg Ala Pro Cys Asn Ile Gln Met Glu Asp Pro Thr Phe Lys
        1025                1030                1035

Glu Asn Tyr Arg Phe His Ala Ile Asn Gly Tyr Ile Met Asp Thr
        1040                1045                1050

Leu Pro Gly Leu Val Met Ala Gln Asp Gln Arg Ile Arg Trp Tyr
        1055                1060                1065

Leu Leu Ser Met Gly Ser Asn Glu Asn Ile His Ser Ile His Phe
        1070                1075                1080

Ser Gly His Val Phe Thr Val Arg Lys Lys Glu Glu Tyr Lys Met
        1085                1090                1095

Ala Leu Tyr Asn Leu Tyr Pro Gly Val Phe Glu Thr Val Glu Met
        1100                1105                1110

Leu Pro Ser Lys Ala Gly Ile Trp Arg Val Glu Cys Leu Ile Gly
        1115                1120                1125

Glu His Leu His Ala Gly Met Ser Thr Leu Phe Leu Val Tyr Ser
        1130                1135                1140

Asn Lys Cys Gln Thr Pro Leu Gly Met Ala Ser Gly His Ile Arg
        1145                1150                1155

Asp Phe Gln Ile Thr Ala Ser Gly Gln Tyr Gly Gln Trp Ala Pro
        1160                1165                1170

Lys Leu Ala Arg Leu His Tyr Ser Gly Ser Ile Asn Ala Trp Ser
        1175                1180                1185

Thr Lys Glu Pro Phe Ser Trp Ile Lys Val Asp Leu Leu Ala Pro
        1190                1195                1200

Met Ile Ile His Gly Ile Lys Thr Gln Gly Ala Arg Gln Lys Phe
        1205                1210                1215

Ser Ser Leu Tyr Ile Ser Gln Phe Ile Ile Met Tyr Ser Leu Asp
        1220                1225                1230

Gly Lys Lys Trp Gln Thr Tyr Arg Gly Asn Ser Thr Gly Thr Leu
        1235                1240                1245

Met Val Phe Phe Gly Asn Val Asp Ser Ser Gly Ile Lys His Asn
        1250                1255                1260

Ile Phe Asn Pro Pro Ile Ile Ala Arg Tyr Ile Arg Leu His Pro
        1265                1270                1275

Thr His Tyr Ser Ile Arg Ser Thr Leu Arg Met Glu Trp Met Gly
        1280                1285                1290

Cys Asp Leu Asn Ser Cys Ser Met Pro Leu Gly Met Glu Ser Lys
        1295                1300                1305

Ala Ile Ser Asp Ala Gln Ile Thr Ala Ser Ser Tyr Phe Thr Asn
        1310                1315                1320

Met Phe Ala Thr Trp Ser Pro Ser Lys Ala Arg Leu His Leu Gln
        1325                1330                1335

Gly Arg Ser Asn Ala Trp Arg Pro Gln Val Asn Asn Pro Lys Glu
        1340                1345                1350

Trp Leu Gln Val Asp Phe Gln Lys Thr Met Lys Val Thr Gly Val
        1355                1360                1365
```

```
Thr Thr Gln Gly Val Lys Ser Leu Leu Thr Ser Met Tyr Val Lys
    1370            1375            1380

Glu Phe Leu Ile Ser Ser Gln Asp Gly His Gln Trp Thr Leu
1385            1390            1395

Phe Phe Gln Asn Gly Lys Val Lys Val Phe Gln Gly Asn Gln Asp
1400            1405            1410

Ser Phe Thr Pro Val Val Asn Ser Leu Asp Pro Pro Leu Leu Thr
    1415            1420            1425

Arg Tyr Leu Arg Ile His Pro Gln Ser Trp Val His Gln Ile Ala
    1430            1435            1440

Leu Arg Met Glu Val Leu Gly Cys Glu Ala Gln Asp Leu Tyr Leu
    1445            1450            1455

Thr Pro Arg Gly Val Arg Leu Gly Gly Gly Ser Gly Gly Gly Ser
    1460            1465            1470

Gly Gly Gly Ser Gly Gly Gly Ser Gln Val Gln Leu Val Gln Ser
    1475            1480            1485

Gly Gly Gly Leu Val Gln Ala Gly Asp Ser Leu Arg Leu Ser Cys
    1490            1495            1500

Ala Ala Ser Gly Arg Thr Phe Ile Arg Tyr Ala Met Ala Trp Phe
    1505            1510            1515

Arg Gln Ala Pro Gly Lys Glu Arg Glu Phe Val Ala Ala Ile Pro
    1520            1525            1530

Gln Ser Gly Gly Arg Ser Tyr Tyr Ala Asp Ser Val Lys Gly Arg
    1535            1540            1545

Phe Thr Ile Ser Arg Asp Asn Ala Lys Asn Thr Val Tyr Leu Gln
    1550            1555            1560

Met Asn Ser Leu Lys Pro Glu Asp Thr Ala Val Tyr Ser Cys Ala
    1565            1570            1575

Ala Thr Ser Thr Tyr Tyr Gly Arg Ser Ala Tyr Ser Ser His Ser
    1580            1585            1590

Gly Gly Tyr Asp Tyr Trp Gly Gln Gly Thr Gln Val Thr Val Ser
    1595            1600            1605

Ser Gly Gly Gly Ser Gly Gly Gly Ser Gly Gly Gly Ser Gly Gly
    1610            1615            1620

Gly Ser Gln Val Gln Leu Val Gln Ser Gly Gly Gly Leu Val Gln
    1625            1630            1635

Ala Gly Asp Ser Leu Arg Leu Ser Cys Ala Ala Ser Gly Arg Thr
    1640            1645            1650

Phe Ile Arg Tyr Ala Met Ala Trp Phe Arg Gln Ala Pro Gly Lys
    1655            1660            1665

Glu Arg Glu Phe Val Ala Ala Ile Pro Gln Ser Gly Gly Arg Ser
    1670            1675            1680

Tyr Tyr Ala Asp Ser Val Lys Gly Arg Phe Thr Ile Ser Arg Asp
    1685            1690            1695

Asn Ala Lys Asn Thr Val Tyr Leu Gln Met Asn Ser Leu Lys Pro
    1700            1705            1710

Glu Asp Thr Ala Val Tyr Ser Cys Ala Ala Thr Ser Thr Tyr Tyr
    1715            1720            1725

Gly Arg Ser Ala Tyr Ser Ser His Ser Gly Gly Tyr Asp Tyr Trp
    1730            1735            1740

Gly Gln Gly Thr Gln Val Thr Val Ser Ser
    1745            1750
```

<210> SEQ ID NO 20
<211> LENGTH: 2022
<212> TYPE: PRT
<213> ORGANISM: Artificial
<220> FEATURE:
<223> OTHER INFORMATION: Synthetic FVIII_KB0013bv_Cter-0013bv SEQ ID NO: 20

<400> SEQUENCE: 20

```
Met Gln Ile Glu Leu Ser Thr Cys Phe Phe Leu Cys Leu Leu Arg Phe
1               5                   10                  15

Cys Phe Ser Ala Thr Arg Arg Tyr Tyr Leu Gly Ala Val Glu Leu Ser
            20                  25                  30

Trp Asp Tyr Met Gln Ser Asp Leu Gly Glu Leu Pro Val Asp Ala Arg
        35                  40                  45

Phe Pro Pro Arg Val Pro Lys Ser Phe Pro Phe Asn Thr Ser Val Val
    50                  55                  60

Tyr Lys Lys Thr Leu Phe Val Glu Phe Thr Asp His Leu Phe Asn Ile
65                  70                  75                  80

Ala Lys Pro Arg Pro Pro Trp Met Gly Leu Leu Gly Pro Thr Ile Gln
                85                  90                  95

Ala Glu Val Tyr Asp Thr Val Val Ile Thr Leu Lys Asn Met Ala Ser
            100                 105                 110

His Pro Val Ser Leu His Ala Val Gly Val Ser Tyr Trp Lys Ala Ser
        115                 120                 125

Glu Gly Ala Glu Tyr Asp Asp Gln Thr Ser Gln Arg Glu Lys Glu Asp
    130                 135                 140

Asp Lys Val Phe Pro Gly Gly Ser His Thr Tyr Val Trp Gln Val Leu
145                 150                 155                 160

Lys Glu Asn Gly Pro Met Ala Ser Asp Pro Leu Cys Leu Thr Tyr Ser
                165                 170                 175

Tyr Leu Ser His Val Asp Leu Val Lys Asp Leu Asn Ser Gly Leu Ile
            180                 185                 190

Gly Ala Leu Leu Val Cys Arg Glu Gly Ser Leu Ala Lys Glu Lys Thr
        195                 200                 205

Gln Thr Leu His Lys Phe Ile Leu Leu Phe Ala Val Phe Asp Glu Gly
    210                 215                 220

Lys Ser Trp His Ser Glu Thr Lys Asn Ser Leu Met Gln Asp Arg Asp
225                 230                 235                 240

Ala Ala Ser Ala Arg Ala Trp Pro Lys Met His Thr Val Asn Gly Tyr
                245                 250                 255

Val Asn Arg Ser Leu Pro Gly Leu Ile Gly Cys His Arg Lys Ser Val
            260                 265                 270

Tyr Trp His Val Ile Gly Met Gly Thr Thr Pro Glu Val His Ser Ile
        275                 280                 285

Phe Leu Glu Gly His Thr Phe Leu Val Arg Asn His Arg Gln Ala Ser
    290                 295                 300

Leu Glu Ile Ser Pro Ile Thr Phe Leu Thr Ala Gln Thr Leu Leu Met
305                 310                 315                 320

Asp Leu Gly Gln Phe Leu Leu Phe Cys His Ile Ser Ser His Gln His
                325                 330                 335

Asp Gly Met Glu Ala Tyr Val Lys Val Asp Ser Cys Pro Glu Glu Pro
            340                 345                 350

Gln Leu Arg Met Lys Asn Asn Glu Glu Ala Glu Asp Tyr Asp Asp Asp
        355                 360                 365
```

```
Leu Thr Asp Ser Glu Met Asp Val Val Arg Phe Asp Asp Asn Ser
    370             375                 380

Pro Ser Phe Ile Gln Ile Arg Ser Val Ala Lys Lys His Pro Lys Thr
385             390                 395                 400

Trp Val His Tyr Ile Ala Ala Glu Glu Asp Trp Asp Tyr Ala Pro
                405                 410                 415

Leu Val Leu Ala Pro Asp Asp Arg Ser Tyr Lys Ser Gln Tyr Leu Asn
            420                 425                 430

Asn Gly Pro Gln Arg Ile Gly Arg Lys Tyr Lys Val Arg Phe Met
            435                 440                 445

Ala Tyr Thr Asp Glu Thr Phe Lys Thr Arg Glu Ala Ile Gln His Glu
    450                 455                 460

Ser Gly Ile Leu Gly Pro Leu Leu Tyr Gly Glu Val Gly Asp Thr Leu
465             470                 475                 480

Leu Ile Ile Phe Lys Asn Gln Ala Ser Arg Pro Tyr Asn Ile Tyr Pro
                485                 490                 495

His Gly Ile Thr Asp Val Arg Pro Leu Tyr Ser Arg Arg Leu Pro Lys
                500                 505                 510

Gly Val Lys His Leu Lys Asp Phe Pro Ile Leu Pro Gly Glu Ile Phe
                515                 520                 525

Lys Tyr Lys Trp Thr Val Thr Val Glu Asp Gly Pro Thr Lys Ser Asp
    530                 535                 540

Pro Arg Cys Leu Thr Arg Tyr Tyr Ser Ser Phe Val Asn Met Glu Arg
545                 550                 555                 560

Asp Leu Ala Ser Gly Leu Ile Gly Pro Leu Leu Ile Cys Tyr Lys Glu
                565                 570                 575

Ser Val Asp Gln Arg Gly Asn Gln Ile Met Ser Asp Lys Arg Asn Val
                580                 585                 590

Ile Leu Phe Ser Val Phe Asp Glu Asn Arg Ser Trp Tyr Leu Thr Glu
                595                 600                 605

Asn Ile Gln Arg Phe Leu Pro Asn Pro Ala Gly Val Gln Leu Glu Asp
    610                 615                 620

Pro Glu Phe Gln Ala Ser Asn Ile Met His Ser Ile Asn Gly Tyr Val
625                 630                 635                 640

Phe Asp Ser Leu Gln Leu Ser Val Cys Leu His Glu Val Ala Tyr Trp
                645                 650                 655

Tyr Ile Leu Ser Ile Gly Ala Gln Thr Asp Phe Leu Ser Val Phe Phe
                660                 665                 670

Ser Gly Tyr Thr Phe Lys His Lys Met Val Tyr Glu Asp Thr Leu Thr
                675                 680                 685

Leu Phe Pro Phe Ser Gly Glu Thr Val Phe Met Ser Met Glu Asn Pro
    690                 695                 700

Gly Leu Trp Ile Leu Gly Cys His Asn Ser Asp Phe Arg Asn Arg Gly
705                 710                 715                 720

Met Thr Ala Leu Leu Lys Val Ser Ser Cys Asp Lys Asn Thr Gly Asp
                725                 730                 735

Tyr Tyr Glu Asp Ser Tyr Glu Asp Ile Ser Ala Tyr Leu Leu Ser Lys
                740                 745                 750

Asn Asn Ala Ile Glu Pro Arg Ser Phe Ser Gly Gly Ser Gln Val
            755                 760                 765

Gln Leu Val Gln Ser Gly Gly Gly Leu Val Gln Ala Gly Asp Ser Leu
    770                 775                 780
```

-continued

```
Arg Leu Ser Cys Ala Ala Ser Gly Arg Thr Phe Ile Arg Tyr Ala Met
785                 790                 795                 800

Ala Trp Phe Arg Gln Ala Pro Gly Lys Glu Arg Glu Phe Val Ala Ala
            805                 810                 815

Ile Pro Gln Ser Gly Gly Arg Ser Tyr Tyr Ala Asp Ser Val Lys Gly
            820                 825                 830

Arg Phe Thr Ile Ser Arg Asp Asn Ala Lys Asn Thr Val Tyr Leu Gln
            835                 840                 845

Met Asn Ser Leu Lys Pro Glu Asp Thr Ala Val Tyr Ser Cys Ala Ala
850                 855                 860

Thr Ser Thr Tyr Tyr Gly Arg Ser Ala Tyr Ser Ser His Ser Gly Gly
865                 870                 875                 880

Tyr Asp Tyr Trp Gly Gln Gly Thr Gln Val Thr Val Ser Ser Gly Gly
                885                 890                 895

Gly Ser Gly Gly Gly Ser Gly Gly Ser Gly Gly Gly Ser Gln Val
            900                 905                 910

Gln Leu Val Gln Ser Gly Gly Gly Leu Val Gln Ala Gly Asp Ser Leu
            915                 920                 925

Arg Leu Ser Cys Ala Ala Ser Gly Arg Thr Phe Ile Arg Tyr Ala Met
930                 935                 940

Ala Trp Phe Arg Gln Ala Pro Gly Lys Glu Arg Glu Phe Val Ala Ala
945                 950                 955                 960

Ile Pro Gln Ser Gly Gly Arg Ser Tyr Tyr Ala Asp Ser Val Lys Gly
            965                 970                 975

Arg Phe Thr Ile Ser Arg Asp Asn Ala Lys Asn Thr Val Tyr Leu Gln
            980                 985                 990

Met Asn Ser Leu Lys Pro Glu Asp  Thr Ala Val Tyr Ser  Cys Ala Ala
            995                 1000                 1005

Thr  Ser  Thr  Tyr  Tyr  Gly  Arg   Ser  Ala  Tyr  Ser   Ser  His  Ser  Gly
    1010                    1015                   1020

Gly  Tyr  Asp  Tyr  Trp  Gly  Gln   Gly  Thr  Gln  Val   Thr  Val  Ser  Ser
    1025                    1030                   1035

Gly  Gly  Gly  Ser  Glu  Ile  Thr   Arg  Thr  Thr  Leu   Gln  Ser  Asp  Gln
    1040                    1045                   1050

Glu  Glu  Ile  Asp  Tyr  Asp  Asp   Thr  Ile  Ser  Val   Glu  Met  Lys  Lys
    1055                    1060                   1065

Glu  Asp  Phe  Asp  Ile  Tyr  Glu   Asp  Glu  Asn  Gln   Ser  Pro  Arg
    1070                    1075                   1080

Ser  Phe  Gln  Lys  Lys  Thr  Arg   His  Tyr  Phe  Ile   Ala  Ala  Val  Glu
    1085                    1090                   1095

Arg  Leu  Trp  Asp  Tyr  Gly  Met   Ser  Ser  Ser  Pro   His  Val  Leu  Arg
    1100                    1105                   1110

Asn  Arg  Ala  Gln  Ser  Gly  Ser   Val  Pro  Gln  Phe   Lys  Lys  Val  Val
    1115                    1120                   1125

Phe  Gln  Glu  Phe  Thr  Asp  Gly   Ser  Phe  Thr  Gln   Pro  Leu  Tyr  Arg
    1130                    1135                   1140

Gly  Glu  Leu  Asn  Glu  His  Leu   Gly  Leu  Leu  Gly   Pro  Tyr  Ile  Arg
    1145                    1150                   1155

Ala  Glu  Val  Glu  Asp  Asn  Ile   Met  Val  Thr  Phe   Arg  Asn  Gln  Ala
    1160                    1165                   1170

Ser  Arg  Pro  Tyr  Ser  Phe  Tyr   Ser  Ser  Leu  Ile   Ser  Tyr  Glu  Glu
    1175                    1180                   1185
```

-continued

```
Asp Gln Arg Gln Gly Ala Glu Pro Arg Lys Asn Phe Val Lys Pro
1190                1195                1200

Asn Glu Thr Lys Thr Tyr Phe Trp Lys Val Gln His His Met Ala
    1205                1210                1215

Pro Thr Lys Asp Glu Phe Asp Cys Lys Ala Trp Ala Tyr Phe Ser
1220                1225                1230

Asp Val Asp Leu Glu Lys Asp Val His Ser Gly Leu Ile Gly Pro
1235                1240                1245

Leu Leu Val Cys His Thr Asn Thr Leu Asn Pro Ala His Gly Arg
1250                1255                1260

Gln Val Thr Val Gln Glu Phe Ala Leu Phe Phe Thr Ile Phe Asp
1265                1270                1275

Glu Thr Lys Ser Trp Tyr Phe Thr Glu Asn Met Glu Arg Asn Cys
1280                1285                1290

Arg Ala Pro Cys Asn Ile Gln Met Glu Asp Pro Thr Phe Lys Glu
    1295                1300                1305

Asn Tyr Arg Phe His Ala Ile Asn Gly Tyr Ile Met Asp Thr Leu
1310                1315                1320

Pro Gly Leu Val Met Ala Gln Asp Gln Arg Ile Arg Trp Tyr Leu
1325                1330                1335

Leu Ser Met Gly Ser Asn Glu Asn Ile His Ser Ile His Phe Ser
1340                1345                1350

Gly His Val Phe Thr Val Arg Lys Lys Glu Glu Tyr Lys Met Ala
1355                1360                1365

Leu Tyr Asn Leu Tyr Pro Gly Val Phe Glu Thr Val Glu Met Leu
1370                1375                1380

Pro Ser Lys Ala Gly Ile Trp Arg Val Glu Cys Leu Ile Gly Glu
1385                1390                1395

His Leu His Ala Gly Met Ser Thr Leu Phe Leu Val Tyr Ser Asn
1400                1405                1410

Lys Cys Gln Thr Pro Leu Gly Met Ala Ser Gly His Ile Arg Asp
1415                1420                1425

Phe Gln Ile Thr Ala Ser Gly Gln Tyr Gly Gln Trp Ala Pro Lys
1430                1435                1440

Leu Ala Arg Leu His Tyr Ser Gly Ser Ile Asn Ala Trp Ser Thr
1445                1450                1455

Lys Glu Pro Phe Ser Trp Ile Lys Val Asp Leu Leu Ala Pro Met
1460                1465                1470

Ile Ile His Gly Ile Lys Thr Gln Gly Ala Arg Gln Lys Phe Ser
1475                1480                1485

Ser Leu Tyr Ile Ser Gln Phe Ile Ile Met Tyr Ser Leu Asp Gly
1490                1495                1500

Lys Lys Trp Gln Thr Tyr Arg Gly Asn Ser Thr Gly Thr Leu Met
1505                1510                1515

Val Phe Phe Gly Asn Val Asp Ser Ser Gly Ile Lys His Asn Ile
1520                1525                1530

Phe Asn Pro Pro Ile Ile Ala Arg Tyr Ile Arg Leu His Pro Thr
1535                1540                1545

His Tyr Ser Ile Arg Ser Thr Leu Arg Met Glu Trp Met Gly Cys
1550                1555                1560

Asp Leu Asn Ser Cys Ser Met Pro Leu Gly Met Glu Ser Lys Ala
1565                1570                1575
```

```
Ile Ser Asp Ala Gln Ile Thr Ala Ser Ser Tyr Phe Thr Asn Met
1580               1585               1590

Phe Ala Thr Trp Ser Pro Ser Lys Ala Arg Leu His Leu Gln Gly
1595               1600               1605

Arg Ser Asn Ala Trp Arg Pro Gln Val Asn Asn Pro Lys Glu Trp
1610               1615               1620

Leu Gln Val Asp Phe Gln Lys Thr Met Lys Val Thr Gly Val Thr
1625               1630               1635

Thr Gln Gly Val Lys Ser Leu Leu Thr Ser Met Tyr Val Lys Glu
1640               1645               1650

Phe Leu Ile Ser Ser Ser Gln Asp Gly His Gln Trp Thr Leu Phe
1655               1660               1665

Phe Gln Asn Gly Lys Val Lys Val Phe Gln Gly Asn Gln Asp Ser
1670               1675               1680

Phe Thr Pro Val Val Asn Ser Leu Asp Pro Pro Leu Leu Thr Arg
1685               1690               1695

Tyr Leu Arg Ile His Pro Gln Ser Trp Val His Gln Ile Ala Leu
1700               1705               1710

Arg Met Glu Val Leu Gly Cys Glu Ala Gln Asp Leu Tyr Leu Thr
1715               1720               1725

Pro Arg Gly Val Arg Leu Gly Gly Ser Gly Gly Ser Gly
1730               1735               1740

Gly Gly Ser Gly Gly Gly Ser Gln Val Gln Leu Val Gln Ser Gly
1745               1750               1755

Gly Gly Leu Val Gln Ala Gly Asp Ser Leu Arg Leu Ser Cys Ala
1760               1765               1770

Ala Ser Gly Arg Thr Phe Ile Arg Tyr Ala Met Ala Trp Phe Arg
1775               1780               1785

Gln Ala Pro Gly Lys Glu Arg Glu Phe Val Ala Ala Ile Pro Gln
1790               1795               1800

Ser Gly Gly Arg Ser Tyr Tyr Ala Asp Ser Val Lys Gly Arg Phe
1805               1810               1815

Thr Ile Ser Arg Asp Asn Ala Lys Asn Thr Val Tyr Leu Gln Met
1820               1825               1830

Asn Ser Leu Lys Pro Glu Asp Thr Ala Val Tyr Ser Cys Ala Ala
1835               1840               1845

Thr Ser Thr Tyr Tyr Gly Arg Ser Ala Tyr Ser Ser His Ser Gly
1850               1855               1860

Gly Tyr Asp Tyr Trp Gly Gln Gly Thr Gln Val Thr Val Ser Ser
1865               1870               1875

Gly Gly Gly Ser Gly Gly Gly Ser Gly Gly Gly Ser Gly Gly Gly
1880               1885               1890

Ser Gln Val Gln Leu Val Gln Ser Gly Gly Gly Leu Val Gln Ala
1895               1900               1905

Gly Asp Ser Leu Arg Leu Ser Cys Ala Ala Ser Gly Arg Thr Phe
1910               1915               1920

Ile Arg Tyr Ala Met Ala Trp Phe Arg Gln Ala Pro Gly Lys Glu
1925               1930               1935

Arg Glu Phe Val Ala Ala Ile Pro Gln Ser Gly Gly Arg Ser Tyr
1940               1945               1950

Tyr Ala Asp Ser Val Lys Gly Arg Phe Thr Ile Ser Arg Asp Asn
1955               1960               1965
```

```
Ala Lys Asn Thr Val Tyr Leu Gln Met Asn Ser Leu Lys Pro Glu
    1970                1975                1980

Asp Thr Ala Val Tyr Ser Cys Ala Ala Thr Ser Thr Tyr Tyr Gly
    1985                1990                1995

Arg Ser Ala Tyr Ser Ser His Ser Gly Gly Tyr Asp Tyr Trp Gly
    2000                2005                2010

Gln Gly Thr Gln Val Thr Val Ser Ser
    2015                2020

<210> SEQ ID NO 21
<211> LENGTH: 2022
<212> TYPE: PRT
<213> ORGANISM: Artificial
<220> FEATURE:
<223> OTHER INFORMATION: Synthetic  FVIII_KB0013bv_Cter-0013bv_Y1680F
      SEQ ID NO: 21

<400> SEQUENCE: 21

Met Gln Ile Glu Leu Ser Thr Cys Phe Phe Leu Cys Leu Leu Arg Phe
1               5                   10                  15

Cys Phe Ser Ala Thr Arg Arg Tyr Tyr Leu Gly Ala Val Glu Leu Ser
            20                  25                  30

Trp Asp Tyr Met Gln Ser Asp Leu Gly Glu Leu Pro Val Asp Ala Arg
        35                  40                  45

Phe Pro Pro Arg Val Pro Lys Ser Phe Pro Phe Asn Thr Ser Val Val
50                  55                  60

Tyr Lys Lys Thr Leu Phe Val Glu Phe Thr Asp His Leu Phe Asn Ile
65                  70                  75                  80

Ala Lys Pro Arg Pro Pro Trp Met Gly Leu Leu Gly Pro Thr Ile Gln
                85                  90                  95

Ala Glu Val Tyr Asp Thr Val Val Ile Thr Leu Lys Asn Met Ala Ser
            100                 105                 110

His Pro Val Ser Leu His Ala Val Gly Val Ser Tyr Trp Lys Ala Ser
        115                 120                 125

Glu Gly Ala Glu Tyr Asp Asp Gln Thr Ser Gln Arg Glu Lys Glu Asp
    130                 135                 140

Asp Lys Val Phe Pro Gly Gly Ser His Thr Tyr Val Trp Gln Val Leu
145                 150                 155                 160

Lys Glu Asn Gly Pro Met Ala Ser Asp Pro Leu Cys Leu Thr Tyr Ser
                165                 170                 175

Tyr Leu Ser His Val Asp Leu Val Lys Asp Leu Asn Ser Gly Leu Ile
            180                 185                 190

Gly Ala Leu Leu Val Cys Arg Glu Gly Ser Leu Ala Lys Glu Lys Thr
        195                 200                 205

Gln Thr Leu His Lys Phe Ile Leu Leu Phe Ala Val Phe Asp Glu Gly
    210                 215                 220

Lys Ser Trp His Ser Glu Thr Lys Asn Ser Leu Met Gln Asp Arg Asp
225                 230                 235                 240

Ala Ala Ser Ala Arg Ala Trp Pro Lys Met His Thr Val Asn Gly Tyr
                245                 250                 255

Val Asn Arg Ser Leu Pro Gly Leu Ile Gly Cys His Arg Lys Ser Val
            260                 265                 270

Tyr Trp His Val Ile Gly Met Gly Thr Thr Pro Glu Val His Ser Ile
        275                 280                 285

Phe Leu Glu Gly His Thr Phe Leu Val Arg Asn His Arg Gln Ala Ser
    290                 295                 300
```

```
Leu Glu Ile Ser Pro Ile Thr Phe Leu Thr Ala Gln Thr Leu Leu Met
305                 310                 315                 320

Asp Leu Gly Gln Phe Leu Leu Phe Cys His Ile Ser Ser His Gln His
                    325                 330                 335

Asp Gly Met Glu Ala Tyr Val Lys Val Asp Ser Cys Pro Glu Glu Pro
                340                 345                 350

Gln Leu Arg Met Lys Asn Asn Glu Glu Ala Glu Asp Tyr Asp Asp Asp
                355                 360                 365

Leu Thr Asp Ser Glu Met Asp Val Val Arg Phe Asp Asp Asp Asn Ser
370                 375                 380

Pro Ser Phe Ile Gln Ile Arg Ser Val Ala Lys Lys His Pro Lys Thr
385                 390                 395                 400

Trp Val His Tyr Ile Ala Ala Glu Glu Glu Asp Trp Asp Tyr Ala Pro
                    405                 410                 415

Leu Val Leu Ala Pro Asp Asp Arg Ser Tyr Lys Ser Gln Tyr Leu Asn
                420                 425                 430

Asn Gly Pro Gln Arg Ile Gly Arg Lys Tyr Lys Lys Val Arg Phe Met
                435                 440                 445

Ala Tyr Thr Asp Glu Thr Phe Lys Thr Arg Glu Ala Ile Gln His Glu
    450                 455                 460

Ser Gly Ile Leu Gly Pro Leu Leu Tyr Gly Glu Val Gly Asp Thr Leu
465                 470                 475                 480

Leu Ile Ile Phe Lys Asn Gln Ala Ser Arg Pro Tyr Asn Ile Tyr Pro
                485                 490                 495

His Gly Ile Thr Asp Val Arg Pro Leu Tyr Ser Arg Arg Leu Pro Lys
                500                 505                 510

Gly Val Lys His Leu Lys Asp Phe Pro Ile Leu Pro Gly Glu Ile Phe
                515                 520                 525

Lys Tyr Lys Trp Thr Val Thr Val Glu Asp Gly Pro Thr Lys Ser Asp
530                 535                 540

Pro Arg Cys Leu Thr Arg Tyr Tyr Ser Ser Phe Val Asn Met Glu Arg
545                 550                 555                 560

Asp Leu Ala Ser Gly Leu Ile Gly Pro Leu Leu Ile Cys Tyr Lys Glu
                565                 570                 575

Ser Val Asp Gln Arg Gly Asn Gln Ile Met Ser Asp Lys Arg Asn Val
                580                 585                 590

Ile Leu Phe Ser Val Phe Asp Glu Asn Arg Ser Trp Tyr Leu Thr Glu
                595                 600                 605

Asn Ile Gln Arg Phe Leu Pro Asn Pro Ala Gly Val Gln Leu Glu Asp
                610                 615                 620

Pro Glu Phe Gln Ala Ser Asn Ile Met His Ser Ile Asn Gly Tyr Val
625                 630                 635                 640

Phe Asp Ser Leu Gln Leu Ser Val Cys Leu His Glu Val Ala Tyr Trp
                645                 650                 655

Tyr Ile Leu Ser Ile Gly Ala Gln Thr Asp Phe Leu Ser Val Phe Phe
                660                 665                 670

Ser Gly Tyr Thr Phe Lys His Lys Met Val Tyr Glu Asp Thr Leu Thr
                675                 680                 685

Leu Phe Pro Phe Ser Gly Glu Thr Val Phe Met Ser Met Glu Asn Pro
                690                 695                 700

Gly Leu Trp Ile Leu Gly Cys His Asn Ser Asp Phe Arg Asn Arg Gly
705                 710                 715                 720
```

-continued

Met Thr Ala Leu Leu Lys Val Ser Ser Cys Asp Lys Asn Thr Gly Asp
            725                 730                 735

Tyr Tyr Glu Asp Ser Tyr Glu Asp Ile Ser Ala Tyr Leu Leu Ser Lys
            740                 745                 750

Asn Asn Ala Ile Glu Pro Arg Ser Phe Ser Gly Gly Gly Ser Gln Val
            755                 760                 765

Gln Leu Val Gln Ser Gly Gly Leu Val Gln Ala Gly Asp Ser Leu
            770                 775                 780

Arg Leu Ser Cys Ala Ala Ser Gly Arg Thr Phe Ile Arg Tyr Ala Met
785                 790                 795                 800

Ala Trp Phe Arg Gln Ala Pro Gly Lys Glu Arg Glu Phe Val Ala Ala
                    805                 810                 815

Ile Pro Gln Ser Gly Gly Arg Ser Tyr Tyr Ala Asp Ser Val Lys Gly
            820                 825                 830

Arg Phe Thr Ile Ser Arg Asp Asn Ala Lys Asn Thr Val Tyr Leu Gln
            835                 840                 845

Met Asn Ser Leu Lys Pro Glu Asp Thr Ala Val Tyr Ser Cys Ala Ala
            850                 855                 860

Thr Ser Thr Tyr Tyr Gly Arg Ser Ala Tyr Ser Ser His Ser Gly Gly
865                 870                 875                 880

Tyr Asp Tyr Trp Gly Gln Gly Thr Gln Val Thr Val Ser Ser Gly Gly
                    885                 890                 895

Gly Ser Gly Gly Gly Ser Gly Gly Ser Gly Gly Ser Gln Val
            900                 905                 910

Gln Leu Val Gln Ser Gly Gly Gly Leu Val Gln Ala Gly Asp Ser Leu
            915                 920                 925

Arg Leu Ser Cys Ala Ala Ser Gly Arg Thr Phe Ile Arg Tyr Ala Met
930                 935                 940

Ala Trp Phe Arg Gln Ala Pro Gly Lys Glu Arg Glu Phe Val Ala Ala
945                 950                 955                 960

Ile Pro Gln Ser Gly Gly Arg Ser Tyr Tyr Ala Asp Ser Val Lys Gly
            965                 970                 975

Arg Phe Thr Ile Ser Arg Asp Asn Ala Lys Asn Thr Val Tyr Leu Gln
            980                 985                 990

Met Asn Ser Leu Lys Pro Glu Asp Thr Ala Val Tyr Ser Cys Ala Ala
            995                 1000                1005

Thr Ser Thr Tyr Tyr Gly Arg Ser Ala Tyr Ser Ser His Ser Gly
            1010                1015                1020

Gly Tyr Asp Tyr Trp Gly Gln Gly Thr Gln Val Thr Val Ser Ser
            1025                1030                1035

Gly Gly Gly Ser Glu Ile Thr Arg Thr Thr Leu Gln Ser Asp Gln
            1040                1045                1050

Glu Glu Ile Asp Tyr Asp Asp Thr Ile Ser Val Glu Met Lys Lys
            1055                1060                1065

Glu Asp Phe Asp Ile Phe Asp Glu Asp Glu Asn Gln Ser Pro Arg
            1070                1075                1080

Ser Phe Gln Lys Lys Thr Arg His Tyr Phe Ile Ala Ala Val Glu
            1085                1090                1095

Arg Leu Trp Asp Tyr Gly Met Ser Ser Ser Pro His Val Leu Arg
            1100                1105                1110

Asn Arg Ala Gln Ser Gly Ser Val Pro Gln Phe Lys Lys Val Val
            1115                1120                1125

-continued

Phe Gln Glu Phe Thr Asp Gly Ser Phe Thr Gln Pro Leu Tyr Arg
1130                1135                1140

Gly Glu Leu Asn Glu His Leu Gly Leu Gly Pro Tyr Ile Arg
1145                1150                1155

Ala Glu Val Glu Asp Asn Ile Met Val Thr Phe Arg Asn Gln Ala
1160                1165                1170

Ser Arg Pro Tyr Ser Phe Tyr Ser Ser Leu Ile Ser Tyr Glu Glu
1175                1180                1185

Asp Gln Arg Gln Gly Ala Glu Pro Arg Lys Asn Phe Val Lys Pro
1190                1195                1200

Asn Glu Thr Lys Thr Tyr Phe Trp Lys Val Gln His His Met Ala
1205                1210                1215

Pro Thr Lys Asp Glu Phe Asp Cys Lys Ala Trp Ala Tyr Phe Ser
1220                1225                1230

Asp Val Asp Leu Glu Lys Asp Val His Ser Gly Leu Ile Gly Pro
1235                1240                1245

Leu Leu Val Cys His Thr Asn Thr Leu Asn Pro Ala His Gly Arg
1250                1255                1260

Gln Val Thr Val Gln Glu Phe Ala Leu Phe Phe Thr Ile Phe Asp
1265                1270                1275

Glu Thr Lys Ser Trp Tyr Phe Thr Glu Asn Met Glu Arg Asn Cys
1280                1285                1290

Arg Ala Pro Cys Asn Ile Gln Met Glu Asp Pro Thr Phe Lys Glu
1295                1300                1305

Asn Tyr Arg Phe His Ala Ile Asn Gly Tyr Ile Met Asp Thr Leu
1310                1315                1320

Pro Gly Leu Val Met Ala Gln Asp Gln Arg Ile Arg Trp Tyr Leu
1325                1330                1335

Leu Ser Met Gly Ser Asn Glu Asn Ile His Ser Ile His Phe Ser
1340                1345                1350

Gly His Val Phe Thr Val Arg Lys Lys Glu Glu Tyr Lys Met Ala
1355                1360                1365

Leu Tyr Asn Leu Tyr Pro Gly Val Phe Glu Thr Val Glu Met Leu
1370                1375                1380

Pro Ser Lys Ala Gly Ile Trp Arg Val Glu Cys Leu Ile Gly Glu
1385                1390                1395

His Leu His Ala Gly Met Ser Thr Leu Phe Leu Val Tyr Ser Asn
1400                1405                1410

Lys Cys Gln Thr Pro Leu Gly Met Ala Ser Gly His Ile Arg Asp
1415                1420                1425

Phe Gln Ile Thr Ala Ser Gly Gln Tyr Gly Gln Trp Ala Pro Lys
1430                1435                1440

Leu Ala Arg Leu His Tyr Ser Gly Ser Ile Asn Ala Trp Ser Thr
1445                1450                1455

Lys Glu Pro Phe Ser Trp Ile Lys Val Asp Leu Leu Ala Pro Met
1460                1465                1470

Ile Ile His Gly Ile Lys Thr Gln Gly Ala Arg Gln Lys Phe Ser
1475                1480                1485

Ser Leu Tyr Ile Ser Gln Phe Ile Ile Met Tyr Ser Leu Asp Gly
1490                1495                1500

Lys Lys Trp Gln Thr Tyr Arg Gly Asn Ser Thr Gly Thr Leu Met
1505                1510                1515

```
Val Phe Phe Gly Asn Val Asp Ser Ser Gly Ile Lys His Asn Ile
1520                1525                1530

Phe Asn Pro Pro Ile Ile Ala Arg Tyr Ile Arg Leu His Pro Thr
1535                1540                1545

His Tyr Ser Ile Arg Ser Thr Leu Arg Met Glu Trp Met Gly Cys
1550                1555                1560

Asp Leu Asn Ser Cys Ser Met Pro Leu Gly Met Glu Ser Lys Ala
1565                1570                1575

Ile Ser Asp Ala Gln Ile Thr Ala Ser Ser Tyr Phe Thr Asn Met
1580                1585                1590

Phe Ala Thr Trp Ser Pro Ser Lys Ala Arg Leu His Leu Gln Gly
1595                1600                1605

Arg Ser Asn Ala Trp Arg Pro Gln Val Asn Asn Pro Lys Glu Trp
1610                1615                1620

Leu Gln Val Asp Phe Gln Lys Thr Met Lys Val Thr Gly Val Thr
1625                1630                1635

Thr Gln Gly Val Lys Ser Leu Leu Thr Ser Met Tyr Val Lys Glu
1640                1645                1650

Phe Leu Ile Ser Ser Ser Gln Asp Gly His Gln Trp Thr Leu Phe
1655                1660                1665

Phe Gln Asn Gly Lys Val Lys Val Phe Gln Gly Asn Gln Asp Ser
1670                1675                1680

Phe Thr Pro Val Val Asn Ser Leu Asp Pro Pro Leu Leu Thr Arg
1685                1690                1695

Tyr Leu Arg Ile His Pro Gln Ser Trp Val His Gln Ile Ala Leu
1700                1705                1710

Arg Met Glu Val Leu Gly Cys Glu Ala Gln Asp Leu Tyr Leu Thr
1715                1720                1725

Pro Arg Gly Val Arg Leu Gly Gly Gly Ser Gly Gly Gly Ser Gly
1730                1735                1740

Gly Gly Ser Gly Gly Gly Ser Gln Val Gln Leu Val Gln Ser Gly
1745                1750                1755

Gly Gly Leu Val Gln Ala Gly Asp Ser Leu Arg Leu Ser Cys Ala
1760                1765                1770

Ala Ser Gly Arg Thr Phe Ile Arg Tyr Ala Met Ala Trp Phe Arg
1775                1780                1785

Gln Ala Pro Gly Lys Glu Arg Glu Phe Val Ala Ala Ile Pro Gln
1790                1795                1800

Ser Gly Gly Arg Ser Tyr Tyr Ala Asp Ser Val Lys Gly Arg Phe
1805                1810                1815

Thr Ile Ser Arg Asp Asn Ala Lys Asn Thr Val Tyr Leu Gln Met
1820                1825                1830

Asn Ser Leu Lys Pro Glu Asp Thr Ala Val Tyr Ser Cys Ala Ala
1835                1840                1845

Thr Ser Thr Tyr Tyr Gly Arg Ser Ala Tyr Ser Ser His Ser Gly
1850                1855                1860

Gly Tyr Asp Tyr Trp Gly Gln Gly Thr Gln Val Thr Val Ser Ser
1865                1870                1875

Gly Gly Gly Ser Gly Gly Gly Ser Gly Gly Gly Ser Gly Gly Gly
1880                1885                1890

Ser Gln Val Gln Leu Val Gln Ser Gly Gly Gly Leu Val Gln Ala
1895                1900                1905
```

-continued

```
Gly Asp Ser Leu Arg Leu Ser Cys Ala Ala Ser Gly Arg Thr Phe
    1910            1915                1920

Ile Arg Tyr Ala Met Ala Trp Phe Arg Gln Ala Pro Gly Lys Glu
    1925            1930                1935

Arg Glu Phe Val Ala Ala Ile Pro Gln Ser Gly Gly Arg Ser Tyr
    1940            1945                1950

Tyr Ala Asp Ser Val Lys Gly Arg Phe Thr Ile Ser Arg Asp Asn
    1955            1960                1965

Ala Lys Asn Thr Val Tyr Leu Gln Met Asn Ser Leu Lys Pro Glu
    1970            1975                1980

Asp Thr Ala Val Tyr Ser Cys Ala Ala Thr Ser Thr Tyr Tyr Gly
    1985            1990                1995

Arg Ser Ala Tyr Ser Ser His Ser Gly Gly Tyr Asp Tyr Trp Gly
    2000            2005                2010

Gln Gly Thr Gln Val Thr Val Ser Ser
    2015            2020

<210> SEQ ID NO 22
<211> LENGTH: 2042
<212> TYPE: PRT
<213> ORGANISM: Artificial
<220> FEATURE:
<223> OTHER INFORMATION: Synthetic FVIII_KB0013bv(6GGGS)_Cter-0013bv SEQ
      ID NO: 22

<400> SEQUENCE: 22

Met Gln Ile Glu Leu Ser Thr Cys Phe Phe Leu Cys Leu Leu Arg Phe
1               5                   10                  15

Cys Phe Ser Ala Thr Arg Arg Tyr Tyr Leu Gly Ala Val Glu Leu Ser
                20                  25                  30

Trp Asp Tyr Met Gln Ser Asp Leu Gly Glu Leu Pro Val Asp Ala Arg
            35                  40                  45

Phe Pro Pro Arg Val Pro Lys Ser Phe Pro Phe Asn Thr Ser Val Val
    50                  55                  60

Tyr Lys Lys Thr Leu Phe Val Glu Phe Thr Asp His Leu Phe Asn Ile
65                  70                  75                  80

Ala Lys Pro Arg Pro Pro Trp Met Gly Leu Leu Gly Pro Thr Ile Gln
                85                  90                  95

Ala Glu Val Tyr Asp Thr Val Val Ile Thr Leu Lys Asn Met Ala Ser
                100                 105                 110

His Pro Val Ser Leu His Ala Val Gly Val Ser Tyr Trp Lys Ala Ser
            115                 120                 125

Glu Gly Ala Glu Tyr Asp Asp Gln Thr Ser Gln Arg Glu Lys Glu Asp
    130                 135                 140

Asp Lys Val Phe Pro Gly Gly Ser His Thr Tyr Val Trp Gln Val Leu
145                 150                 155                 160

Lys Glu Asn Gly Pro Met Ala Ser Asp Pro Leu Cys Leu Thr Tyr Ser
                165                 170                 175

Tyr Leu Ser His Val Asp Leu Val Lys Asp Leu Asn Ser Gly Leu Ile
            180                 185                 190

Gly Ala Leu Leu Val Cys Arg Glu Gly Ser Leu Ala Lys Glu Lys Thr
    195                 200                 205

Gln Thr Leu His Lys Phe Ile Leu Leu Phe Ala Val Phe Asp Glu Gly
    210                 215                 220
```

```
Lys Ser Trp His Ser Glu Thr Lys Asn Ser Leu Met Gln Asp Arg Asp
225                 230                 235                 240

Ala Ala Ser Ala Arg Ala Trp Pro Lys Met His Thr Val Asn Gly Tyr
                245                 250                 255

Val Asn Arg Ser Leu Pro Gly Leu Ile Gly Cys His Arg Lys Ser Val
            260                 265                 270

Tyr Trp His Val Ile Gly Met Gly Thr Thr Pro Glu Val His Ser Ile
        275                 280                 285

Phe Leu Glu Gly His Thr Phe Leu Val Arg Asn His Arg Gln Ala Ser
    290                 295                 300

Leu Glu Ile Ser Pro Ile Thr Phe Leu Thr Ala Gln Thr Leu Leu Met
305                 310                 315                 320

Asp Leu Gly Gln Phe Leu Leu Phe Cys His Ile Ser Ser His Gln His
                325                 330                 335

Asp Gly Met Glu Ala Tyr Val Lys Val Asp Ser Cys Pro Glu Glu Pro
            340                 345                 350

Gln Leu Arg Met Lys Asn Asn Glu Glu Ala Glu Asp Tyr Asp Asp Asp
        355                 360                 365

Leu Thr Asp Ser Glu Met Asp Val Val Arg Phe Asp Asp Asp Asn Ser
    370                 375                 380

Pro Ser Phe Ile Gln Ile Arg Ser Val Ala Lys Lys His Pro Lys Thr
385                 390                 395                 400

Trp Val His Tyr Ile Ala Ala Glu Glu Glu Asp Trp Asp Tyr Ala Pro
                405                 410                 415

Leu Val Leu Ala Pro Asp Asp Arg Ser Tyr Lys Ser Gln Tyr Leu Asn
            420                 425                 430

Asn Gly Pro Gln Arg Ile Gly Arg Lys Tyr Lys Lys Val Arg Phe Met
        435                 440                 445

Ala Tyr Thr Asp Glu Thr Phe Lys Thr Arg Glu Ala Ile Gln His Glu
    450                 455                 460

Ser Gly Ile Leu Gly Pro Leu Leu Tyr Gly Glu Val Gly Asp Thr Leu
465                 470                 475                 480

Leu Ile Ile Phe Lys Asn Gln Ala Ser Arg Pro Tyr Asn Ile Tyr Pro
                485                 490                 495

His Gly Ile Thr Asp Val Arg Pro Leu Tyr Ser Arg Arg Leu Pro Lys
            500                 505                 510

Gly Val Lys His Leu Lys Asp Phe Pro Ile Leu Pro Gly Glu Ile Phe
        515                 520                 525

Lys Tyr Lys Trp Thr Val Thr Val Glu Asp Gly Pro Thr Lys Ser Asp
    530                 535                 540

Pro Arg Cys Leu Thr Arg Tyr Tyr Ser Ser Phe Val Asn Met Glu Arg
545                 550                 555                 560

Asp Leu Ala Ser Gly Leu Ile Gly Pro Leu Leu Ile Cys Tyr Lys Glu
                565                 570                 575

Ser Val Asp Gln Arg Gly Asn Gln Ile Met Ser Asp Lys Arg Asn Val
            580                 585                 590

Ile Leu Phe Ser Val Phe Asp Glu Asn Arg Ser Trp Tyr Leu Thr Glu
        595                 600                 605

Asn Ile Gln Arg Phe Leu Pro Asn Pro Ala Gly Val Gln Leu Glu Asp
    610                 615                 620

Pro Glu Phe Gln Ala Ser Asn Ile Met His Ser Ile Asn Gly Tyr Val
625                 630                 635                 640
```

```
Phe Asp Ser Leu Gln Leu Ser Val Cys Leu His Glu Val Ala Tyr Trp
                645                 650                 655

Tyr Ile Leu Ser Ile Gly Ala Gln Thr Asp Phe Leu Ser Val Phe Phe
            660                 665                 670

Ser Gly Tyr Thr Phe Lys His Lys Met Val Tyr Glu Asp Thr Leu Thr
        675                 680                 685

Leu Phe Pro Phe Ser Gly Glu Thr Val Phe Met Ser Met Glu Asn Pro
    690                 695                 700

Gly Leu Trp Ile Leu Gly Cys His Asn Ser Asp Phe Arg Asn Arg Gly
705                 710                 715                 720

Met Thr Ala Leu Leu Lys Val Ser Ser Cys Asp Lys Asn Thr Gly Asp
                725                 730                 735

Tyr Tyr Glu Asp Ser Tyr Glu Asp Ile Ser Ala Tyr Leu Leu Ser Lys
            740                 745                 750

Asn Asn Ala Ile Glu Pro Arg Ser Phe Ser Gly Gly Gly Ser Gln Val
        755                 760                 765

Gln Leu Val Gln Ser Gly Gly Gly Leu Val Gln Ala Gly Asp Ser Leu
    770                 775                 780

Arg Leu Ser Cys Ala Ala Ser Gly Arg Thr Phe Ile Arg Tyr Ala Met
785                 790                 795                 800

Ala Trp Phe Arg Gln Ala Pro Gly Lys Glu Arg Glu Phe Val Ala Ala
                805                 810                 815

Ile Pro Gln Ser Gly Gly Arg Ser Tyr Tyr Ala Asp Ser Val Lys Gly
            820                 825                 830

Arg Phe Thr Ile Ser Arg Asp Asn Ala Lys Asn Thr Val Tyr Leu Gln
        835                 840                 845

Met Asn Ser Leu Lys Pro Glu Asp Thr Ala Val Tyr Ser Cys Ala Ala
    850                 855                 860

Thr Ser Thr Tyr Tyr Gly Arg Ser Ala Tyr Ser Ser His Ser Gly Gly
865                 870                 875                 880

Tyr Asp Tyr Trp Gly Gln Gly Thr Gln Val Thr Val Ser Ser Gly Gly
                885                 890                 895

Gly Ser Gly Gly Gly Ser Gly Gly Ser Gly Gly Ser Gln Val
            900                 905                 910

Gln Leu Val Gln Ser Gly Gly Gly Leu Val Gln Ala Gly Asp Ser Leu
    915                 920                 925

Arg Leu Ser Cys Ala Ala Ser Gly Arg Thr Phe Ile Arg Tyr Ala Met
    930                 935                 940

Ala Trp Phe Arg Gln Ala Pro Gly Lys Glu Arg Glu Phe Val Ala Ala
945                 950                 955                 960

Ile Pro Gln Ser Gly Gly Arg Ser Tyr Tyr Ala Asp Ser Val Lys Gly
            965                 970                 975

Arg Phe Thr Ile Ser Arg Asp Asn Ala Lys Asn Thr Val Tyr Leu Gln
        980                 985                 990

Met Asn Ser Leu Lys Pro Glu Asp Thr Ala Val Tyr Ser Cys Ala Ala
    995                 1000                1005

Thr Ser Thr Tyr Tyr Gly Arg Ser Ala Tyr Ser Ser His Ser Gly
    1010                1015                1020

Gly Tyr Asp Tyr Trp Gly Gln Gly Thr Gln Val Thr Val Ser Ser
    1025                1030                1035

Gly Gly Gly Ser Gly Gly Gly Ser Gly Gly Gly Ser Gly Gly Gly
    1040                1045                1050
```

```
Ser Gly Gly Gly Ser Gly Gly Gly Ser Glu Ile Thr Arg Thr Thr
1055                1060                1065

Leu Gln Ser Asp Gln Glu Glu Ile Asp Tyr Asp Asp Thr Ile Ser
1070                1075                1080

Val Glu Met Lys Lys Glu Asp Phe Asp Ile Tyr Asp Glu Asp Glu
1085                1090                1095

Asn Gln Ser Pro Arg Ser Phe Gln Lys Lys Thr Arg His Tyr Phe
1100                1105                1110

Ile Ala Ala Val Glu Arg Leu Trp Asp Tyr Gly Met Ser Ser Ser
1115                1120                1125

Pro His Val Leu Arg Asn Arg Ala Gln Ser Gly Ser Val Pro Gln
1130                1135                1140

Phe Lys Lys Val Val Phe Gln Glu Phe Thr Asp Gly Ser Phe Thr
1145                1150                1155

Gln Pro Leu Tyr Arg Gly Glu Leu Asn Glu His Leu Gly Leu Leu
1160                1165                1170

Gly Pro Tyr Ile Arg Ala Glu Val Glu Asp Asn Ile Met Val Thr
1175                1180                1185

Phe Arg Asn Gln Ala Ser Arg Pro Tyr Ser Phe Tyr Ser Ser Leu
1190                1195                1200

Ile Ser Tyr Glu Glu Asp Gln Arg Gln Gly Ala Glu Pro Arg Lys
1205                1210                1215

Asn Phe Val Lys Pro Asn Glu Thr Lys Thr Tyr Phe Trp Lys Val
1220                1225                1230

Gln His His Met Ala Pro Thr Lys Asp Glu Phe Asp Cys Lys Ala
1235                1240                1245

Trp Ala Tyr Phe Ser Asp Val Asp Leu Glu Lys Asp Val His Ser
1250                1255                1260

Gly Leu Ile Gly Pro Leu Leu Val Cys His Thr Asn Thr Leu Asn
1265                1270                1275

Pro Ala His Gly Arg Gln Val Thr Val Gln Glu Phe Ala Leu Phe
1280                1285                1290

Phe Thr Ile Phe Asp Glu Thr Lys Ser Trp Tyr Phe Thr Glu Asn
1295                1300                1305

Met Glu Arg Asn Cys Arg Ala Pro Cys Asn Ile Gln Met Glu Asp
1310                1315                1320

Pro Thr Phe Lys Glu Asn Tyr Arg Phe His Ala Ile Asn Gly Tyr
1325                1330                1335

Ile Met Asp Thr Leu Pro Gly Leu Val Met Ala Gln Asp Gln Arg
1340                1345                1350

Ile Arg Trp Tyr Leu Leu Ser Met Gly Ser Asn Glu Asn Ile His
1355                1360                1365

Ser Ile His Phe Ser Gly His Val Phe Thr Val Arg Lys Lys Glu
1370                1375                1380

Glu Tyr Lys Met Ala Leu Tyr Asn Leu Tyr Pro Gly Val Phe Glu
1385                1390                1395

Thr Val Glu Met Leu Pro Ser Lys Ala Gly Ile Trp Arg Val Glu
1400                1405                1410

Cys Leu Ile Gly Glu His Leu His Ala Gly Met Ser Thr Leu Phe
1415                1420                1425

Leu Val Tyr Ser Asn Lys Cys Gln Thr Pro Leu Gly Met Ala Ser
1430                1435                1440
```

```
Gly His Ile Arg Asp Phe Gln Ile Thr Ala Ser Gly Gln Tyr Gly
    1445                1450                1455

Gln Trp Ala Pro Lys Leu Ala Arg Leu His Tyr Ser Gly Ser Ile
    1460                1465                1470

Asn Ala Trp Ser Thr Lys Glu Pro Phe Ser Trp Ile Lys Val Asp
    1475                1480                1485

Leu Leu Ala Pro Met Ile Ile His Gly Ile Lys Thr Gln Gly Ala
    1490                1495                1500

Arg Gln Lys Phe Ser Ser Leu Tyr Ile Ser Gln Phe Ile Ile Met
    1505                1510                1515

Tyr Ser Leu Asp Gly Lys Lys Trp Gln Thr Tyr Arg Gly Asn Ser
    1520                1525                1530

Thr Gly Thr Leu Met Val Phe Phe Gly Asn Val Asp Ser Ser Gly
    1535                1540                1545

Ile Lys His Asn Ile Phe Asn Pro Pro Ile Ile Ala Arg Tyr Ile
    1550                1555                1560

Arg Leu His Pro Thr His Tyr Ser Ile Arg Ser Thr Leu Arg Met
    1565                1570                1575

Glu Trp Met Gly Cys Asp Leu Asn Ser Cys Ser Met Pro Leu Gly
    1580                1585                1590

Met Glu Ser Lys Ala Ile Ser Asp Ala Gln Ile Thr Ala Ser Ser
    1595                1600                1605

Tyr Phe Thr Asn Met Phe Ala Thr Trp Ser Pro Ser Lys Ala Arg
    1610                1615                1620

Leu His Leu Gln Gly Arg Ser Asn Ala Trp Arg Pro Gln Val Asn
    1625                1630                1635

Asn Pro Lys Glu Trp Leu Gln Val Asp Phe Gln Lys Thr Met Lys
    1640                1645                1650

Val Thr Gly Val Thr Thr Gln Gly Val Lys Ser Leu Leu Thr Ser
    1655                1660                1665

Met Tyr Val Lys Glu Phe Leu Ile Ser Ser Ser Gln Asp Gly His
    1670                1675                1680

Gln Trp Thr Leu Phe Phe Gln Asn Gly Lys Val Lys Val Phe Gln
    1685                1690                1695

Gly Asn Gln Asp Ser Phe Thr Pro Val Val Asn Ser Leu Asp Pro
    1700                1705                1710

Pro Leu Leu Thr Arg Tyr Leu Arg Ile His Pro Gln Ser Trp Val
    1715                1720                1725

His Gln Ile Ala Leu Arg Met Glu Val Leu Gly Cys Glu Ala Gln
    1730                1735                1740

Asp Leu Tyr Leu Thr Pro Arg Gly Val Arg Leu Gly Gly Gly Ser
    1745                1750                1755

Gly Gly Gly Ser Gly Gly Gly Ser Gly Gly Gly Ser Gln Val Gln
    1760                1765                1770

Leu Val Gln Ser Gly Gly Gly Leu Val Gln Ala Gly Asp Ser Leu
    1775                1780                1785

Arg Leu Ser Cys Ala Ala Ser Gly Arg Thr Phe Ile Arg Tyr Ala
    1790                1795                1800

Met Ala Trp Phe Arg Gln Ala Pro Gly Lys Glu Arg Glu Phe Val
    1805                1810                1815

Ala Ala Ile Pro Gln Ser Gly Gly Arg Ser Tyr Tyr Ala Asp Ser
    1820                1825                1830
```

```
Val Lys Gly Arg Phe Thr Ile Ser Arg Asp Asn Ala Lys Asn Thr
    1835                1840                1845

Val Tyr Leu Gln Met Asn Ser Leu Lys Pro Glu Asp Thr Ala Val
    1850                1855                1860

Tyr Ser Cys Ala Ala Thr Ser Thr Tyr Tyr Gly Arg Ser Ala Tyr
    1865                1870                1875

Ser Ser His Ser Gly Gly Tyr Asp Tyr Trp Gly Gln Gly Thr Gln
    1880                1885                1890

Val Thr Val Ser Ser Gly Gly Gly Ser Gly Gly Ser Gly Gly
    1895                1900                1905

Gly Ser Gly Gly Gly Ser Gln Val Gln Leu Val Gln Ser Gly Gly
    1910                1915                1920

Gly Leu Val Gln Ala Gly Asp Ser Leu Arg Leu Ser Cys Ala Ala
    1925                1930                1935

Ser Gly Arg Thr Phe Ile Arg Tyr Ala Met Ala Trp Phe Arg Gln
    1940                1945                1950

Ala Pro Gly Lys Glu Arg Glu Phe Val Ala Ala Ile Pro Gln Ser
    1955                1960                1965

Gly Gly Arg Ser Tyr Tyr Ala Asp Ser Val Lys Gly Arg Phe Thr
    1970                1975                1980

Ile Ser Arg Asp Asn Ala Lys Asn Thr Val Tyr Leu Gln Met Asn
    1985                1990                1995

Ser Leu Lys Pro Glu Asp Thr Ala Val Tyr Ser Cys Ala Ala Thr
    2000                2005                2010

Ser Thr Tyr Tyr Gly Arg Ser Ala Tyr Ser Ser His Ser Gly Gly
    2015                2020                2025

Tyr Asp Tyr Trp Gly Gln Gly Thr Gln Val Thr Val Ser Ser
    2030                2035                2040

<210> SEQ ID NO 23
<211> LENGTH: 2042
<212> TYPE: PRT
<213> ORGANISM: Artificial
<220> FEATURE:
<223> OTHER INFORMATION: Synthetic FVIII_KB0013bv(6GGGS)_Cter-
      0013bv_Y1680F SEQ ID NO: 23

<400> SEQUENCE: 23

Met Gln Ile Glu Leu Ser Thr Cys Phe Phe Leu Cys Leu Leu Arg Phe
1               5                   10                  15

Cys Phe Ser Ala Thr Arg Arg Tyr Tyr Leu Gly Ala Val Glu Leu Ser
                20                  25                  30

Trp Asp Tyr Met Gln Ser Asp Leu Gly Glu Leu Pro Val Asp Ala Arg
            35                  40                  45

Phe Pro Pro Arg Val Pro Lys Ser Phe Pro Phe Asn Thr Ser Val Val
        50                  55                  60

Tyr Lys Lys Thr Leu Phe Val Glu Phe Thr Asp His Leu Phe Asn Ile
65                  70                  75                  80

Ala Lys Pro Arg Pro Pro Trp Met Gly Leu Leu Gly Pro Thr Ile Gln
                85                  90                  95

Ala Glu Val Tyr Asp Thr Val Val Ile Thr Leu Lys Asn Met Ala Ser
            100                 105                 110

His Pro Val Ser Leu His Ala Val Gly Val Ser Tyr Trp Lys Ala Ser
        115                 120                 125
```

```
Glu Gly Ala Glu Tyr Asp Asp Gln Thr Ser Gln Arg Glu Lys Glu Asp
    130                 135                 140
Asp Lys Val Phe Pro Gly Gly Ser His Thr Tyr Val Trp Gln Val Leu
145                 150                 155                 160
Lys Glu Asn Gly Pro Met Ala Ser Asp Pro Leu Cys Leu Thr Tyr Ser
                165                 170                 175
Tyr Leu Ser His Val Asp Leu Val Lys Asp Leu Asn Ser Gly Leu Ile
            180                 185                 190
Gly Ala Leu Leu Val Cys Arg Glu Gly Ser Leu Ala Lys Glu Lys Thr
        195                 200                 205
Gln Thr Leu His Lys Phe Ile Leu Leu Phe Ala Val Phe Asp Glu Gly
    210                 215                 220
Lys Ser Trp His Ser Glu Thr Lys Asn Ser Leu Met Gln Asp Arg Asp
225                 230                 235                 240
Ala Ala Ser Ala Arg Ala Trp Pro Lys Met His Thr Val Asn Gly Tyr
                245                 250                 255
Val Asn Arg Ser Leu Pro Gly Leu Ile Gly Cys His Arg Lys Ser Val
            260                 265                 270
Tyr Trp His Val Ile Gly Met Gly Thr Thr Pro Glu Val His Ser Ile
        275                 280                 285
Phe Leu Glu Gly His Thr Phe Leu Val Arg Asn His Arg Gln Ala Ser
    290                 295                 300
Leu Glu Ile Ser Pro Ile Thr Phe Leu Thr Ala Gln Thr Leu Leu Met
305                 310                 315                 320
Asp Leu Gly Gln Phe Leu Leu Phe Cys His Ile Ser Ser His Gln His
                325                 330                 335
Asp Gly Met Glu Ala Tyr Val Lys Val Asp Ser Cys Pro Glu Glu Pro
            340                 345                 350
Gln Leu Arg Met Lys Asn Asn Glu Glu Ala Glu Asp Tyr Asp Asp Asp
        355                 360                 365
Leu Thr Asp Ser Glu Met Asp Val Val Arg Phe Asp Asp Asp Asn Ser
    370                 375                 380
Pro Ser Phe Ile Gln Ile Arg Ser Val Ala Lys Lys His Pro Lys Thr
385                 390                 395                 400
Trp Val His Tyr Ile Ala Ala Glu Glu Glu Asp Trp Asp Tyr Ala Pro
                405                 410                 415
Leu Val Leu Ala Pro Asp Asp Arg Ser Tyr Lys Ser Gln Tyr Leu Asn
            420                 425                 430
Asn Gly Pro Gln Arg Ile Gly Arg Lys Tyr Lys Lys Val Arg Phe Met
        435                 440                 445
Ala Tyr Thr Asp Glu Thr Phe Lys Thr Arg Glu Ala Ile Gln His Glu
    450                 455                 460
Ser Gly Ile Leu Gly Pro Leu Leu Tyr Gly Glu Val Gly Asp Thr Leu
465                 470                 475                 480
Leu Ile Ile Phe Lys Asn Gln Ala Ser Arg Pro Tyr Asn Ile Tyr Pro
                485                 490                 495
His Gly Ile Thr Asp Val Arg Pro Leu Tyr Ser Arg Arg Leu Pro Lys
            500                 505                 510
Gly Val Lys His Leu Lys Asp Phe Pro Ile Leu Pro Gly Glu Ile Phe
        515                 520                 525
Lys Tyr Lys Trp Thr Val Thr Val Glu Asp Gly Pro Thr Lys Ser Asp
    530                 535                 540
```

-continued

```
Pro Arg Cys Leu Thr Arg Tyr Tyr Ser Ser Phe Val Asn Met Glu Arg
545                 550                 555                 560

Asp Leu Ala Ser Gly Leu Ile Gly Pro Leu Leu Ile Cys Tyr Lys Glu
            565                 570                 575

Ser Val Asp Gln Arg Gly Asn Gln Ile Met Ser Asp Lys Arg Asn Val
        580                 585                 590

Ile Leu Phe Ser Val Phe Asp Glu Asn Arg Ser Trp Tyr Leu Thr Glu
    595                 600                 605

Asn Ile Gln Arg Phe Leu Pro Asn Pro Ala Gly Val Gln Leu Glu Asp
610                 615                 620

Pro Glu Phe Gln Ala Ser Asn Ile Met His Ser Ile Asn Gly Tyr Val
625                 630                 635                 640

Phe Asp Ser Leu Gln Leu Ser Val Cys Leu His Glu Val Ala Tyr Trp
            645                 650                 655

Tyr Ile Leu Ser Ile Gly Ala Gln Thr Asp Phe Leu Ser Val Phe Phe
        660                 665                 670

Ser Gly Tyr Thr Phe Lys His Lys Met Val Tyr Glu Asp Thr Leu Thr
    675                 680                 685

Leu Phe Pro Phe Ser Gly Glu Thr Val Phe Met Ser Met Glu Asn Pro
690                 695                 700

Gly Leu Trp Ile Leu Gly Cys His Asn Ser Asp Phe Arg Asn Arg Gly
705                 710                 715                 720

Met Thr Ala Leu Leu Lys Val Ser Ser Cys Asp Lys Asn Thr Gly Asp
            725                 730                 735

Tyr Tyr Glu Asp Ser Tyr Glu Asp Ile Ser Ala Tyr Leu Leu Ser Lys
        740                 745                 750

Asn Asn Ala Ile Glu Pro Arg Ser Phe Ser Gly Gly Ser Gln Val
755                 760                 765

Gln Leu Val Gln Ser Gly Gly Gly Leu Val Gln Ala Gly Asp Ser Leu
770                 775                 780

Arg Leu Ser Cys Ala Ala Ser Gly Arg Thr Phe Ile Arg Tyr Ala Met
785                 790                 795                 800

Ala Trp Phe Arg Gln Ala Pro Gly Lys Glu Arg Glu Phe Val Ala Ala
            805                 810                 815

Ile Pro Gln Ser Gly Gly Arg Ser Tyr Tyr Ala Asp Ser Val Lys Gly
        820                 825                 830

Arg Phe Thr Ile Ser Arg Asp Asn Ala Lys Asn Thr Val Tyr Leu Gln
    835                 840                 845

Met Asn Ser Leu Lys Pro Glu Asp Thr Ala Val Tyr Ser Cys Ala Ala
850                 855                 860

Thr Ser Thr Tyr Tyr Gly Arg Ser Ala Tyr Ser Ser His Ser Gly Gly
865                 870                 875                 880

Tyr Asp Tyr Trp Gly Gln Gly Thr Gln Val Thr Val Ser Ser Gly Gly
            885                 890                 895

Gly Ser Gly Gly Gly Ser Gly Gly Gly Ser Gly Gly Gly Ser Gln Val
        900                 905                 910

Gln Leu Val Gln Ser Gly Gly Gly Leu Val Gln Ala Gly Asp Ser Leu
    915                 920                 925

Arg Leu Ser Cys Ala Ala Ser Gly Arg Thr Phe Ile Arg Tyr Ala Met
930                 935                 940

Ala Trp Phe Arg Gln Ala Pro Gly Lys Glu Arg Glu Phe Val Ala Ala
945                 950                 955                 960
```

```
Ile Pro Gln Ser Gly Gly Arg Ser Tyr Tyr Ala Asp Ser Val Lys Gly
            965                 970                 975

Arg Phe Thr Ile Ser Arg Asp Asn Ala Lys Asn Thr Val Tyr Leu Gln
            980                 985                 990

Met Asn Ser Leu Lys Pro Glu Asp Thr Ala Val Tyr Ser Cys Ala Ala
            995                 1000                1005

Thr Ser Thr Tyr Tyr Gly Arg Ser Ala Tyr Ser Ser His Ser Gly
        1010                1015                1020

Gly Tyr Asp Tyr Trp Gly Gln Gly Thr Gln Val Thr Val Ser Ser
        1025                1030                1035

Gly Gly Gly Ser Gly Gly Gly Ser Gly Gly Gly Ser Gly Gly Gly
        1040                1045                1050

Ser Gly Gly Ser Gly Gly Gly Ser Glu Ile Thr Arg Thr Thr
        1055                1060                1065

Leu Gln Ser Asp Gln Glu Glu Ile Asp Tyr Asp Asp Thr Ile Ser
        1070                1075                1080

Val Glu Met Lys Lys Glu Asp Phe Asp Ile Phe Asp Glu Asp Glu
        1085                1090                1095

Asn Gln Ser Pro Arg Ser Phe Gln Lys Lys Thr Arg His Tyr Phe
        1100                1105                1110

Ile Ala Ala Val Glu Arg Leu Trp Asp Tyr Gly Met Ser Ser Ser
        1115                1120                1125

Pro His Val Leu Arg Asn Arg Ala Gln Ser Gly Ser Val Pro Gln
        1130                1135                1140

Phe Lys Lys Val Val Phe Gln Glu Phe Thr Asp Gly Ser Phe Thr
        1145                1150                1155

Gln Pro Leu Tyr Arg Gly Glu Leu Asn Glu His Leu Gly Leu Leu
        1160                1165                1170

Gly Pro Tyr Ile Arg Ala Glu Val Glu Asp Asn Ile Met Val Thr
        1175                1180                1185

Phe Arg Asn Gln Ala Ser Arg Pro Tyr Ser Phe Tyr Ser Ser Leu
        1190                1195                1200

Ile Ser Tyr Glu Glu Asp Gln Arg Gln Gly Ala Glu Pro Arg Lys
        1205                1210                1215

Asn Phe Val Lys Pro Asn Glu Thr Lys Thr Tyr Phe Trp Lys Val
        1220                1225                1230

Gln His His Met Ala Pro Thr Lys Asp Glu Phe Asp Cys Lys Ala
        1235                1240                1245

Trp Ala Tyr Phe Ser Asp Val Asp Leu Glu Lys Asp Val His Ser
        1250                1255                1260

Gly Leu Ile Gly Pro Leu Leu Val Cys His Thr Asn Thr Leu Asn
        1265                1270                1275

Pro Ala His Gly Arg Gln Val Thr Val Gln Glu Phe Ala Leu Phe
        1280                1285                1290

Phe Thr Ile Phe Asp Glu Thr Lys Ser Trp Tyr Phe Thr Glu Asn
        1295                1300                1305

Met Glu Arg Asn Cys Arg Ala Pro Cys Asn Ile Gln Met Glu Asp
        1310                1315                1320

Pro Thr Phe Lys Glu Asn Tyr Arg Phe His Ala Ile Asn Gly Tyr
        1325                1330                1335

Ile Met Asp Thr Leu Pro Gly Leu Val Met Ala Gln Asp Gln Arg
        1340                1345                1350
```

```
Ile Arg Trp Tyr Leu Leu Ser Met Gly Ser Asn Glu Asn Ile His
1355                     1360                1365

Ser Ile His Phe Ser Gly His Val Phe Thr Val Arg Lys Lys Glu
1370                     1375                1380

Glu Tyr Lys Met Ala Leu Tyr Asn Leu Tyr Pro Gly Val Phe Glu
1385                     1390                1395

Thr Val Glu Met Leu Pro Ser Lys Ala Gly Ile Trp Arg Val Glu
1400                     1405                1410

Cys Leu Ile Gly Glu His Leu His Ala Gly Met Ser Thr Leu Phe
1415                     1420                1425

Leu Val Tyr Ser Asn Lys Cys Gln Thr Pro Leu Gly Met Ala Ser
1430                     1435                1440

Gly His Ile Arg Asp Phe Gln Ile Thr Ala Ser Gly Gln Tyr Gly
1445                     1450                1455

Gln Trp Ala Pro Lys Leu Ala Arg Leu His Tyr Ser Gly Ser Ile
1460                     1465                1470

Asn Ala Trp Ser Thr Lys Glu Pro Phe Ser Trp Ile Lys Val Asp
1475                     1480                1485

Leu Leu Ala Pro Met Ile Ile His Gly Ile Lys Thr Gln Gly Ala
1490                     1495                1500

Arg Gln Lys Phe Ser Ser Leu Tyr Ile Ser Gln Phe Ile Ile Met
1505                     1510                1515

Tyr Ser Leu Asp Gly Lys Lys Trp Gln Thr Tyr Arg Gly Asn Ser
1520                     1525                1530

Thr Gly Thr Leu Met Val Phe Phe Gly Asn Val Asp Ser Ser Gly
1535                     1540                1545

Ile Lys His Asn Ile Phe Asn Pro Pro Ile Ile Ala Arg Tyr Ile
1550                     1555                1560

Arg Leu His Pro Thr His Tyr Ser Ile Arg Ser Thr Leu Arg Met
1565                     1570                1575

Glu Trp Met Gly Cys Asp Leu Asn Ser Cys Ser Met Pro Leu Gly
1580                     1585                1590

Met Glu Ser Lys Ala Ile Ser Asp Ala Gln Ile Thr Ala Ser Ser
1595                     1600                1605

Tyr Phe Thr Asn Met Phe Ala Thr Trp Ser Pro Ser Lys Ala Arg
1610                     1615                1620

Leu His Leu Gln Gly Arg Ser Asn Ala Trp Arg Pro Gln Val Asn
1625                     1630                1635

Asn Pro Lys Glu Trp Leu Gln Val Asp Phe Gln Lys Thr Met Lys
1640                     1645                1650

Val Thr Gly Val Thr Thr Gln Gly Val Lys Ser Leu Leu Thr Ser
1655                     1660                1665

Met Tyr Val Lys Glu Phe Leu Ile Ser Ser Ser Gln Asp Gly His
1670                     1675                1680

Gln Trp Thr Leu Phe Phe Gln Asn Gly Lys Val Lys Val Phe Gln
1685                     1690                1695

Gly Asn Gln Asp Ser Phe Thr Pro Val Val Asn Ser Leu Asp Pro
1700                     1705                1710

Pro Leu Leu Thr Arg Tyr Leu Arg Ile His Pro Gln Ser Trp Val
1715                     1720                1725

His Gln Ile Ala Leu Arg Met Glu Val Leu Gly Cys Glu Ala Gln
1730                     1735                1740
```

```
Asp Leu Tyr Leu Thr Pro Arg Gly Val Arg Leu Gly Gly Gly Ser
    1745            1750                1755

Gly Gly Gly Ser Gly Gly Gly Ser Gly Gly Gly Ser Gln Val Gln
    1760            1765                1770

Leu Val Gln Ser Gly Gly Gly Leu Val Gln Ala Gly Asp Ser Leu
    1775            1780                1785

Arg Leu Ser Cys Ala Ala Ser Gly Arg Thr Phe Ile Arg Tyr Ala
    1790            1795                1800

Met Ala Trp Phe Arg Gln Ala Pro Gly Lys Glu Arg Glu Phe Val
    1805            1810                1815

Ala Ala Ile Pro Gln Ser Gly Gly Arg Ser Tyr Tyr Ala Asp Ser
    1820            1825                1830

Val Lys Gly Arg Phe Thr Ile Ser Arg Asp Asn Ala Lys Asn Thr
    1835            1840                1845

Val Tyr Leu Gln Met Asn Ser Leu Lys Pro Glu Asp Thr Ala Val
    1850            1855                1860

Tyr Ser Cys Ala Ala Thr Ser Thr Tyr Tyr Gly Arg Ser Ala Tyr
    1865            1870                1875

Ser Ser His Ser Gly Gly Tyr Asp Tyr Trp Gly Gln Gly Thr Gln
    1880            1885                1890

Val Thr Val Ser Ser Gly Gly Gly Ser Gly Gly Gly Ser Gly Gly
    1895            1900                1905

Gly Ser Gly Gly Gly Ser Gln Val Gln Leu Val Gln Ser Gly Gly
    1910            1915                1920

Gly Leu Val Gln Ala Gly Asp Ser Leu Arg Leu Ser Cys Ala Ala
    1925            1930                1935

Ser Gly Arg Thr Phe Ile Arg Tyr Ala Met Ala Trp Phe Arg Gln
    1940            1945                1950

Ala Pro Gly Lys Glu Arg Glu Phe Val Ala Ala Ile Pro Gln Ser
    1955            1960                1965

Gly Gly Arg Ser Tyr Tyr Ala Asp Ser Val Lys Gly Arg Phe Thr
    1970            1975                1980

Ile Ser Arg Asp Asn Ala Lys Asn Thr Val Tyr Leu Gln Met Asn
    1985            1990                1995

Ser Leu Lys Pro Glu Asp Thr Ala Val Tyr Ser Cys Ala Ala Thr
    2000            2005                2010

Ser Thr Tyr Tyr Gly Arg Ser Ala Tyr Ser Ser His Ser Gly Gly
    2015            2020                2025

Tyr Asp Tyr Trp Gly Gln Gly Thr Gln Val Thr Val Ser Ser
    2030            2035                2040
```

ANTI-VWF D'D3 SINGLE-DOMAIN ANTIBODIES FUSE TO CLOTTING FACTORS

FIELD OF THE INVENTION

The invention is in the field of immunotherapy. More particularly, the invention relates to isolated single-domain antibodies (sdAb) directed against von Willebrand Factor (VWF) D'D3 domain and polypeptides comprising thereof such as blood clotting factors and their uses in therapy such as in the prevention and treatment of hemostatic disorders.

BACKGROUND OF THE INVENTION

Extending in vivo half-life of therapeutic proteins, thereby enhancing their efficiency is a major concern in the pharmaceutical field. Numerous strategies have been employed towards this end, including covalent modification, such as through PEGylation or Fc-Fusion proteins, which improves protein stability and solubility, prevents proteolytic degradation, and reduces the clearance rate from the bloodstream. Such approaches have been applied to different therapeutic proteins and for different disorders such as Haemophilia A which is a bleeding disorder caused by defects in the gene encoding coagulation factor VIII (FVIII) and affects 1-2 in 10,000 male births. Patients affected with hemophilia A can be treated with infusion of purified plasma-derived or recombinantly produced FVIII. All commercially available FVIII products, however, are known to have a short half-life of several hours (7-21 hours, Van Dijk et al Haematologica 2005 92:494-498), requiring frequent intravenous administration to the patients. Thus, a number of approaches have been tried in order to extend the FVIII half-life. For example, the approaches in development to extend the half-life of clotting factors include chemical (PEGylation)[1] or genetic modification (Fc-fusion)[2] of the FVIII molecule. Regardless of the protein engineering used, however, the long acting FVIII products currently under development are reported to have limited half-lives—only to about 1.5 to 2 hours in preclinical animal models. Consistent results have been demonstrated in humans, for example, rFVIIIFc was reported to improve half-life up to 1.7 fold compared with ADVATE® in hemophilia A patients.

Due to the frequent dosing and inconvenience caused by the dosing schedule, there is still a need to develop FVIII products requiring less frequent administration, i.e., a FVIII product that has a half-life longer than the 1.5 to 2 fold half-life limitation.

SUMMARY OF THE INVENTION

The invention relates to isolated single-domain antibodies (sdAb) directed against von Willebrand Factor (VWF) D'D3 domain and polypeptides comprising thereof such as blood clotting factors and their uses in therapy such as in the prevention and treatment of hemostatic disorders. In particular, the present invention is defined by the claims.

DETAILED DESCRIPTION OF THE INVENTION

The invention relies on the discovery that introducing an isolated single-domain antibody (sdAb) directed against the von Willebrand factor (VWF) D'D3 domain into a therapeutic peptide leads to obtain a polypeptide with a half-life significantly increased. Indeed, the chimeric polypeptide according to the invention shows a reduced dissociation from VWF leading to more stable complex formation. This results in reduced clearance rates and thus an extended half-life. For instance, the inventors show that a chimeric FVIII polypeptide in which two isolated sdAb directed against VWF D'D3 domain (FVIII-KB013bv) are inserted thereby replacing the B-domain exhibits an extended half-life comparatively to wild-type B-domainless FVIII (T½ for wt-FVIII is 1.10 h (95% confidence interval: 0.88-1.48 h) and T½ for FVIII-KB-013bv is 2.11 h (95% CI: 1.66-2.92 h) when determined in haemophilic mice. Half-life extension is thus 2.11/1.10=1.9-fold. The sdAb directed against VWF D'D3 domain can also be used to induce complex formation with proteins that otherwise do not bind VWF. For example, a fusion protein FVII-KB013bv (consisting of FVII and two isolated sdAbs at the C-terminal end of FVII) but not FVII was found to form a complex with VWF. Furthermore, the inventors also demonstrated that such chimeric FVIII polypeptide may be complexed with VWF variants in order to improve even more its half-life (e.g. FVIII-KB013bv/D'D3-Fc). Thus, for the first time, inventors have demonstrated an increase of half-life with such construction.

Single-Domain Antibodies Directed Against VWF D'D3 Domain of the Invention:

In a first aspect, the invention relates to an isolated single-domain antibody (sdAb) directed against von Willebrand Factor (VWF) D'D3 domain.

By "isolated" it is meant, when referring to a single-domain antibody according to the invention, that the indicated molecule is present in the substantial absence of other biological macromolecules of the same type.

As used herein the term "single-domain antibody" (sdAb) has its general meaning in the art and refers to the single heavy chain variable domain of antibodies of the type that can be found in Camelid mammals which are naturally devoid of light chains. Such single-domain antibody are also called VHH or "Nanobody®". For a general description of (single) domain antibodies, reference is also made to the prior art cited above, as well as to EP 0 368 684, Ward et al. (Nature 1989 Oct. 12; 341 (6242): 544-6), Holt et al, Trends Biotechnol, 2003, 21(1 1):484-490; and WO 06/030220, WO 06/003388. The amino acid sequence and structure of a single-domain antibody can be considered to be comprised of four framework regions or "FRs" which are referred to in the art and herein as "Framework region 1" or "FR1"; as "Framework region 2" or "FR2"; as "Framework region 3" or "FR3"; and as "Framework region 4" or "FR4" respectively; which framework regions are interrupted by three complementary determining regions or "CDRs", which are referred to in the art as "Complementary Determining Region 1" or "CDR1"; as "Complementarity Determining Region 2" or "CDR2" and as "Complementarity Determining Region 3" or "CDR3", respectively. Accordingly, the single-domain antibody can be defined as an amino acid sequence with the general structure: FR1-CDR1-FR2-CDR2-FR3-CDR3-FR4 in which FR1 to FR4 refer to framework regions 1 to 4 respectively, and in which CDR1 to CDR3 refer to the complementarity determining regions 1 to 3. In the context of the invention, the amino acid residues of the single-domain antibody are numbered according to the general numbering for VH domains given by the International ImMunoGeneTics information system aminoacid numbering (http://imgt.cines.fr/).

The term "VWF" has its general meaning in the art and refers to the human von Willebrand factor (VWF) which is a blood glycoprotein involved in blood clotting. VWF is a monomer composed of several homologous domains each covering different functions: D1-D2-D'-D3-A1-A2-A3-D4-C1-C2-C3-C4-C5-C6-CK. The naturally occurring human VWF protein has an aminoacid sequence as shown in GeneBank Accession number NP_000543.2. Monomers are subsequently arranged into dimers or multimers by cross-linking of cysteine residues via disulfide bonds. Multimers of VWF can thus be extremely large and can consist of over 40 monomers also called high molecular weight (HMW)-multimers of VWF.

Preferably, the single-domain antibody directed against von VWF D'D3 domain does not induce the unfolding of VWF (which leads to exposure of platelet-binding sites). Moreover, within the context of the invention the single-domain antibody directed against von VWF D'D3 domain does not block the binding to VWF of a polypeptide such as a clotting factor comprising such single-domain antibody as described below.

The inventors have isolated a single-domain antibody (sdAb) KB-VWF-013 with the required properties and characterized the complementarity determining regions (CDRs) of said KB-VWF-013 and thus determined the CDRs of said sdAb (Table A):

TABLE A

Sequences of KB-VWF-013 domains.

| KB-VWF-013 domains | Sequences |
|---|---|
| CDR1 | SEQ ID NO: 1<br>GRTFIRYAMA |
| CDR2 | SEQ ID NO: 2<br>IPQSGGRSYYADSVKG |
| CDR3 | SEQ ID NO: 3<br>TSTYYGRSAYSSHSGGYDY |
| SEQUENCE KB-VWF-013 | SEQ ID NO: 4<br>QVQLVQSGGGLVQAGDSLRLSCAAS GRTFIRYAMA WFRQAPGKEREFVAA IPQSGGRSYYADSVKG RFTISRDNAKNTVYLQMNSLKPEDTAVYSCAA TSTYYGRSAYSSHSGGYDY WGQGTQVTVSS |

In particular, the invention relates to an isolated single-domain antibody (sdAb) comprising a CDR1 having at least 80%, preferably at least 90%, more preferably at least 95%, even more preferably at least 99% sequence identity with sequence set forth as SEQ ID NO: 1, a CDR2 having at least 80%, preferably at least 90%, more preferably at least 95%, even more preferably at least 99% sequence identity with sequence set forth as SEQ ID NO: 2 and a CDR3 having at least 80%, preferably at least 90%, more preferably at least 95%, even more preferably at least 99% sequence identity with sequence set forth as SEQ ID NO: 3.

Amino acid sequence identity is preferably determined using a suitable sequence alignment algorithm and default parameters, such as BLAST P (Karlin and Altschul, Proc. Natl Acad. Sci. USA 87(6):2264-2268 (1990)).

In some embodiments, the isolated single-domain antibody according to the invention comprises a CDR1 having a sequence set forth as SEQ ID NO: 1, a CDR2 having a sequence set forth as SEQ ID NO: 2 and a CDR3 having a sequence set forth as SEQ ID NO: 3.

In some embodiments, the isolated single-domain antibody according to the invention has the sequence set forth as SEQ ID NO: 4.

It should be further noted that the sdAb KB-VWF-013 cross-react with murine VWF, which is of interest for preclinical evaluation and toxicological studies.

Other examples of sdAb against VWF D'D3 that do not block FVIII binding (potential CDRs are indicated in bold):

TABLE B

Sequences of KB-VWF-008 domains.

| KB-VWF-008 domains | Sequences |
|---|---|
| CDR1 | SEQ ID NO: 5<br>GRTFSDYAMG |
| CDR2 | SEQ ID NO: 6<br>INRSGGRLSYAESVND |
| CDR3 | SEQ ID NO: 7<br>RTNWNPPRPLPEEYNY |
| SEQUENCE KB-VWF-008 | SEQ ID NO: 8<br>QVQLVQSGGGLVQAGDSLKLSCAAS GRTFSDYAMG CILQ NPGKERDFVAS INRSGGRLSYAESVND LFTISVDNAKNM LYLQMNSLKPEDTAVHYCVL RTNWNPPRPLPEEYNY WGQ ETQVTVSS |

In particular, the invention relates to an isolated single-domain antibody (sdAb) comprising a CDR1 having at least 80%, preferably at least 90%, more preferably at least 95%, even more preferably at least 99% sequence identity with sequence set forth as SEQ ID NO: 5, a CDR2 having at least 80%, preferably at least 90%, more preferably at least 95%, even more preferably at least 99% sequence identity with sequence set forth as SEQ ID NO: 6 and a CDR3 having at least 80%, preferably at least 90%, more preferably at least 95%, even more preferably at least 99% sequence identity with sequence set forth as SEQ ID NO: 7.

In some embodiments, the isolated single-domain antibody according to the invention comprises a CDR1 having a sequence set forth as SEQ ID NO: 5, a CDR2 having a sequence set forth as SEQ ID NO: 6 and a CDR3 having a sequence set forth as SEQ ID NO: 7.

In some embodiments, the isolated single-domain antibody according to the invention has the sequence set forth as SEQ ID NO: 8.

It should be further noted that the sdAb KB-VWF-008 cross-react with canine VWF, which is of interest for preclinical evaluation and toxicological studies.

TABLE C

Sequences of KB-VWF-011 domains.

| KB-VWF-011 domains | Sequences |
|---|---|
| CDR1 | SEQ ID NO: 9<br>GGTFSNYAMG |
| CDR2 | SEQ ID NO: 10<br>ISRSGHRTDYADSAKG |
| CDR3 | SEQ ID NO: 11<br>RSDWSIATTATSYDY |
| SEQUENCE KB-VWF-011 | SEQ ID NO: 12<br>QVQLVQSGGGLVQAGDSLRLSCAAS GGTFSNYAMG WFRQ TPGKEREFVAR ISRSGHRTDYADSAKG RFTISRDNAKNT VYLQMNSLKPEDTAVYYCAAR SDWSIATTATSYDY WGQG TQVTVSS |

In particular, the invention relates to an isolated single-domain antibody (sdAb) comprising a CDR1 having at least 80%, preferably at least 90%, more preferably at least 95%, even more preferably at least 99% sequence identity with sequence set forth as SEQ ID NO: 9, a CDR2 having at least 80%, preferably at least 90%, more preferably at least 95%, even more preferably at least 99% sequence identity with sequence set forth as SEQ ID NO: 10 and a CDR3 having at least 80%, preferably at least 90%, more preferably at least 95%, even more preferably at least 99% sequence identity with sequence set forth as SEQ ID NO: 11.

In some embodiments, the isolated single-domain antibody according to the invention comprises a CDR1 having a sequence set forth as SEQ ID NO: 9, a CDR2 having a sequence set forth as SEQ ID NO: 10 and a CDR3 having a sequence set forth as SEQ ID NO: 11.

In some embodiments, the isolated single-domain antibody according to the invention has the sequence set forth as SEQ ID NO: 12.

In some embodiments, the single domain antibody is a "humanized" single-domain antibody. As used herein the term "humanized" refers to a single-domain antibody of the invention wherein an amino acid sequence that corresponds to the amino acid sequence of a naturally occurring VHH domain has been "humanized", i.e. by replacing one or more amino acid residues in the amino acid sequence of said naturally occurring VHH sequence (and in particular in the framework sequences) by one or more of the amino acid residues that occur at the corresponding position(s) in a VH domain from a conventional chain antibody from a human being. Methods for humanizing single domain antibodies are well known in the art. Typically, the humanizing substitutions should be chosen such that the resulting humanized single domain antibodies still retain the favorable properties of single-domain antibodies of the invention. The one skilled in the art is able to determine and select suitable humanizing substitutions or suitable combinations of humanizing substitutions.

Chimeric Polypeptides of the Invention

A second aspect of the invention refers to a chimeric polypeptide comprising a polypeptide and at least one single-domain antibody directed against VWF of the invention.

As used herein, the terms "protein" or "polypeptide" refers to a polymer of two or more of the natural amino acids or non-natural amino acids.

A "fusion" or "chimeric" protein or polypeptide comprises a first amino acid sequence linked to a second amino acid sequence with which it is not naturally linked in nature. The amino acid sequences which normally exist in separate proteins can be brought together in the fusion polypeptide. A fusion protein is created, for example, by chemical synthesis, or by creating and translating a polynucleotide in which the polypeptide regions are encoded in the desired relationship. "Fusion" or "chimeric" polypeptides and proteins includes a combination of a first polypeptide chain, e.g., the FVIII protein, with a second polypeptide chain, e.g., a single-domain antibody directed against von VWF D'D3 domain.

In one embodiment, the chimeric polypeptide comprises any polypeptide, in particular therapeutic polypeptide, preferably having a short half-life leading to repeated administration to the patient in need thereof. Such therapeutic polypeptide may be for instance insulin, glucagon, osteoprotegerin (OPG), Angiopoietin-2 (ANGPT2) or furin.

In a particular embodiment, the chimeric polypeptide comprises a clotting factor (also referred as blood coagulation factor).

As used herein, the term "clotting factor," refers to molecules, or analogs thereof naturally occurring or recombinant produced which prevent or decrease the duration of a bleeding episode in a subject. In other words, it means molecules having pro-clotting activity, i.e., are responsible for the conversion of fibrinogen into a mesh of insoluble fibrin causing the blood to coagulate or clot. Clotting factors include factor VIII, prothrombin factors (comprising factor VII, Factor IX, factor X, protein C, protein S, protein Z and prothrombin) and clotting factor V. In a particular embodiment, the chimeric polypeptide according to the invention, wherein the polypeptide is a clotting factor selected from the group consisting of FVII, FVIII, protein C and protein S. Clotting factors of the invention may also be variants of wild-type clotting factors. The term "variants" includes insertions, deletions and substitutions, either conservative or non-conservative, where such changes do not substantially alter the active site, or active domain, which confers the biological activities of the respective clotting factor. Preferably a clotting factor is selected from the group consisting of FVII, FVIII and FX.

In one embodiment, the chimeric polypeptide comprising a polypeptide and at least one single-domain antibody directed against VWF according the invention, wherein said chimeric polypeptide has an increased affinity and/or a reduced dissociation rate constant for VWF comparatively to the wild-type polypeptide.

Without wishing to be bound by theory and knowing that affinity (i.e. affinity for VWF) is defined by Kd=association-rate ($k_{on}$)/dissociation-rate ($k_{off}$), the chimeric polypeptide should have an increased affinity mainly due to a reduced $k_{off}$ as a result of the binding of the single-domain antibody directed against von VWF D'D3 domain to VWF.

In a preferred embodiment, the chimeric polypeptide exhibits a reduced clearance rate and thus an extended half-life when administered to a subject, compared to a corresponding polypeptide not linked to said sdAb directed against VWF and administered to said subject.

As used herein, the term "half-life" refers to a biological half-life of a particular polypeptide in vivo. Half-life may be represented by the time required for half the quantity administered to a subject to be cleared from the circulation and/or other tissues in the animal. When a clearance curve of a given polypeptide is constructed as a function of time, the curve is usually biphasic with a rapid, α-phase and longer β-phase.

Typically, the chimeric polypeptide of the invention comprises at least one single-domain antibody of the invention, which is fused at the N terminal end, at the C terminal end, or both at the N terminal end and at the C terminal end of the therapeutic polypeptide, i.e. so as to provide a fusion protein (eventually via at least one further amino acid sequence).

Alternatively, the chimeric polypeptide of the invention comprises at least one single domain antibody of the invention, which is inserted into the therapeutic polypeptide.

The term "inserted into" as used herein refers to the position of a single-domain antibody directed against von VWF D'D3 domain in a chimeric polypeptide relative to the analogous position in native polypeptide such as mature human FVIII polypeptide. The term refers to the characteristics of the chimeric polypeptide relative to native polypeptide, and do not indicate, imply or infer any methods or process by which the chimeric polypeptide was made. For example, in reference to a chimeric polypeptide provided herein, the phrase "a single-domain antibody directed against von VWF D'D3 domain is inserted downstream of residue 759 of the FVIII polypeptide" means that the chimeric polypeptide comprises a sdAb directed against von VWF D'D3 domain downstream of an amino acid which corresponds to amino acid Arg759 in native human FVIII, e.g., bounded by amino acids corresponding to amino acids Ser760 or Phe761 of native human FVIII. Importantly, to improve exposure of the sdAb in the context of the fusion protein, flexible amino acid linkers (e.g. one or multiple copies of the Gly-Gly-Gly-Ser motif) may be placed N- or C-terminally of each sdAb sequence.

As used herein, the term "insertion site" refers to a position in a polypeptide, such as a FVIII polypeptide, which is immediately upstream of the position at which a heterologous moiety can be inserted. An "insertion site" is specified as a number, the number being the number of the amino acid in said polypeptide to which the insertion site corresponds, which is immediately N-terminal to the position of the insertion.

According to the invention, the polypeptides that comprise a sole single-domain antibody are referred to herein as "monovalent" polypeptides. Polypeptides that comprise or essentially consist of two or more single-domain antibodies according to the invention are referred to herein as "multivalent" polypeptides.

The chimeric polypeptide according to the invention, comprises at least one single-domain antibody of the invention, wherein said single-domain antibody is fused at the N terminal end, at the C terminal end, both at the N terminal end and at the C terminal end of the therapeutic polypeptide or is inserted within the sequence of the therapeutic polypeptide.

In one embodiment, the polypeptide comprises two, three, four, five sdAb directed against VWF. In certain embodiments, two or more single-domain antibodies according to the invention are fused or inserted to the same terminal end or to the same insertion site.

In one embodiment, the polypeptide comprises at least one single-domain antibody of the invention and at least one other binding unit (i.e. directed against another epitope, antigen, target, protein or polypeptide), which is preferably also a single-domain antibody. Such a polypeptide is referred to herein as "multispecific" polypeptide; in opposition to a polypeptide comprising the same single-domain antibodies ("monospecific" polypeptide).

Thus, in some embodiments, the polypeptide of the invention may also provide at least one further binding site directed against any desired protein, polypeptide, antigen, antigenic determinant or epitope. Said binding site is directed against to the same protein, polypeptide, antigen, antigenic determinant or epitope for which the single domain antibody of the invention is directed again, or may be directed against a different protein, polypeptide, antigen, antigenic determinant or epitope) from the single domain antibody of the invention. A "bispecific" polypeptide of the invention is a polypeptide that comprises at least one single-domain antibody directed against a first antigen (e.g. VWF D'D3 domain) and at least one further binding site directed against a second antigen (i.e. different from VWF D'D3 domain).

In some embodiments, the further binding site is directed against a serum protein so that the half-lie of the single domain antibody is increased. Typically, said serum protein is albumin. In some embodiments, the polypeptides comprise a single domain antibody of the invention that is linked to an immunoglobulin domain. For example the polypeptides comprise a single domain antibody of the invention that is linked to an Fc portion (such as a human Fc). Said Fc portion may be useful for increasing the half-life and even the production of the single domain antibody of the invention. For example the Fc portion can bind to serum proteins and thus increases the half-life on the single domain antibody.

In a particular embodiment, the clotting factor is FVIII. The terms "Factor VIII" and "FVIII" are used interchangeably herein. The FVIII protein is divided into 6 structural domains: a triplicated A domain (A1, A2, A3), a carbohydrate-rich and dispensable central domain (B-domain), and a duplicated C domain (C1, C2). In addition, the A1 and A2 domain, the A2 and B-domain and the B and A3 domain are separated by short sequences known as a1, a2 and a3, respectively, which are characterized by the presence of multiple acidic amino acids. The naturally occurring human FVIII protein has an amino acid sequence as shown in GeneBank Accession number NP_000123. "FVIII" includes wild type FVIII as well as variants of wild type FVIII having the procoagulant activity of wild type FVIII. Variants may have deletions, insertions and/or additions compared with the amino acid sequence of wild type FVIII such as mutants with reduced immunogenicity. The term FVIII includes proteolytically processed forms of FVIII. Commercially available therapeutic FVIII products include plasma derived FVIII (pdFVIII) and recombinant FVIII (rFVIII) products, such as the full-length rFVIII (Kogenate Bayer, Advate Baxter, Helixate CSL-Behring) and a B-domain deleted rFVIII (Refacto Wyeth, now marketed as Xyntha by Pfizer).

In certain embodiments, the polypeptide comprises a FVIII polypeptide and at least one sdAb directed against VWF according to the invention, wherein said FVIII polypeptide comprises A1 domain, A2 domain, A3 domain, C1 domain, C2 domain and optionally all or a portion of B domain, and wherein said at least one single-domain antibody directed against VWF is linked to said FVIII polypeptide at (i) the C-terminus of said FVIII polypeptide; (ii) within B domain of said FVIII polypeptide if all or a portion of B domain is present; (iii) within a surface loop of the A1 domain of said FVIII polypeptide; (iv) within a surface loop of the A2 domain of said FVIII polypeptide; (v) within a surface loop of the A3 domain of said FVIII polypeptide; (vi) within the C1 domain of said FVIII polypeptide; or (vii) within the C2 domain of said FVIII polypeptide; wherein said polypeptide exhibits a half-life that is extended when administered to a subject, compared to a corresponding FVIII not linked to said sdAb directed against von VWF and administered to said subject.

In one embodiment, the portion of B domain, is the portion with 1-20 amino acids of B domain (i.e. a portion comprising with the cleavage site of thrombin at position Arg740).

The typical half-life of a human FVIII in humans is several hours (7-21 hours, Van Dijk et al Haematologica 2005 92:494-498). In some embodiments, the chimeric FVIII polypeptide has extended half-life compared to wild type FVIII polypeptide. In certain embodiments, the half-life of the chimeric FVIII polypeptide is extended at least about 1.5 times, at least about 2 times, at least about 2.5 times, at least about 3 times, at least about 4 times, at least about 5 times, at least about 6 times, at least about 7 times, at least about 8 times, at least about 9 times, at least about 10 times, at least about 11 times, or at least about 12 times longer than wild type FVIII.

In a particular embodiment, two sdAb directed against VWF are inserted within the B domain of factor VIII (FVIII-KB13-bv) (SEQ ID NO: 13).

FVIII-KB013-bv

| A1 | a1 | A2 | a2 | KB-vwf-013 | KB-vwf-013 | a3 | A3 | C1 | C2 |

| FVIII-KB13-bv | Sequence |
|---|---|
| Polypeptide | SEQ ID NO: 13 |

```
  1 M Q I E L S T C F F L C L L R F C F S A
 21 T R R Y Y L G A V E L S W D Y M Q S D L
 41 G E L P V D A R F P P R V P K S F P F N
 61 T S V V Y K K T L F V E F T D H L F N I
 81 A K P R P P W M G L L G P T I Q A E V Y
101 D T V V I T L K N M A S H P V S L H A V
121 G V S Y W K A S E G A E Y D D Q T S Q R
141 E K E D D K V F P G G S H T Y V W Q V L
161 K E N G P M A S D P L C L T Y S Y L S H
181 V D L V K D L N S G L I G A L L V C R E
201 G S L A K E K T Q L H K F I L L F A V
221 F D E G K S W H S E T K N S L M Q D R D
241 A A S A R A W P K M H T V N G Y V N R S
261 L P G L I G C H R K S V Y W H V I G M G
281 T T P E V H S I F L E G H T F L V R N H
301 R Q A S L E I S P I T F L T A Q T L L M
321 D L G Q F L L F C H I S S H Q H D G M E
341 A Y V K V D S C P E E P Q L R M K N N E
361 E A E D Y D D D L T D S E M D V V R F D
381 D D N S P S F I Q I R S V A K K H P K T
401 W V H Y I A A E E E D W D Y A P L V L A
421 P D D R S Y K S Q Y L N N G P Q R I G R
441 K Y K K V R F M A Y T D E T F K T R E A
461 I Q H E S G I L G P L L Y G E V G D T L
481 L I I F K N Q A S R P Y N I Y P H G I T
501 D V R P L Y S R R L P K G V K H L K D F
521 P I L P G E I F K Y K W T V T V E D G P
541 T K S D P R C L T R Y Y S S F V N M E R
561 D L A S G L I G P L L I C Y K E S V D Q
581 R G N Q I M S D K R N V I L F S V F D E
601 N R S W Y L T E N I Q R F L P N P A G V
621 Q L E D P E F Q A S N I M H S I N G Y V
641 F D S L Q L S V C L H E V A Y W Y I L S
661 I G A Q T D F L S V F F S G Y T F K H K
681 M V Y E D T L T L F P F S G E T V F M S
```

FVIII-KB013-bv

| A1 | a1 | A2 | a2 | KB-vwf-013 | KB-vwf-013 | a3 | A3 | C1 | C2 |

| FVIII-KB13-bv | Sequence |
|---|---|

```
 701 M E N P G L W I L G C H N S D F R N R G
 721 M T A L L K V S S C D K N T G D Y Y E D
 741 S Y E D I S A Y L L S K N N A I E P R S
 761 F S G G G S Q V Q L V Q S G G G L V Q A
 781 G D S L R L S C A A S G R T F I R Y A M
 801 A W F R Q A P G K E R E F V A A I P Q S
 821 G G R S Y Y A D S V K G R F T I S R D N
 841 A K N T V Y L Q M N S L K P E D T A V Y
 861 S C A A T S T Y Y G R S A Y S S H S G G
 881 Y D Y W G Q G T Q V T V S S G G G S G G
 901 G S G G G S G G G S Q V Q L V Q S G G G
 921 L V Q A G D S L R L S C A A S G R T F I
 941 R Y A M A W F R Q A P G K E R E F V A A
 961 I P Q S G G R S Y Y A D S V K G R F T I
 981 S R D N A K N T V Y L Q M N S L K P E D
1001 T A V Y S C A A T S T Y Y G R S A Y S S
1021 H S G G Y D Y W G Q G T Q V T V S S G G
1041 G S E I T R T T L Q S D Q E E I D Y D D
1061 T I S V E M K K E D F D I Y D E D E N Q
1081 S P R S F Q K K T R H Y F I A A V E R L
1101 W D Y G M S S S P H V L R N R A Q S G S
1121 V P Q F K K V V F Q E F T D G S F T Q P
1141 L Y R G E L N E H L G L L G P Y I R A E
1161 V E D N I M V T F R N Q A S R P Y S F Y
1181 S S L I S Y E E D Q R Q G A E P R K N F
1201 V K P N E T K T Y F W K V Q H H M A P T
1221 K D E F D C K A W A Y F S D V D L E K D
1241 V H S G L I G P L L V C H T N T L N P A
1261 H G R Q V T Q E F A L F F T I F D E T
1281 K S W Y F T E N M E R N C R A P C N I Q
1301 M E D P T F K E N Y R F H A I N G Y I M
1321 D T L P G L V M A Q D Q R I R W Y L L S
1341 M G S N E N I H S I H F S G H V F T V R
1361 K K E E Y K M A L Y N L Y P G V F E T V
1381 E M L P S K A G I W R V E C L I G E H L
1401 H A G M S T L F L V Y S N K C Q T P L G
```

-continued

FVIII-KB013-bv

| FVIII-KB13-bv | Sequence |
|---|---|
| 1421 | M A S G H I R D F Q I T A S G Q Y G Q W |
| 1441 | A P K L A R L H Y S G S I N A W S T K E |
| 1461 | P F S W I K V D L L A P M I I H G I K T |
| 1481 | Q G A R Q K F S S L Y I S Q F I I M Y S |
| 1501 | L D G K K W Q T Y R G N S T G T L M V F |
| 1521 | F G N V D S S G I K H N I F N P P I I A |
| 1541 | R Y I R L H P T H Y S I R S T L R M E W |
| 1561 | M G C D L N S C S M P L G M E S K A I S |
| 1581 | D A Q I T A S S Y F T N M F A T W S P S |
| 1601 | K A R L H L Q G R S N A W R P Q V N N P |
| 1621 | K E W L Q V D F Q K T M K V T G V T T Q |
| 1641 | G V K S L L T S M Y V K E F L I S S S Q |
| 1661 | D G H Q W T L F F Q N G K V K V F Q G N |
| 1681 | Q D S F T P V V N S L D P P L L T R Y L |
| 1701 | R I H P Q S W V H Q I A L R M E V L G C |
| 1721 | E A Q D L Y * |

Italic: signal peptide, not present in the protein that circulates in plasma
Underlined: flexible linkers connecting the various elements of the fusion protein
Bold: sequence of KB-VWF-013

In a particular embodiment, two sdAb directed against VWF are inserted within the B-domain of FVIII (FVIII_KB0013bv (6GGGS)) (SEQ ID NO: 16). Linker between sdAb sequence and FVIII light chain contains 6 GGGS-sequences instead of 1.

TABLE E

Sequences of FVIII-KB13-bv (6GGGS)

| FVIII_KB0013 bv(6GGGS) | Sequence |
|---|---|
| Polypeptide | SEQ ID NO: 16<br>MQIELSTCFFLCLLRFCFSATRRYYLGAVELSWDYMQSDLGELPVD<br>ARFPPRVPKSFPFNTSVVYKKTLFVEFTDHLFNIAKPRPPWMGLLGP<br>TIQAEVYDTVVITLKNMASHPVSLHAVGVSYWKASEGAEYDDQTS<br>QREKEDDKVFPGGSHTYVWQVLKENGPMASDPLCLTYSYLSHVD<br>LVKDLNSGLIGALLVCREGSLAKEKTQTLHKFILLFAVFDEGKSWH<br>SETKNSLMQDRDAASARAWPKMHTVNGYVNRSLPGLIGCHRKSV<br>YWHVIGMGTTPEVHSIFLEGHTFLVRNHRQASLEISPITFLTAQTLL<br>MDLGQFLLFCHISSHQHDGMEAYVKVDSCPEEPQLRMKNNEEAED<br>YDDDLTDSEMDVVRFDDDNSPSFIQIRSVAKKHPKTWVHYIAAEEE<br>DWDYAPLVLAPDDRSYKSQYLNNGPQRIGRKYKKVRFMAYTDET<br>FKTREAIQHESGILGPLLYGEVGDTLLIIFKNQASRPYNIYPHGITDV<br>RPLYSRRLPKGVKHLKDFPILPGEIFKYKWTVTVEDGPTKSDPRCLT<br>RYYSSFVNMERDLASGLIGPLLICYKESVDQRGNQIMSDKRNVILFS<br>VFDENRSWYLTENIQRFLPNPAGVQLEDPEFQASNIMHSINGYVFD<br>SLQLSVCLHEVAYWYILSIGAQTDFLSVFFSGYTFKHKMVYEDTLT<br>LFPFSGETVFMSMENPGLWILGCHNSDFRNRGMTALLKVSSCDKN<br>TGDYYEDSYEDISAYLLSKNNAIEPRSF*SGGGS***QVQLVQSGGGLV**<br>QAGDSLRLSCAASGRTFIRYAMAWFRQAPGKEREFVAAIPQSG<br>GRSYYADSVKGRFTISRDNAKNTVYLQMNSLKPEDTAVYSCAA<br>TSTYYGRSAYSSHSGGYDYWGQGTQVTVSS*GGGSGGGSGGGSG* |

TABLE E-continued

Sequences of FVIII-KB13-bv (6GGGS)

| FVIII_KB0013 bv(6GGGS) | Sequence |
|---|---|
| | *GGS*__QVQLVQSGGGLVQAGDSLRLSCAASGRTFIRYAMAWFRQ__ __APGKEREFVAAIPQSGGRSYYADSVKGRFTISRDNAKNTVYLQ__ __MNSLKPEDTAVYSCAATSTYYGRSAYSSHSGGYDYWGQGTQV__ __TVSS__*GGGSGGGSGGGSGGGSGGGSGGGS*EITRTTLQSDQEEIDYDD TISVEMKKEDFDIYDEDENQSPRSFQKKTRHYFIAAVERLWDYGMS SSPHVLRNRAQSGSVPQFKKVVFQEFTDGSFTQPLYRGELNEHLGL LGPYIRAEVEDNIMVTFRNQASRPYSFYSSLISYEEDQRQGAEPRKN FVKPNETKTYFWKVQHHMAPTKDEFDCKAWAYFSDVDLEKDVHS GLIGPLLVCHTNTLNPAHGRQVTVQEFALFFTIFDETKSWYFTENM ERNCRAPCNIQMEDPTFKENYRFHAINGYIMDTLPGLVMAQDQRIR WYLLSMGSNENIHSIHFSGHVFTVRKKEEYKMALYNLYPGVFETV EMLPSKAGIWRVECLIGEHLHAGMSTLFLVYSNKCQTPLGMASGHI RDFQITASGQYGQWAPKLARLHYSGSINAWSTKEPFSWIKVDLLAP MIIHGIKTQGARQKFSSLYISQFIIMYSLDGKKWQTYRGNSTGTLM VFFGNVDSSGIKHNIFNPPIIARYIRLHPTHYSIRSTLRMEWMGCDL NSCSMPLGMESKAISDAQITASSYFTNMFATWSPSKARLHLQGRSN AWRPQVNNPKEWLQVDFQKTMKVTGVTTQGVKSLLTSMYVKEF LISSSQDGHQWTLFFQNGKVKVFQGNQDSFTPVVNSLDPPLLTRYL RIHPQSWVHQIALRMEVLGCEAQDLY* |

Italic: GGGS-linker
Bold: sequence KB-VWF-013

In a particular embodiment, two sdAb directed against VWF are inserted within the B-domain of FVIII (FVIII_KB0013bv (6GGGS)_Y1680F) (SEQ ID NO: 17). Linker between sdAb sequence and FVIII light chain contains 6 GGGS-sequences instead of 1. The Y1680F mutation to avoid natural binding of FVIII to VWF (binding is only mediated by sdAb).

TABLE F

Sequences of FVIII_KB0013bv(6GGGS)_Y1680F

| FVIII_KB0013 bv(6GGGS)_Y1680F | Sequence |
|---|---|
| Polypeptide | SEQ ID NO: 17 MQIELSTCFFLCLLRFCFSATRRYYLGAVELSWDYMQSDLGELPVD ARFPPRVPKSFPFNTSVVYKKTLFVEFTDHLFNIAKPRPPWMGLLGP TIQAEVYDTVVITLKNMASHPVSLHAVGVSYWKASEGAEYDDQTS QREKEDDKVFPGGSHTYVWQVLKENGPMASDPLCLTYSYLSHVD LVKDLNSGLIGALLVCREGSLAKEKTQTLHKFILLFAVFDEGKSWH SETKNSLMQDRDAASARAWPKMHTVNGYVNRSLPGLIGCHRKSV YWHVIGMGTTPEVHSIFLEGHTFLVRNHRQASLEISPITFLTAQTLL MDLGQFLLFCHISSHQHDGMEAYVKVDSCPEEPQLRMKNNEEAED YDDDLTDSEMDVVRFDDDNSPSFIQIRSVAKKHPKTWVHYIAAEEE DWDYAPLVLAPDDRSYKSQYLNNGPQRIGRKYKKVRFMAYTDET FKTREAIQHESGILGPLLYGEVGDTLLIIFKNQASRPYNIYPHGITDV RPLYSRRLPKGVKHLKDFPILPGEIFKYKWTVTVEDGPTKSDPRCLT RYYSSFVNMERDLASGLIGPLLICYKESVDQRGNQIMSDKRNVILFS VPDENRSWYLTENIQRFLPNPAGVQLEDPEFQASNIMHSINGYVFD SLQLSVCLHEVAYWYILSIGAQTDFLSVFFSGYTFKHKMVYEDTLT LFPPFSGETVFMSMENPGLWILGCHNSDFRNRGMTALLKVSSCDKN TGDYYEDSYEDISAYLLSKNNAIEPRSFS*GGGS*__QVQLVQSGGGLV__ __QAGDSLRLSCAASGRTFIRYAMAWFRQAPGKEREFVAAIPQSG__ __GRSYYADSVKGRFTISRDNAKNTVYLQMNSLKPEDTAVYSCAA__ __TSTYYGRSAYSSHSGGYDYWGQGTQVTVSS__*GGGSGGGSGGGSG GGS*__QVQLVQSGGGLVQAGDSLRLSCAASGRTFIRYAMAWFRQ__ __APGKEREFVAAIPQSGGRSYYADSVKGRFTISRDNAKNTVYLQ__ __MNSLKPEDTAVYSCAATSTYYGRSAYSSHSGGYDYWGQGTQV__ __TVSS__*GGGSGGGSGGGSGGGSGGGSGGGS*EITRTTLQSDQEEIDYDD TISVEMKKEDFDIFDEDENQSPRSFQKKTRHYFIAAVERLWDYGMS SSPHVLRNRAQSGSVPQFKKVVFQEFTDGSFTQPLYRGELNEHLGL LGPYIRAEVEDNIMVTFRNQASRPYSFYSSLISYEEDQRQGAEPRKN FVKPNETKTYFWKVQHHMAPTKDEFDCKAWAYFSDVDLEKDVHS GLIGPLLVCHTNTLNPAHGRQVTVQEFALFFTIFDETKSWYFTENM ERNCRAPCNIQMEDPTFKENYRFHAINGYIMDTLPGLVMAQDQRIR WYLLSMGSNENIHSIHFSGHVFTVRKKEEYKMALYNLYPGVFETV EMLPSKAGIWRVECLIGEHLHAGMSTLFLVYSNKCQTPLGMASGHI RDFQITASGQYGQWAPKLARLHYSGSINAWSTKEPFSWIKVDLLAP MIIHGIKTQGARQKFSSLYISQFIIMYSLDGKKWQTYRGNSTGTLM VFFGNVDSSGIKHNIFNPPIIARYIRLHPTHYSIRSTLRMEWMGCDL NSCSMPLGMESKAISDAQITASSYFTNMFATWSPSKARLHLQGRSN AWRPQVNNPKEWLQVDFQKTMKVTGVTTQGVKSLLTSMYVKEF |

TABLE F-continued

Sequences of FVIII_KB0013bv(6GGGS)_Y1680F

| FVIII_KB0013 bv(6GGGS)_Y1680F | Sequence |
|---|---|
| | LISSSQDGHQWTLFFQNGKVKVFQGNQDSFTPVVNSLDPPLLTRYL RIHPQSWVHQIALRMEVLGCEAQDLY* |

Italic: GGGS-linker
Bold: sequence KB-VWF-013
Bold underline: mutation p.Y1680F

In a particular embodiment, two sdAb directed against VWF are inserted at C terminus of FVIII (FVIII_BD_Cter-0013bv) (SEQ ID NO: 18).

TABLE G

Sequences of FVIII_BD_Cter-0013bv

| FVIII_BD_Cter-0013bv | Sequence |
|---|---|
| Polypeptide | SEQ ID NO: 18<br>MQIELSTCFFLCLLRFCFSATRRYYLGAVELSWDYMQSDLGELPVD<br>ARFPPRVPKSFPFNTSVVYKKTLFVEFTDHLFNIAKPRPPWMGLLGP<br>TIQAEVYDTVVITLKNMASHPVSLHAVGVSYWKASEGAEYDDQTS<br>QREKEDDKVFPGGSHTYVWQVLKENGPMASDPLCLTYSYLSHVD<br>LVKDLNSGLIGALLVCREGSLAKEKTQTLHKFILLFAVFDEGKSWH<br>SETKNSLMQDRDAASARAWPKMHTVNGYVNRSLPGLIGCHRKSV<br>YWHVIGMGTTPEVHSIFLEGHTFLVRNHRQASLEISPITFLTAQTLL<br>MDLGQFLLFCHISSHQHDGMEAYVKVDSCPEEPQLRMKNNEEAED<br>YDDDLTDSEMDVVRFDDDNSPSFIQIRSVAKKHPKTWVHYIAAEEE<br>DWDYAPLVLAPDDRSYKSQYLNNGPQRIGRKYKKVRFMAYTDET<br>FKTREAIQHESGILGPLLYGEVGDTLLIIFKNQASRPYNIYPHGITDV<br>RPLYSRRLPKGVKHLKDFPILPGEIFKYKWTVTVEDGPTKSDPRCLT<br>RYYSSFVNMERDLASGLIGPLLICYKESVDQRGNQIMSDKRNVILFS<br>VFDENRSWYLTENIQRFLPNPAGVQLEDPEFQASNIMHSINGYVFD<br>SLQLSVCLHEVAYWYILSIGAQTDFLSVFFSGYTFKHKMVYEDTLT<br>LFPFSGETVFMSMENPGLWILGCHNSDFRNRGMTALLKVSSCDKN<br>TGDYYEDSYEDISAYLLSKNNAIEPRSFSQNPPVLKRHQREITRTTL<br>QSDQEEIDYDDTISVEMKKEDFDIYDEDENQSPRSFQKKTRHYFIAA<br>VERLWDYGMSSSPHVLRNRAQSGSVPQFKKVVFQEFTDGSFTQPL<br>YRGELNEHLGLLGPYIRAEVEDNIMVTFRNQASRPYSFYSSLISYEE<br>DQRQGAEPRKNFVKPNETKTYFWKVQHHMAPTKDEFDCKAWAY<br>FSDVDLEKDVHSGLIGPLLVCHTNTLNPAHGRQVTVQEFALFFTIFD<br>ETKSWYFTENMERNCRAPCNIQMEDPTFKENYRFHAINGYIMDTLP<br>GLVMAQDQRIRWYLLSMGSNENIHSIHFSGHVFTVRKKEEYKMAL<br>YNLYPGVFETVEMLPSKAGIWRVECLIGEHLHAGMSTLFLVYSNK<br>CQTPLGMASGHIRDFQITASGQYGQWAPKLARLHYSGSINAWSTK<br>EPFSWIKVDLLAPMIIHGIKTQGARQKFSSLYISQFIIMYSLDGKKW<br>QTYRGNSTGTLMVFFGNVDSSGIKHNIFNPPIIARYIRLHPTHYSIRS<br>TLRMEWMGCDLNSCSMPLGMESKAISDAQITASSYFTNMFATWSP<br>SKARLHLQGRSNAWRPQVNNPKEWLQVDFQKTMKVTGVTTQGV<br>KSLLTSMYVKEFLISSSQDGHQWTLFFQNGKVKVFQGNQDSFTPV<br>VNSLDPPLLTRYLRIHPQSWVHQIALRMEVLGCEAQDLY<u>LTPRGVR</u><br><u>L</u>*GGGSGGGSGGGSGGGS*QVQLVQSGGGLVQAGDSLRLSCAASG<br>RTFIRYAMAWFRQAPGKEREFVAAIPQSGGRSYYADSVKGRFT<br>ISRDNAKNTVYLQMNSLKPEDTAVYSCAATSTYYGRSAYSSHSG<br>GYDYWGQGTQVTVSS*GGGSGGGSGGGSGGGS*QVQLVQSGGGL<br>VQAGDSLRLSCAASGRTFIRYAMAWFRQAPGKEREFVAAIPQS<br>GGRSYYADSVKGRFTISRDNAKNTVYLQMNSLKPEDTAVYSCA<br>ATSTYYGRSAYSSHSGGYDYWGQGTQVTVSS* |

Italic: GGGS-linker
Bold: sequence KB-VWF-013
Underline: thrombin-cleavage site

In a particular embodiment, two sdAb directed against VWF are inserted at C terminus of FVIII (FVIII_BD_Cter-0013bv_Y1680F) (SEQ ID NO: 19). The Y1680F mutation to avoid natural binding of FVIII to VWF (binding is only mediated by sdAb).

TABLE H

Sequences of FVIII_BD_Cter-0013bv_Y1680F

| FVIII_BD_Cter-0013bv_Y1680F | Sequence |
|---|---|
| Polypeptide | SEQ ID NO: 19<br>MQIELSTCFFLCLLRFCFSATRRYYLGAVELSWDYMQSDLGELP<br>VDARFPPRVPKSFPFNTSVVYKKTLFVEFTDHLFNIAKPRPPWM<br>GLLGPTIQAEVYDTVVITLKNMASHPVSLHAVGVSYWKASEGA<br>EYDDQTSQREKEDDKVFPGGSHTYVWQVLKENGPMASDPLCLT<br>YSYLSHVDLVKDLNSGLIGALLVCREGSLAKEKTQTLHKFILLFA<br>VFDEGKSWHSETKNSLMQDRDAASARAWPKMHTVNGYVNRS<br>LPGLIGCHRKSVYWHVIGMGTTPEVHSIFLEGHTFLVRNHRQAS<br>LEISPITFLTAQTLLMDLGQFLLFCHISSSHQHDGMEAYVKVDSCP<br>EEPQLRMKNNEEAEDYDDDLTDSEMDVVRFDDDNSPSFIQIRSV<br>AKKHPKTWVHYIAAEEEDWDYAPLVLAPDDRSYKSQYLNNGP<br>QRIGRKYKKVRFMAYTDETFKTREAIQHESGILGPLLYGEVGDT<br>LLIIFKNQASRPYNIYPHGITDVRPLYSRRLPKGVKHLKDFPILPG<br>EIFKYKWTVTVEDGPTKSDPRCLTRYYSSFVNMERDLASGLIGP<br>LLICYKESVDQRGNQIMSDKRNVILFSVFDENRSWYLTENIQRFL<br>PNPAGVQLEDPEFQASNIMHSINGYVFDSLQLSVCLHEVAYWYI<br>LSIGAQTDFLSVFFSGYTFKHKMVYEDTLTLFPFSGETVFMSME<br>NPGLWILGCHNSDFRNRGMTALLKVSSCDKNTGDYYEDSYEDI<br>SAYLLSKNNAIEPRSFSQNPPVLKRHQREITRTTLQSDQEEIDYD<br>DTISVEMKKEDFDIFDEDENQSPRSFQKKTRHYFIAAVERLWDY<br>GMSSSPHVLRNRAQSGSVPQFKKVVFQEFTDGSFTQPLYRGELN<br>EHLGLLGPYIRAEVEDNIMVTFRNQASRPYSFYSSLISYEEDQRQ<br>GAEPRKNFVKPNETKTYFWKVQHHMAPTKDEFDCKAWAYFSD<br>VDLEKDVHSGLIGPLLVCHTNTLNPAHGRQVTVQEFALFFTIFDE<br>TKSWYFTENMERNCRAPCNIQMEDPTFKENYRFHAINGYIMDTL<br>PGLVMAQDQRIRWYLLSMGSNENIHSIHFSGHVFTVRKKEEYK<br>MALYNLYPGVFETVEMLPSKAGIWRVECLIGEHLHAGMSTLFL<br>VYSNKCQTPLGMASGHIRDFQITASGQYGQWAPKLARLHYSGSI<br>NAWSTKEPFSWIKVDLLAPMIIHGIKTQGARQKFSSLYISQFIIMY<br>SLDGKKWQTYRGNSTGTLMVFFGNVDSSGIKHNIFNPPIIARYIR<br>LHPTHYSIRSTLRMEWMGCDLNSCSMPLGMESKAISDAQITASS<br>YFTNMFATWSPSKARLHLQGRSNAWRPQVNNPKEWLQVDFQK<br>TMKVTGVTTQGVKSLLTSMYVKEFLISSSQDGHQWTLFFQNGK<br>VKVFQGNQDSFTPVVNSLDPPLLTRYLRIHPQSWVHQIALRMEV<br>LGCEAQDLYL<u>TPRGVRL</u>*GGGSGGGSGGGSGGGS*QVQLVQSGG<br>GLVQAGDSLRLSCAASGRTFIRYAMAWFRQAPGKEREFVAA<br>IPQSGGRSYYADSVKGRFTISRDNAKNTVYLQMNSLKPEDTA<br>VYSCAATSTYYGRSAYSSHSGGYDYWGQGTQVTVSS*GGGSG*<br>*GGSGGGSGGGS*QVQLVQSGGGLVQAGDSLRLSCAASGRTFIR<br>YAMAWFRQAPGKEREFVAAIPQSGGRSYYADSVKGRFTISR<br>DNAKNTVYLQMNSLKPEDTAVYSCAATSTYYGRSAYSSHSG<br>GYDYWGQGTQVTVSS\* |

Italic: GGGS-linker
Bold: sequence KB-VWF-013
Underline: thrombin-cleavage site
Bold underline: mutation p.Y1680F In a particular embodiment, two sdAb directed against VWF are inserted within the B-domain of FVIII, while two sdAb are inserted at the C-terminus (FVIII_KB0013bv_Cter-0013bv) (SEQ ID NO: 20).

TABLE I

Sequences of FVIII_KB0013bv_Cter-0013bv

| FVIII_KB0013bv_Cter-0013bv | Sequence |
|---|---|
| Polypeptide | SEQ ID NO: 20<br>MQIELSTCFFLCLLRFCFSATRRYYLGAVELSWDYMQSDLGELP<br>VDARFPPRVPKSFPFNTSVVYKKTLFVEFTDHLFNIAKPRPPWM<br>GLLGPTIQAEVYDTVVITLKNMASHPVSLHAVGVSYWKASEGA<br>EYDDQTSQREKEDDKVFPGGSHTYVWQVLKENGPMASDPLCLT<br>YSYLSHVDLVKDLNSGLIGALLVCREGSLAKEKTQTLHKFILLFA<br>VFDEGKSWHSETKNSLMQDRDAASARAWPKMHTVNGYVNRS<br>LPGLIGCHRKSVYWHVIGMGTTPEVHSIFLEGHTFLVRNHRQAS |

TABLE I-continued

Sequences of FVIII_KB0013bv_Cter-0013bv

| FVIII_KB0013bv_Cter-0013bv | Sequence |
|---|---|
| | LEISPITFLTAQTLLMDLGQFLLFCHISSHQHDGMEAYVKVDSCP<br>EEPQLRMKNNEEAEDYDDDLTDSEMDVVRFDDDNSPSFIQIRSV<br>AKKHPKTWVHYIAAEEEDWDYAPLVLAPDDRSYKSQYLNNGP<br>QRIGRKYKKVRFMAYTDETFKTREAIQHESGILGPLLYGEVGDT<br>LLIIFKNQASRPYNIYPHGITDVRPLYSRRLPKGVKHLKDFPILPG<br>EIFKYKWTVTVEDGPTKSDPRCLTRYYSSFVNMERDLASGLIGP<br>LLICYKESVDQRGNQIMSDKRNVILFSVFDENRSWYLTENIQRFL<br>PNPAGVQLEDPEFQASNIMHSINGYVFDSLQLSVCLHEVAYWYI<br>LSIGAQTDFLSVFFSGYTFKHKMVYEDTLTLFPFSGETVFMSME<br>NPGLWILGCHNSDFRNRGMTALLKVSSCDKNTGDYYEDSYEDI<br>SAYLLSKNNAIEPRSF*GGGS*QVQLVQSGGGLVQAGDSLRLSC<br>AASGRTFIRYAMAWFRQAPGKEREFVAAIPQSGGRSYYADS<br>VKGRFTISRDNAKNTVYLQMNSLKPEDTAVYSCAATSTYYG<br>RSAYSSHSGGYDYWGQGTQVTVSS*GGGSGGGSGGGSGGGS*QV<br>QLVQSGGGLVQAGDSLRLSCAASGRTFIRYAMAWFRQAPG<br>KEREFVAAIPQSGGRSYYADSVKGRFTISRDNAKNTVYLQMN<br>SLKPEDTAVYSCAATSTYYGRSAYSSHSGGYDYWGQGTQVT<br>VSS*GGGS*EITRTTLQSDQEEIDYDDTISVEMKKEDFDIYDEDENQ<br>SPRSFQKKTRHYFIAAVERLWDYGMSSSPHVLRNRAQSGSVPQF<br>KKVVFQEFTDGSFTQPLYRGELNEHLGLLGPYIRAEVEDNIMVT<br>FRNQASRPYSFYSSLISYEEDQRQGAEPRKNFVKPNETKTYFWK<br>VQHHMAPTKDEFDCKAWAYFSDVDLEKDVHSGLIGPLLVCHTN<br>TLNPAHGRQVTVQEFALFFTIFDETKSWYFTENMERNCRAPCNI<br>QMEDPTFKENYRFHAINGYIMDTLPGLVMAQDQRIRWYLLSMG<br>SNENIHSIHFSGHVFTVRKKEEYKMALYNLYPGVFETVEMLPSK<br>AGIWRVECLIGEHLHAGMSTLFLVYSNKCQTPLGMASGHIRDFQ<br>ITASGQYGQWAPKLARLHYSGSINAWSTKEPFSWIKVDLLAPMII<br>HGIKTQGARQKFSSLYISQFIIMYSLDGKKWQTYRGNSTGTLMV<br>FFGNVDSSGIKHNIFNPPIIARYIRLHPTHYSIRSTLRMEWMGCDL<br>NSCSMPLGMESKAISDAQITASSYFTNMFATWSPSKARLHLQGR<br>SNAWRPQVNNPKEWLQVDFQKTMKVTGVTTQGVKSLLTSMYV<br>KEFLISSSQDGHQWTLFIQNGKVKVFQGNQDSFTPVVNSLDPPL<br>LTRYLRIHPQSWVHQIALRMEVLGCEAQDL<u>YLTPRGVRL</u>*GGGS*<br>*GGGSGGGSGGGS*QVQLVQSGGGLVQAGDSLRLSCAASGRTFI<br>RYAMAWFRQAPGKEREFVAAIPQSGGRSYYADSVKGRFTIS<br>RDNAKNTVYLQMNSLKPEDTAVYSCAATSTYYGRSAYSSHS<br>GGYDYWGQGTQVTVSS*GGGSGGGSGGGSGGGS*QVQLVQSGG<br>GLVQAGDSLRLSCAASGRTFIRYAMAWFRQAPGKEREFVAA<br>IPQSGGRSYYADSVKGRFTISRDNAKNTVYLQMNSLKPEDTA<br>VYSCAATSTYYGRSAYSSHSGGYDYWGQGTQVTVSS*\* |

Italic: GGGS-linker
Bold: sequence KB-VWF-013
Underline: thrombin-cleavage site

In a particular embodiment, two sdAb directed against VWF are inserted within the B-domain of FVIII, while two sdAb are inserted at the C-terminus (FVIII_KB0013bv_Cter-0013bv_Y1680F) (SEQ ID NO: 21). The Y1680F mutation allows to avoid natural binding of FVIII to VWF (binding is only mediated by sdAb). C-terminal thrombin cleavage site allows to release sdAb upon FVIII activation.

TABLE J

Sequences of FVIII_KB0013bv_Cter-0013bv_Y1680F

| FVIII_KB0013bv_Cter-0013bv_Y1680F | Sequence |
|---|---|
| Polypeptide | SEQ ID NO: 21<br>MQIELSTCFFLCLLRFCFSATRRYYLGAVELSWDYMQSDLGELP<br>VDARFPPRVPKSFPFNTSVVYKKTLFVEFTDHLFNIAKPRPPWM<br>GLLGPTIQAEVYDTVVITLKNMASHPYSLHAVGYSYWKASEGA<br>EYDDQTSQREKEDDKVFPGGSHTYVWQVLKENGPMASDPLCLT<br>YSYLSHVDLVKDLNSGLIGALLVCREGSLAKEKTQTLHKFILLFA<br>VFDEGKSWHSETKNSLMQDRDAASARAWPKMHTVNGYVNRS<br>LPGLIGCHRKSVYWHVIGMGTTPEVHSIFLEGHTFLVRNHRQAS<br>LEISPITFLTAQTLLMDLGQFLLFCHISSHQHDGMEAYVKVDSCP<br>EEPQLRMKNNEEAEDYDDDLTDSEMDVVRFDDDNSPSFIQIRSV<br>AKKHPKTWVHYIAAEEEDWDYAPLVLAPDDRSYKSQYLNNGP<br>QRIGRKYKKVRFMAYTDETFKTREAIQHESGILGPLLYGEVGDT<br>LLIIFKNQASRPYNIYPHGITDVRPLYSRRLPKGVKHLKDFPILPG<br>EIFKYKWTVTVEDGPTKSDPRCLTRYYSSFVNMERDLASGLIGP<br>LLICYKESVDQRGNQIMSDKRNVILFSVFDENRSWYLTENIQRFL<br>PNPAGVQLEDPEFQASNIMHSINGYVFDSLQLSVCLHEVAYWYI |

TABLE J-continued

Sequences of FVIII_KB0013bv_Cter-0013bv_Y1680F

| FVIII_KB0013bv_Cter-0013bv_Y1680F | Sequence |
|---|---|
| | LSIGAQTDFLSVFFSGYTFKHKMVYEDTLTLFPPFSGETVFMSME<br>NPGLWILGCHNSDFRNRGMTALLKVSSCDKNTGDYYEDSYEDI<br>SAYLLSKNNAIEPRSF*SGGGS*QVQLVQSGGGLVQAGDSLRLSC<br>AASGRTFIRYAMAWFRQAPGKEREFVAAIPQSGGRSYYADS<br>VKGRFTISRDNAKNTVYLQMNSLKPEDTAVYSCAATSTYYG<br>RSAYSSHSGGYDYWGQGTQVTVSSGGSGGGSGGGSGGGSQV<br>QLVQSGGGLVQAGDSLRLSCAASGRTFIRYAMAWFRQAPG<br>KEREFVAAIPQSGGRSYYADSVKGRFTISRDNAKNTVYLQMN<br>SLKPEDTAVYSCAATSTYYGRSAYSSHSGGYDYWGQGTQVT<br>VSS*GGGS*EITRTTLQSDQEEIDYDDTISVEMKKEDFDIFDEDENQ<br>SPRSFQKKTRHYFIAAVERLWDYGMSSSPHVLRNRAQSGSVPQF<br>KKVVFQEFTDGSFTQPLYRGELNEHLGLLGPYIRAEVEDNIMVT<br>FRNQASRPYSFYSSLISYEEDQRQGAEPRKNFVKPNETKTYFWK<br>VQHHMAPTKDEFDCKAWAYFSDVDLEKDVHSGLIGPLLVCHTN<br>TLNPAHGRQVTVQEFALFFTIFDETKSWYFTENMERNCRAPCNI<br>QMEDPTFKENYRFHAINGYIMDTLPGLVMAQDQRIRWYLLSMG<br>SNENIHSIHFSGHVFTVRKKEEYKMALYNLYPGVFETVEMLPSK<br>AGIWRVECLIGEHLHAGMSTLFLVYSNKCQTPLGMASGHIRDFQ<br>ITASGQYGQWAPKLARLHYSGSINAWSTKEPFSWIKVDLLAPMII<br>HGIKTQGARQKFSSLYISQFIIMYSLDGKKWQTYRGNSTGTLMV<br>FFGNVDSSGIKHNIFNPPIIARYIRLHPTHYSIRSTLRMEWMGCDL<br>NSCSMPLGMESKAISDAQITASSYFTNMFATWSPSKARLHLQGR<br>SNAWRPQVNNPKEWLQVDFQKTMKVTGVTTQGVKSLLTSMYV<br>KEFLISSSQDGHQWTFFQNGKVKVFQGNQDSFTPVVNSLDPPL<br>LTRYLRIHPQSWVHQIALRMEVLGCEAQDLY<u>LTPRGVRL</u>*GGGS<br>GGGSGGGSGGGS*QVQLVQSGGGLVQAGDSLRLSCAASGRTFI<br>RYAMAWFRQAPGKEREFVAAIPQSGGRSYYADSVKGRFTIS<br>RDNAKNTVYLQMNSLKPEDTAVYSCAATSTYYGRSAYSSHS<br>GGYDYWGQGTQVTVSS*GGGSGGGSGGGSGGGS*QVQLVQSGG<br>GLVQAGDSLRLSCAASGRTFIRYAMAWFRQAPGKEREFVAA<br>IPQSGGRSYYADSVKGRFTISRDNAKNTVYLQMNSLKPEDTA<br>VYSCAATSTYYGRSAYSSHSGGYDYWGQGTQVTVSS**\* |

Italic: GGGS-linker
Bold: sequence KB-VWF-013
Underline: thrombin-cleavage site
Bold underline: mutation p.Y1680F In a particular embodiment, two sdAb directed against VWF are inserted within the B-domain of FVIII, while two sdAb are inserted at the C-terminus (FVIII_KB0013bv (6GGGS)_Cter-0013bv) (SEQ ID NO: 22). Linker between sdAb sequence and FVIII light chain contains 6 GGGS-sequences instead of 1. The C-terminal thrombin cleavage site allows to release sdAb upon FVIII activation.

TABLE K

Sequences of FVIII_KB0013bv(6GGGS)_Cter-0013bv

| FVIII_KB0013bv (6GGGS)_Cter-0013bv | Sequence |
|---|---|
| Polypeptide | SEQ ID NO: 22<br>MQIELSTCFFLCLLRFCFSATRRYYLGAVELSWDYMQSDLGELP<br>VDARFPPRVPKSFPFNTSVVYKKTLFVEFTDHLFNIAKPRPPWM<br>GLLGPTIQAEVYDTVVITLKNMASHPVSLHAVGVSYWKASEGA<br>EYDDQTSQREKEDDKVPPGGSHTYVWQVLKENGPMASDPLCLT<br>YSYLSHVDLVKDLNSGLIGALLVCREGSLAKEKTQTLHKFILLFA<br>VFDEGKSWHSETKNSLMQDRDAASARAWPKMHTVNGYVNRS<br>LPGLIGCHRKSVYWHVIGMGTTPEVHSIFLEGHTFLVRNHRQAS<br>LEISPITFLTAQTLLMDLGQFLLFCHISSHQHDGMEAYVKVDSCP<br>EEPQLRMKNNEEAEDYDDDLTDSEMDVVRFDDDNSPSFIQIRSV<br>AKKHPKTWVHYIAAEEEDWDYAPLVLAPDDRSYKSQYLNNGP<br>QRIGRKYKKVRFMAYTDETFKTREAIQHESGILGPLLYGEVGDT<br>LLIIFKNQASRPYNIYPHGITDVRPLYSRRLPKGVKHLKDFPILPG<br>EIFKYKWTVTVEDGPTKSDPRCLTRYYSSFVNMERDLASGLIGP<br>LLICYKESVDQRGNQIMSDKRNVILFSVFDENRSWYLTENIQRFL<br>PNPAGVQLEDPEFQASNIMHSINGYVFDSLQLSVCLHEVAYWYI<br>LSIGAQTDFLSVFFSGYTFKHKMVYEDTLTLFPPFSGETVFMSME<br>NPGLWILGCHNSDFRNRGMTALLKVSSCDKNTGDYYEDSYEDI<br>SAYLLSKNNAIEPRSF*SGGGS*QVQLVQSGGGLVQAGDSLRLSC<br>AASGRTFIRYAMAWFRQAPGKEREFVAAIPQSGGRSYYADS<br>VKGRFTISRDNAKNTVYLQMNSLKPEDTAVYSCAATSTYYG<br>RSAYSSHSGGYDYWGQGTQVTVSS*GGGSGGGSGGGSGGGSQV** |

TABLE K-continued

Sequences of FVIII_KB0013bv(6GGGS)_Cter-0013bv

| FVIII_KB0013bv (6GGGS)_Cter-0013bv | Sequence |
|---|---|
| | QLVQSGGGLVQAGDSLRLSCAASGRTFIRYAMAWFRQAPG KEREFVAAIPQSGGRSYYADSVKGRFTISRDNAKNTVYLQMN SLKPEDTAVYSCAATSTYYGRSAYSSHSGGYDYWGQGTQVT VSS*GGGSGGGSGGGSGGGSGGGSGGGS*EITRTTLQSDQEEIDYDD TISVEMKKEDFDIYDEDENQSPRSFQKKTRHYFIAAVERLWDYG MSSSPHVLRNRAQSGSVPQFKKVVFQEFTDGSFTQPLYRGELNE HLGLLGPYIRAEVEDNIMVTFRNQASRPYSFYSSLISYEEDQRQG AEPRKNFVKPNETKTYFWKVQHHMAPTKDEFDCKAWAYFSDV DLEKDVHSGLIGPLLVCHTNTLNPAHGRQVTVQEFALFFTIFDET KSWYFTENMERNCRAPCNIQMEDPTFKENYRFHAINGYIMDTLP GLVMAQDQRIRWYLLSMGSNENIHSIHFSGHVFTVRKKEEYKM ALYNLYPGVFETVEMLPSKAGIWRVECLIGEHLHAGMSTLFLVY SNKCQTPLGMASGHIRDFQITASGQYGQWAPKLARLHYSGSINA WSTKEPFSWIKVDLLAPMIIHGIKTQGARQKFSSLYISQFIIMYSL DGKKWQTYRGNSTGTLMVFFGNVDSSGIKHNIFNPPIIARYIRLH PTHYSIRSTLRMEWMGCDLNSCSMPLGMESKAISDAQITASSYF TNMFATWSPSKARLHLQGRSNAWRPQVNNPKEWLQVDFQKTM KVTGVTTQGVKSLLTSMYVKEFLISSSQDGHQWTLFFQNGKVK VFQGNQDSFTPVVNSLDPPLLTRYLRIHPQSWVHQIALRMEVLG CEAQDL<u>YLTPRGVRL</u>*GGGSGGGSGGGSGGGS*QVQLVQSGGGL VQAGDSLRLSCAASGRTFIRYAMAWFRQAPGKEREFVAAIP QSGGRSYYADSVKGRFTISRDNAKNTVYLQMNSLKPEDTAV YSCAATSTYYGRSAYSSHSGGYDYWGQGTQVTVSS*GGGSGG GSGGGSGGGS*QVQLVQSGGGLVQAGDSLRLSCAASGRTFIRY AMAWFRQAPGKEREFVAAIPQSGGRSYYADSVKGRFTISRD NAKNTVYLQMNSLKPEDTAVYSCAATSTYYGRSAYSSHSGG YDYWGQGTQVTVSS*** |

Italic: GGGS-linker
Bold: sequence KB-VWF-013
Underline: thrombin-cleavage site

In a particular embodiment, two sdAb directed against VWF are inserted within the B-domain of FVIII, while two sdAb are inserted at the C-terminus (FVIII_KB0013bv (6GGGS)_

TABLE L-continued

Sequences of FVIII_KB0013bv(6GGGS)_Cter-0013bv_Y1680F

| FVIII_KB0013bv (6GGGS)_Cter-0013bv_Y1680F | Sequence |
|---|---|
| | TISVEMKKEDFDIFDEDENQSPRSFQKKTRHYFIAAVERLWDYG<br>MSSSPHVLRNRAQSGSVPQFKKVVFQEFTDGSFTQPLYRGELNE<br>HLGLLGPYIRAEVEDNIMVTFRNQASRPYSFYSSLISYEEDQRQG<br>AEPRKNFVKPNETKTYFWKVQHHMAPTKDEFDCKAWAYFSDV<br>DLEKDVHSGLIGPLLVCHTNTLNPAHGRQVTVQEFALFFTIFDET<br>KSWYFTENMERNCRAPCNIQMEDPTFKENYRFHAINGYIMDTLP<br>GLVMAQDQRIRWYLLSMGSNENIHSIHFSGHVFTVRKKEEYKM<br>ALYNLYPGVFETVEMLPSKAGIWRVECLIGEHLHAGMSTLFLVY<br>SNKCQTPLGMASGHIRDFQITASGQYGQWAPKLARLHYSGSINA<br>WSTKEPFSWIKVDLLAPMIIHGIKTQGARQKFSSLYISQFIIMYSL<br>DGKKWQTYRGNSTGTLMVFFGNVDSSGIKHNIFNPPIIARYIRLH<br>PTHYSIRSTLRMEWMGCDLNSCSMPLGMESKAISDAQITASSYF<br>TNMFATWSPSKARLHLQGRSNAWRPQVNNPKEWLQVDFQKTM<br>KVTGVTTQGVKSLLTSMYVKEFLISSSQDGHQWTLFFQNGKVK<br>VFQGNQDSFTPVVNSLDPPLLTRYLRIHPQSWVHQIALRMEVLG<br>CEAQDL<u>YLTPRGVRL</u>*GGGSGGGSGGGSGGGS*QVQLVQSGGGL<br>VQAGDSLRLSCAASGRTFIRYAMAWFRQAPGKEREFVAAIP<br>QSGGRSYYADSVKGRFTISRDNAKNTVYLQMNSLKPEDTAV<br>YSCAATSTYYGRSAYSSHSGGYDYWGQGTQVTVSS*GGGSGG<br>GSGGGSGGGS*QVQLVQSGGGLVQAGDSLRLSCAASGRTFIRY<br>AMAWFRQAPGKEREFVAAIPQSGGRSYYADSVKGRFTISRD<br>NAKNTVYLQMNSLKPEDTAVYSCAATSTYYGRSAYSSHSGG<br>YDYWGQGTQVTVSS\* |

Italic: GGGS-linker
Bold: sequence KB-VWF-013
Underline: thrombin-cleavage site
Bold underline: mutation p.Y1680F In a particular embodiment, the clotting factor is FVII. The terms "Factor VII" and "FVII" are used interchangeably herein. Factor VII is a trace plasma glycoprotein that circulates in blood as a single-chain zymogen. The zymogen is catalytically inactive. Single-chain Factor VII may be converted to two-chain Factor VIIa by Factor Xa, Factor XIIa, Factor IXa or thrombin in vitro. Factor Xa is believed to be the major physiological activator of Factor VII. Like several other plasma proteins involved in haemostasis, Factor VII is dependent on vitamin K for its activity, which is required for the γ-carboxylation of multiple glutamic acid residues that are clustered in the amino terminus of the protein. These γ-carboxylated glutamic acids are required for the metal-associated interaction of Factor VII with phospholipids.

The conversion of zymogen Factor VII into the activated two-chain molecule occurs by cleavage of an internal peptide bond located approximately in the middle of the molecule. In human Factor VII, the activation cleavage site is at Arg152-Ile153. In the presence of tissue Factor, phospholipids and calcium ions, the two-chain Factor VIIa rapidly activates Factor X or Factor IX by limited proteolysis. Commercially available therapeutic FVII products include plasma derived FVII (pdFVII), such as Factor VII® (=Immuseven commercialized by Baxter) and recombinant FVII (rFVII) products, such as NovoSeven® which is commercialized by NovoNordisk, and other recombinant FVII products which are on clinical trials: prLA-rFVIIa of Novonordisk (phase I/II trial), CSL689 rVIIa-FP of CSL Behring (phase II/III trial), BAX 817 of Baxter (phase III trial), LR769 of rEVO Biologics and LFB Biotechnologies (phase III trial), BAY 86-6150 eptacog alfa of Bayer (phase II/III trail), Factor VIIa-CTP of OPKO Health (phase II trial) or PF-05280602 of Pfizer (phase I trial).

In certain embodiments, the polypeptide comprises a FVII polypeptide and at least one sdAb directed against VWF according to the invention, wherein said FVII polypeptide comprises Gla domain, hydrophobic region, EGF1 and EGF2 domains, catalytic domains (His-Asp-Ser) and wherein said at least one single-domain antibody directed against VWF is linked to said FVII polypeptide at the C-terminus of said FVII polypeptide.

The typical half-life of a human FVII in humans is several hours (4.2 hours, Osterm et al 2007, Thromb Haemostas vol 98, pp 790-797). In some embodiments, the chimeric FVII polypeptide has extended half-life compared to wild type FVII polypeptide. In certain embodiments, the half-life of the chimeric FVII polypeptide is extended at least about 1.5 times, at least about 2 times, at least about 2.5 times, at least about 3 times, at least about 4 times, at least about 5 times, at least about 6 times, at least about 7 times, at least about 8 times, at least about 9 times, at least about 10 times, at least about 11 times, or at least about 12 times longer than wild type FVII.

In a particular embodiment, the sdAb directed against VWF are inserted at the C-ter domain of factor VII (FVII-KB13-bv) (SEQ ID NO: 14).

TABLE M

Sequences of FVII-KB13-bv

| FVII-KB13-bv | Sequence |
|---|---|
| Polypeptide | SEQ ID NO: 14<br>MVSQALRLLCLLLGLQGCLAAGGVAKASGGETRDMPWK<br>PGPHRVFVTQEEAHGVLHRRRRANAFLEELRPGSLERE<br>CKEEQCSFEEAREIFKDAERTKLFWISYSDGDQCASSP<br>CQNGGSCKDQLQSYICFCLPAFEGRNCETHKDDQLICV<br>NENGGCEQYCSDHTGTKRSCRCHEGYSLLADGVSCTPT<br>VEYPCGKIPILEKRNASKPQGRIVGGKVCPKGECPQVL<br>LLVNGAQLCGGTLINTIWVVSAAHCFDKIKNWRNLIAV<br>LGEHDLSEHDGDEQSRRVAQVIIPSTYVPGTTNHDIAL<br>LRLHQPVVLTDHVVPLCLPERTFSERTLAFVRFSLVSG |

TABLE M-continued

Sequences of FVII-KB13-bv

| FVII-KB13-bv | Sequence |
|---|---|
| | WGQLLDRGATALELMVLNVPRLMTQDCLQQSRKVGDSP NITEYMFCAGYSDGSKDSCKGDSGGPHATHYRGTWYLT GIVSWGQGCATVGHFGVYTRVSQYIEWLQKLMRSEPRP GVLLRAPFPLTPRGVRLGGGSGGGSGGGSGGGSQVQLV QSGGGLVQAGDSLRLSCAASGRTFIRYAMAWFRQAPGK EREFVAAIPQSGGRSYYADSVKGRFTISRDNAKNTVYL QMNSLKPEDTAVYSCAATSTYYGRSAYSSHSGGYDYWG QGTQVTVSSGGGSGGGSGGGSGGGSQVQLVQSGGGLVQ AGDSLRLSCAASGRTFIRYAMAWFRQAPGKEREFVAAI PQSGGRSYYADSVKGRFTISRDNAKNTVYLQMNSLKPE DTAVYSCAATSTYYGRSAYSSHSGGYDYWGQGTQVTVS S |

In a particular embodiment, the chimeric polypeptide according to the invention, wherein two sdAb directed against VWF: i) are replacing the C-terminal part of the B domain of factor VIII (FVIII-KB13-bv) (SEQ ID NO: 13; SEQ ID NO: 16; SEQ ID NO: 17); ii) are fused to the C-terminus of FVIII (SEQ ID NO: 18; SEQ ID NO: 19); iii) are simultaneously replacing the C-terminal part of the B domain of factor VIII and fused to C-terminus of factor VIII (SEQ ID NO: 20; SEQ ID NO: 21; SEQ ID NO 22; SEQ ID NO 23); or iv) are inserted at the C-terminus of factor VII (SEQ ID NO: 14).

In a particular embodiment, the chimeric polypeptide according to the invention, wherein the polypeptide comprises at least one single-domain antibody directed against a first antigen and at least one further binding site directed against a second antigen.

According to the invention, the single domain antibodies and polypeptides of the invention may be produced by conventional automated peptide synthesis methods or by recombinant expression. General principles for designing and making proteins are well known to those of skill in the art.

The single domain antibodies and polypeptides of the invention may be synthesized in solution or on a solid support in accordance with conventional techniques. Various automatic synthesizers are commercially available and can be used in accordance with known protocols as described in Stewart and Young; Tam et al., 1983; Merrifield, 1986 and Barany and Merrifield, Gross and Meienhofer, 1979. The single domain antibodies and polypeptides of the invention may also be synthesized by solid-phase technology employing an exemplary peptide synthesizer such as a Model 433A from Applied Biosystems Inc. The purity of any given protein; generated through automated peptide synthesis or through recombinant methods may be determined using reverse phase HPLC analysis. Chemical authenticity of each peptide may be established by any method well known to those of skill in the art.

As an alternative to automated peptide synthesis, recombinant DNA technology may be employed wherein a nucleotide sequence which encodes a polypeptide of choice is inserted into an expression vector, transformed or transfected into an appropriate host cell and cultivated under conditions suitable for expression as described herein below. Recombinant methods are especially preferred for producing longer polypeptides.

A variety of expression vector/host systems may be utilized to contain and express the peptide or protein coding sequence. These include but are not limited to microorganisms such as bacteria transformed with recombinant bacteriophage, plasmid or cosmid DNA expression vectors; yeast transformed with yeast expression vectors (Giga-Hama et al., 1999); insect cell systems infected with virus expression vectors (e.g., baculovirus, see Ghosh et al., 2002); plant cell systems transfected with virus expression vectors (e.g., cauliflower mosaic virus, CaMV; tobacco mosaic virus, TMV) or transformed with bacterial expression vectors (e.g., Ti or pBR322 plasmid; see e.g., Babe et al., 2000); or animal cell systems. Those of skill in the art are aware of various techniques for optimizing mammalian expression of proteins, see e.g., Kaufman, 2000; Colosimo et al., 2000. Mammalian cells that are useful in recombinant protein productions include but are not limited to VERO cells, HeLa cells, Chinese hamster ovary (CHO) cell lines, COS cells (such as COS-7), W138, BHK, HepG2, 3T3, RIN, MDCK, A549, PC12, K562 and 293 cells. Exemplary protocols for the recombinant expression of the peptide substrates or fusion polypeptides in bacteria, yeast and other invertebrates are known to those of skill in the art and a briefly described herein below. Mammalian host systems for the expression of recombinant proteins also are well known to those of skill in the art. Host cell strains may be chosen for a particular ability to process the expressed protein or produce certain post-translation modifications that will be useful in providing protein activity. Such modifications of the polypeptide include, but are not limited to, acetylation, carboxylation, glycosylation, phosphorylation, lipidation and acylation. Post-translational processing which cleaves a "prepro" form of the protein may also be important for correct insertion, folding and/or function. Different host cells such as CHO, HeLa, MDCK, 293, WI38, and the like have specific cellular machinery and characteristic mechanisms for such post-translational activities and may be chosen to ensure the correct modification and processing of the introduced, foreign protein.

In the recombinant production of the single domain antibodies and polypeptides of the invention, it would be necessary to employ vectors comprising polynucleotide molecules for encoding the single domain antibodies and polypeptides of the invention. Methods of preparing such vectors as well as producing host cells transformed with such vectors are well known to those skilled in the art. The polynucleotide molecules used in such an endeavor may be joined to a vector, which generally includes a selectable marker and an origin of replication, for propagation in a host. These elements of the expression constructs are well known to those of skill in the art. Generally, the expression vectors include DNA encoding the given protein being operably linked to suitable transcriptional or translational regulatory sequences, such as those derived from a mammalian, microbial, viral, or insect genes. Examples of regulatory sequences include transcriptional promoters, operators, or enhancers, mRNA ribosomal binding sites, and appropriate sequences which control transcription and translation.

The terms "expression vector," "expression construct" or "expression cassette" are used interchangeably throughout this specification and are meant to include any type of genetic construct containing a nucleic acid coding for a gene product in which part or all of the nucleic acid encoding sequence is capable of being transcribed.

The choice of a suitable expression vector for expression of the peptides or polypeptides of the invention will of course depend upon the specific host cell to be used, and is within the skill of the ordinary artisan.

Expression requires that appropriate signals be provided in the vectors, such as enhancers/promoters from both viral and mammalian sources that may be used to drive expression of the nucleic acids of interest in host cells. Usually, the nucleic acid being expressed is under transcriptional control of a promoter. A "promoter" refers to a DNA sequence recognized by the synthetic machinery of the cell, or introduced synthetic machinery, required to initiate the specific transcription of a gene. Nucleotide sequences are operably linked when the regulatory sequence functionally relates to the DNA encoding the protein of interest (e.g., a single domain antibody). Thus, a promoter nucleotide sequence is operably linked to a given DNA sequence if the promoter nucleotide sequence directs the transcription of the sequence.

Chimeric Polypeptide/VWF Complexes According to the Invention

In another aspect, the invention relates to a chimeric polypeptide/VWF complex wherein the chimeric polypeptide is a chimeric polypeptide of the invention above-described and a VWF polypeptide with extended half-life.

As used herein, the term "VWF polypeptide with extended half-life" refers to variants of VWF or fragments thereof (including especially D'D3 domain) with insertions, deletions and substitutions, either conservative or non-conservative, where such changes do not alter the biological activities of VWF, or derivatives of WVF such as Fc-fusion, leading to an extended half-life compared to the native VWF. The typical half-life of a human VWF in humans is 16 hours (Goudemand et al 2005).

In one embodiment, the VWF polypeptide with extended half-life is a PEGylated rVWF (PEGrVWF).

Polyethylene glycol (PEG) has been widely used as a drug carrier, given its high degree of biocompatibility and ease of modification. Attachment to various drugs, proteins, and liposomes has been shown to improve residence time and decrease toxicity. PEG can be coupled to active agents through the hydroxyl groups at the ends of the chain and via other chemical methods; however, PEG itself is limited to at most two active agents per molecule. In a different approach, copolymers of PEG and amino acids were explored as novel biomaterials which would retain the biocompatibility properties of PEG, but which would have the added advantage of numerous attachment points per molecule (providing greater drug loading), and which could be synthetically designed to suit a variety of applications.

In a particular embodiment, the VWF polypeptide with extended half-life is a PEGylated VWF D'D3.

In a particular embodiment, the VWF polypeptide with extended half-life is a VWF D'D3 conjugated to albumin (D'D3-Alb).

In a particular embodiment, the VWF polypeptide with extended half-life is VWF D'D3-Fc (VWF D'D3-Fc has a prolonged half-life relative to VWF D'D3 because of interactions with the Fc receptor FcRn recycling pathway)[3].

Other possibilities of modifications to prolong the half-life of VWF or VWF D'D3 are HEPylation, polysialylation or the attachment of XTEN-polypeptides.

Therapeutic Methods and Uses

In another aspect, the invention relates to an isolated single-domain antibody (sdAb) directed against von Willebrand Factor (VWF) D'D3 domain for use as drug.

In another aspect, the invention relates to a chimeric polypeptide comprising a polypeptide and at least one single-domain antibody of the invention for use as drug.

In still another aspect, the invention relates to a chimeric polypeptide/VWF complex of the invention for use as drug.

According to the invention, a single domain antibody of the invention or a chimeric polypeptide of the invention, or a chimeric polypeptide/VWF complex of the invention is administered to the patient with a therapeutically effective amount.

In a particular embodiment, the isolated sdAb directed against VWF D'D3 domain according to the invention, a chimeric polypeptide comprising a polypeptide and at least one sdAb directed against VWF according to the invention, or the chimeric polypeptide/VWF complex according to the invention for use in a method for preventing or treating bleeding disorders.

In another embodiment, the invention is suitable for a method of preventing or treating bleeding disorders in a subject in need thereof, comprising administering to said subject a therapeutically effective amount of a chimeric polypeptide according to the invention or a chimeric polypeptide/VWF complex as described above.

For instance the modified clotting factors according to the invention may be used in a method for preventing and/or treating bleeding disorders. The bleeding disorders that may be treated by administration of the modified clotting factors of the invention include, but are not limited to, hemophilia, as well as deficiencies or structural abnormalities in fibrinogen, prothrombin, Factor V, Factor VII or Factor X.

In a particular embodiment, the bleeding disorders that may be treated by administration of the modified clotting factors of the invention is hemophilia A or hemophilia B.

By a "therapeutically effective amount" is meant a sufficient amount of the polypeptide (or the nucleic acid encoding for the polypeptide) to prevent for use in a method for the treatment of acute exacerbation of chronic obstructive pulmonary disease at a reasonable benefit/risk ratio applicable to any medical treatment. It will be understood that the total daily usage of the compounds and compositions of the present invention will be decided by the attending physician within the scope of sound medical judgment. The specific therapeutically effective dose level for any particular patient will depend upon a variety of factors including the age, body weight, general health, sex and diet of the patient; the time of administration, route of administration, and rate of excretion of the specific compound employed; the duration of the treatment; drugs used in combination or coincidental with the specific polypeptide employed; and like factors well known in the medical arts. For example, it is well known within the skill of the art to start doses of the compound at levels lower than those required to achieve the desired therapeutic effect and to gradually increase the dosage until the desired effect is achieved. However, the daily dosage of the products may be varied over a wide range from 0.01 to 1,000 mg per adult per day. Preferably, the compositions contain 0.01, 0.05, 0.1, 0.5, 1.0, 2.5, 5.0, 10.0, 15.0, 25.0, 50.0, 100, 250 and 500 mg of the active ingredient for the symptomatic adjustment of the dosage to the patient to be treated. A medicament typically contains from about 0.01 mg to about 500 mg of the active ingredient, preferably from 1 mg to about 100 mg of the active ingredient. An effective amount of the drug is ordinarily supplied at a dosage level from 0.0002 mg/kg to about 20 mg/kg of body weight per day, especially from about 0.001 mg/kg to 7 mg/kg of body weight per day.

Another aspect relates to a pharmaceutical composition comprising a single-domain antibody directed against VWF D'D3 domain, a chimeric polypeptide, a chimeric polypeptide/VWF complex as described herein, and a pharmaceutically acceptable carrier.

The single-domain antibodies and polypeptides of the invention (or the nucleic acid encoding thereof) may be combined with pharmaceutically acceptable excipients, and optionally sustained-release matrices, such as biodegradable polymers, to form pharmaceutical compositions. As used herein, the terms "pharmaceutically" or "pharmaceutically acceptable" refer to molecular entities and compositions that do not produce an adverse, allergic or other untoward reaction when administered to a mammal, especially a human, as appropriate. A pharmaceutically acceptable carrier or excipient refers to a non-toxic solid, semi-solid or liquid filler, diluent, encapsulating material or formulation auxiliary of any type.

In the pharmaceutical compositions of the invention for oral, sublingual, subcutaneous, intramuscular, intravenous, transdermal, local or rectal administration, the active principle, alone or in combination with another active principle, can be administered in a unit administration form, as a mixture with conventional pharmaceutical supports, to animals and human beings. Suitable unit administration forms comprise oral-route forms such as tablets, gel capsules, powders, granules and oral suspensions or solutions, sublingual and buccal administration forms, aerosols, implants, subcutaneous, transdermal, topical, intraperitoneal, intramuscular, intravenous, subdermal, transdermal, intrathecal and intranasal administration forms and rectal administration forms. Preferably, the pharmaceutical compositions contain vehicles which are pharmaceutically acceptable for a formulation capable of being injected. These may be in particular isotonic, sterile, saline solutions (monosodium or disodium phosphate, sodium, potassium, calcium or magnesium chloride and the like or mixtures of such salts), or dry, especially freeze-dried compositions which upon addition, depending on the case, of sterilized water or physiological saline, permit the constitution of injectable solutions.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi. Solutions comprising compounds of the invention as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The polypeptide (or nucleic acid encoding thereof) can be formulated into a composition in a neutral or salt form. Pharmaceutically acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. The carrier can also be a solvent or dispersion medium containing, for example, water, ethanol, polyol (for example, glycerol, propylene glycol, and liquid polyethylene glycol, and the like), suitable mixtures thereof, and vegetables oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminium monostearate and gelatin.

Sterile injectable solutions are prepared by incorporating the active polypeptides in the required amount in the appropriate solvent with several of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion. Some variation in dosage will necessarily occur depending on the condition of the subject being treated. The person responsible for administration will, in any event, determine the appropriate dose for the individual subject.

The polypeptide (or nucleic acid encoding thereof) may be formulated within a therapeutic mixture to comprise about 0.0001 to 1.0 milligrams, or about 0.001 to 0.1 milligrams, or about 0.1 to 1.0 or even about 10 milligrams per dose or so. Multiple doses can also be administered. The invention will be further illustrated by the following figures and examples.

Methods of Extending or Increasing Half-Life of a Therapeutic Polypeptide

Also disclosed is a method of extending or increasing half-life of a therapeutic polypeptide comprising a step of adding to the polypeptide sequence of said therapeutic polypeptide at least one single-domain antibody directed against VWF D'D3 domain.

In one embodiment, said at least one single-domain antibody directed against VWF is fused or inserted in the polypeptide sequence of said therapeutic polypeptide as above-described. In a particular embodiment, said at least one single-domain antibody directed against VWF is inserted within the B domain of factor VIII as above-described.

Methods for Reducing the Formation of Allo-Antibodies

In some embodiments, the sdAbs of the invention are suitable to reduce the formation of allo-antibodies. In a particular embodiment, at least one single-domain antibody directed against VWF is inserted within the B domain of factor VIII as above-described to reduce the formation of allo-antibodies.

The term "allo-antibodies" has the general meaning in the art and refers to an antibody that occurs naturally against foreign tissues from a person of the same species. Typically, in the context of the invention, incorporating sdAbs against VWF in the FVIII protein avoid the dissociation of FVIII from VWF (FVIII-KB013bv), thus, the subject does not develop allo-antibodies against FVIII-KB013bv which is less immunogenic compared to FVIII that displays normal association-dissociation kinetics.

The invention will be further illustrated by the following figures and examples. However, these examples and figures should not be interpreted in any way as limiting the scope of the present invention.

FIGURES

FIG. 1: Real-time analysis of association and dissociation of VWF interactions with FVIII and sdAbs. Association and dissociation curves for the binding of VWF to immobilized sdAbs and the binding of FVIII to immobilized VWF are plotted in FIG. 1. For the analysis, we focused on the dissociation phase. Apparent dissociation constants were $2.0\pm1.1\times10^{-5}$ s$^{-1}$ (KB-VWF-008), $0.6\pm0.5\times10^{-5}$ s$^{-1}$ (KB-VWF-011), $1.3-3.5\times10^{-5}$ s$^{-1}$ (KB-VWF013) and $2.2-3.0\times10^{-3}$ s$^{-1}$ (FVIII).

Figure 2:
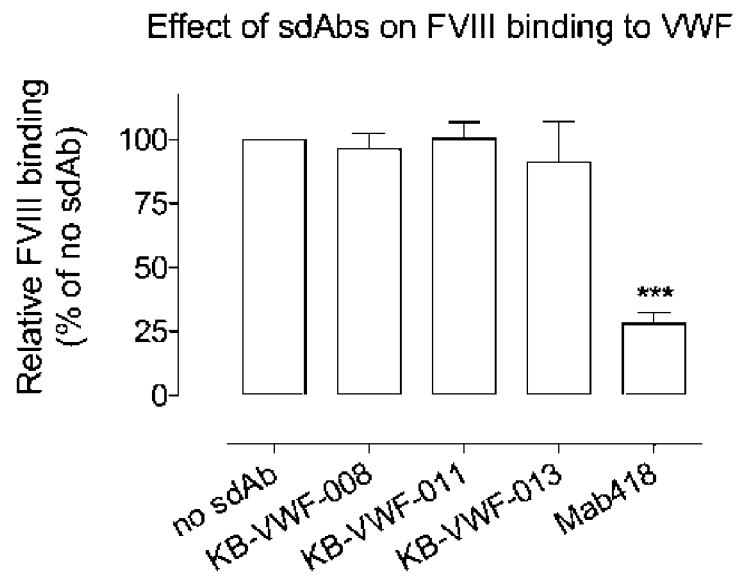

FIG. 2: Effect of sdAbs on VWF binding to Factor VIII. Binding of FVIII to immobilized VWF was determined in the absence or presence of sdAbs or Mab418. Plotted is the percentage FVIII binding relative to FVIII binding in the absence of antibodies. FVIII binding is unaffected by the presence of KB-VWF-008, -011 or -013.

Figure 3:
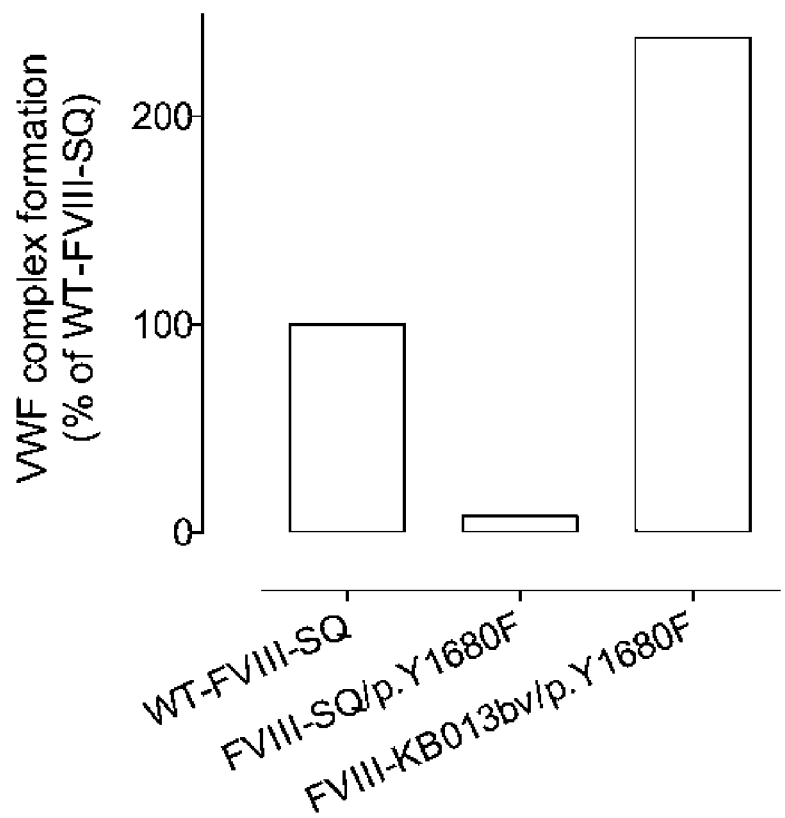

FIG. 3: Factor VIII-sdAb fusion protein binds to VWF. The ability to form a complex with VWF was tested via transient expression of WT-FVIII-SQ, FVIII-SQ/p.Y1680F or FVIII-KB013bv/p.Y1680F in hemophilic mice. Four days after gene transfer, VWF/FVIII complexes were determined, which are expressed as the percentage of complex relative to WT-FVIII-SQ. As expected, the presence of the p.Y1680F mutation abrogated binding of FVIII to VWF (FVIII-SQ/p.Y1680F). In contrast, the introduction of KB-VWF-013 restored and even improved binding to VWF despite the presence of the p.Y1680F mutation.

Figure 4:
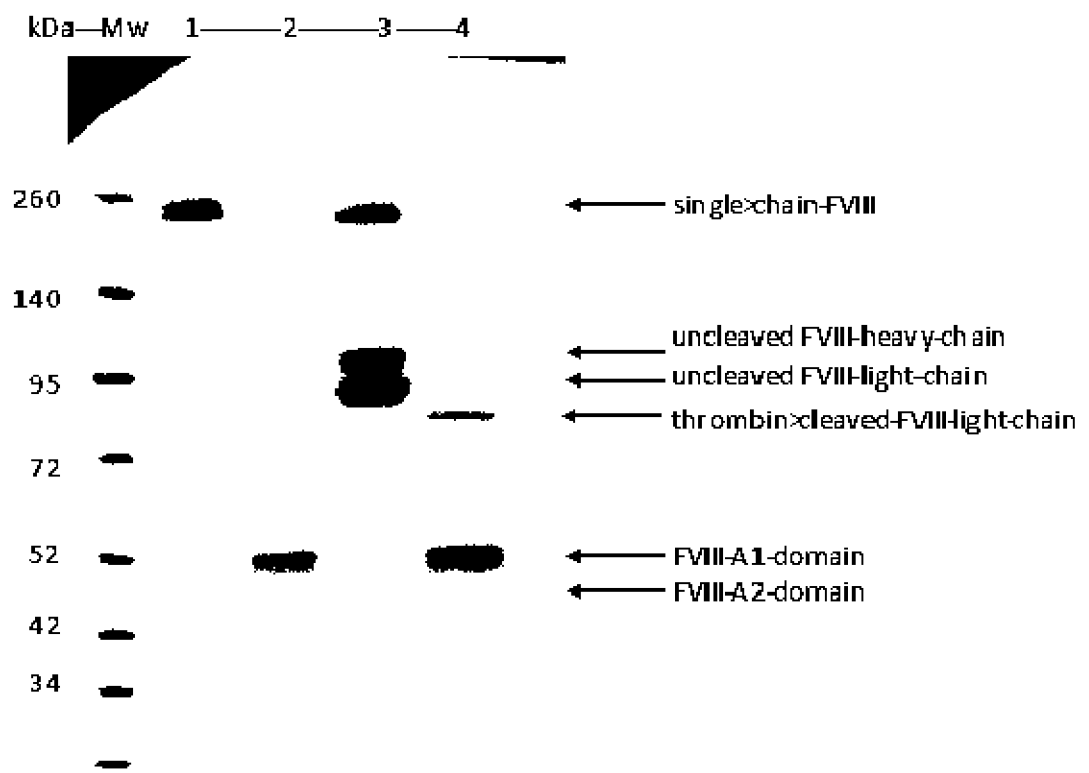

FIG. 4: Expression and functional analysis of FVIII-KB013bv. Purified FVIII-KB013 and WT-FVIII-SQ were incubated in the absence or presence of thrombin. Western blot analysis was performed to determine the presence of FVIII fragments. FVIII-KB013bv migrates predominantly as a single-chain protein when incubated in the absence of thrombin (lane 1), whereas WT-FVIII-SQ predominantly migrates as a heterodimeric protein (lane 3). After thrombin incubation, both FVIII-KB013bv and WT-FVIII-SQ are present as a heterodimeric protein, consisting of the thrombin-cleaved light chain and the heavy-chain derived A1 and A2 domains (lanes 2 & 4).

Figure 5:
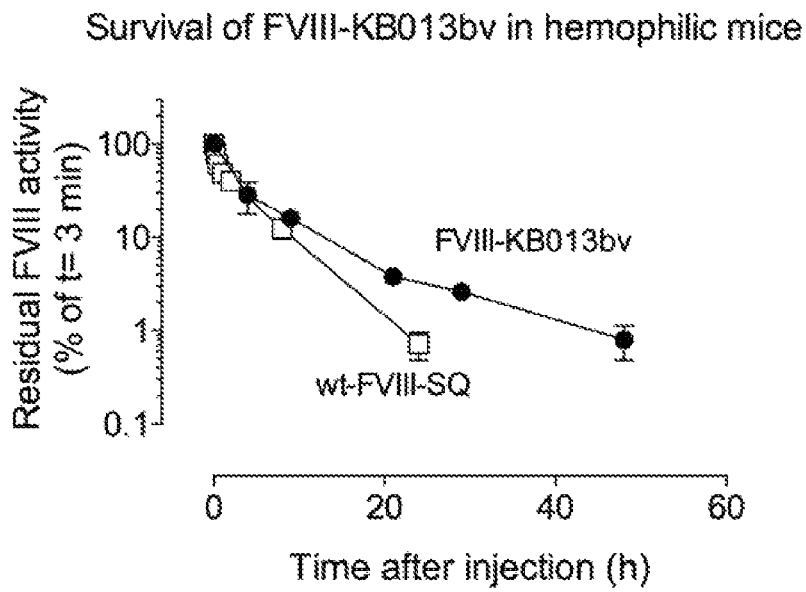

FIG. 5: in vivo survival of FVIII-KB-013bv. FVIII-KB013bv or WT-FVIII-SQ were given intravenously to FVIII-deficient mice. At indicate time-points, blood was collected and FVIII activity was determined. Residual activity relative to activity at 3 min after injection is plotted against time after injection. FVIII-KB013bv is removed from the circulation slower than is WT-FVIII-SQ.

Figure 6:
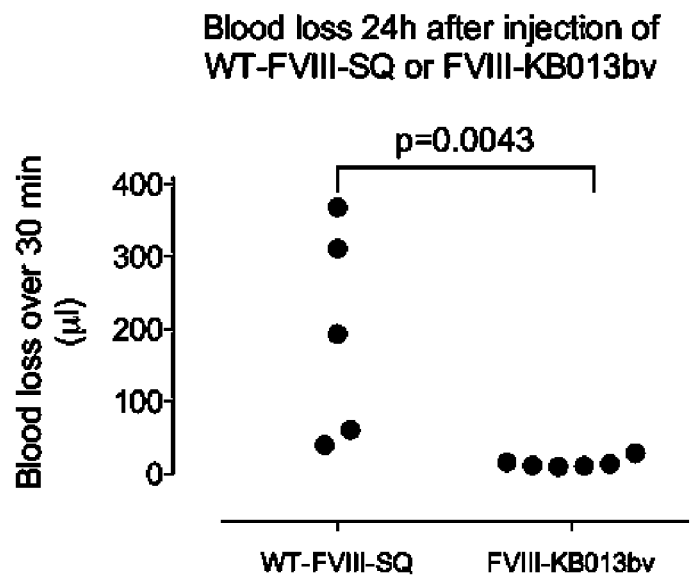

FIG. 6: Correction of hemostasis in hemophilic mice 24 h after injection of FVIII-KB013bv. FVIII-KB013bv or B-domainless FVIII (Xyntha) were given intravenously to FVIII-deficient mice and 24 h after injection the terminal tip of the tail was amputated in anesthetized mice. Blood loss was monitored for 30 min. The volume of shed blood was determined and is presented for each mouse. Mice treated with FVIII-KB013bv lost significantly less blood compared to mice treated with wild-type B-domainless FVIII.

Figure 7:
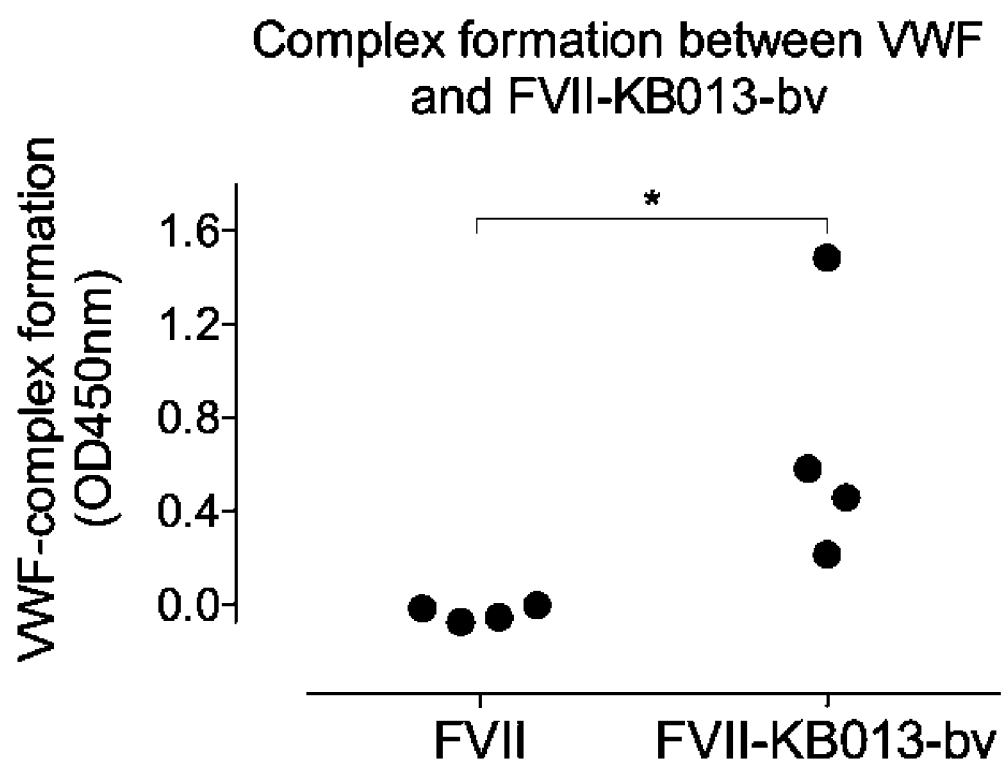

FIG. 7: Fusion of KB-VWF-013 to coagulation factor VII induces complex formation with VWF. The ability to form a complex with VWF was tested via transient expression of wild-type FVII and FVII-KB013-bv in wild-type C57B16 mice. Four days after gene transfer, VWF/FVIII complexes were determined, which are expressed as OD450 nm. As expected, no complex formation with VWF could be detected for wild-type FVII. In contrast, VWF-FVII complexes were detected in all mice expressing FVII-KB013-bv. Thus, the fusion of FVII to KB-VWF-013 induces the capacity of FVII to bind to VWF.

EXAMPLES

Example A: Protein Domain Structure of VWF

Bio-informatic analysis of the cDNA and protein sequences of VWF has revealed that the protein architecture distinguishes different types of domain structures. Originally, this domain structure consisted of a signal peptide (SP), A-domains, B-domains, C-domains, D-domains and a CK-domain arranged in the order: SP-D1-D2-D'-D3-A1-A2-A3-D4-B1-B2-B3-C1-C2-CK (Verweij C L et al. (1986) EMBO Journal, vol. 5, pp. 1839-1847). More recently an updated domain organization has been proposed, in which the domains are arranged in the following order: SP-D1-D2-D'-D3-A1-A2-A3-D4-C1-C2-C3-C4-C5-C6-CK (Zhou Y F et al. (2012) Blood, vol 120, pp. 449-458). Since the boundaries of the different domains may be varying from one publication to another, we use in this application the boundaries as defined in FIG. 1 of Lenting P J et al. (2015) Blood, vol 125, pp. 2019-2028).

Example B: Binding of sdAb to VWF or Fragments Thereof sdAbs KB-VWF-008, -011 and -013 were immobilized (5 µg/ml) in 10 mM NaHCO3, 50 mM Na2CO3 (pH 9.5) in a volume of 50 µl in half-well microtiter plates (Greiner Bio-One, Les Ulis, France) for 16 h at 4° C. As a positive control, polyclonal rabbit anti-VWF antibodies (Dako, Glostrup, Danmark) were immobilized in a similar fashion. As a negative control, no antibodies were immobilized. After washing the wells three times with 75 µl/well using Tris-buffered saline (pH 7.6) supplemented with 0.1% Tween-20 (TBS-T), wells were blocked with 75 μl/well of TBS-T supplemented with 3% bovine serum albumin (BSA) for 30 min at 37° C. Wells were washed as described above, and subsequently the following VWF preparations (diluted in Tris-buffered saline (pH 7.6) supplemented with 3% BSA, all at 2 μg/ml, 50 μl per well, 2 hours at 37° C.) were added to each of the immobilized sdAbs and both types of control wells:

purified recombinant human VWF (rhVWF),
purified recombinant murine VWF (rmVWF),
VWF fragment SpII (a proteolytic fragment of plasma-derived (pd)-VWF following incubation with S. aureus V8-protease, which encompasses residues 2129-2813 of VWF; Denis C et al. (1993) Arteriosclerosis Thrombosis, vol 13, pp. 398-406),
VWF fragment SpIII (a proteolytic fragment of pd-VWF following incubation with S. aureus V8-protease, which encompasses residues 764-2128 of VWF; Kalafatis M et al. (1987) Blood, vol 70, pp. 1577-1583),
D'D3-HPC4 fragment (human VWF residues 764-1247 fused to the amino acid sequence EDQVDPRLIDGK (SEQ ID NO: 15), representing a recognition site for antibody HPC4),
A1-A2-A3-HPC4 fragment (human VWF residues 1260-1874 fused to the amino acid sequence EDQVDPRLIDGK),
hD1-D2-HPC4 fragment (human VWF residues 23-762 fused to the amino acid sequence EDQVDPRLIDGK),
mD1-D2-HPC4 fragment (murine VWF residues 23-762 fused to the amino acid sequence EDQVDPRLIDGK)

Wells were then washed three times with 75 μl/well using TBS-T. Bound VWF preparations were probed with peroxidase-labeled polyclonal rabbit anti-VWF antibodies (Dako, Glostrup, Danmark; diluted 1/6000) for rhVWF, rmVWF, SpII and SPIII or with peroxidase-labeled monoclonal antibody HPC4 (diluted 1/1000) for D'D3-HPC4, A1A2A3-HPC4, hD1D2-HPC4 and mD1-D2-HPC4 for 2 hours at 37° C. with 50 μl per well. Wells were then washed three times with 75 μl/well using TBS-T. Residual peroxidase activity was detected by measuring peroxidase-mediated hydrolysis of 3,3',5,5'-tetramethylbenzidine.

Negative binding (−) was defined as optical density (OD) being ≤0.5, moderate positive binding (+) was defined as OD being >0.5 and <1.0, strongly positive binding (++) was defined as OD being ≥1.0. Based on these definitions, none of the VWF preparations displayed moderate or strongly positive binding to the negative control (Table 1). All VWF preparations with the exception of mD1-D2-HPC4 had moderate or strongly positive binding to the positive control (polyclonal anti-VWF antibodies). None of the sdAbs bound to SpII, A1A2A3-HPC4, hD1-D2-HPC4 or mD1-D2-HPC4. In contrast, KB-VWF-008, -011 and -013 had moderate or strongly positive binding to rhVWF, spill and D'D3-HPC4, suggesting that the epitope of these three sdAbs is located within VWF residues 764-1247. Furthermore, sdAb KB-VWF-013 was the only one of the three tested sdAbs that reacted positively with rmVWF, showing that this sdAb cross-reacts with murine VWF.

TABLE 1 belonging to example B: Binding of sdAb to VWF and fragments thereof

| sdAb | rhVWF | rmVWF | SpII | SpIII | D'D3-HPC4 | A1A2A3-HPC4 | hD1D2-HPC4 | mD1D2-HPC4 |
|---|---|---|---|---|---|---|---|---|
| 008 | + | − | − | + | ++ | − | − | − |
| 011 | ++ | − | − | + | ++ | − | − | − |
| 013 | ++ | + | − | ++ | ++ | − | − | − |
| Control | ++ | + | ++ | ++ | ++ | ++ | + | − | rhVWF; recombinant humanVWF rmVWF; recombinant murine VWF; spII: a proteolytic fragment of plasma-derived (pd)-VWF following incubation with S. aureus V8-protease, which encompasses residues 2129-2813 of VWF; spIII: a proteolytic fragment of pd-VWF following incubation with S. aureus V-8 protese, which encompasses residues 764-2128 of VWF; D'D3-HPC4: human VWF residues 764-1247 fused amino acid sequence EDQVDPRLIDGK; A1-A2-A3-HPC4: human VWF residues 1260-1874 fused to the amino acid sequence EDQVDPRLIDGK; hD1-D2-HPC4: human VWF residues 23-762 fused to the amino acid sequence EDQVDPRLIDGK; mD1-D2-HPC4: murine VWF residues 23-762 fused to amine acid sequence EDQVDPRLIDGK; control; polyclonal rabbit-antihuman VWF antibodies (Dako).
−Negative binding defined as OD being ≤ 0.5;
+Moderate positive binding defined as OD being >0.5-<1.0;
++Strongly positive binding defined as being ≥1.0

Example C: Real-Time Analysis of Association and Dissociation of VWF Interactions with FVIII and sdAbs The interaction between VWF and sdAbs was analyzed via bio-layer interferometry using Octet-QK equipment (Fortébio, Meldo Park, Calif., USA). To this end, sdAbs KB-VWF-008, -011 and -013 were diluted in 0.1 M Mes (pH 5.0) to a concentration of 10 μg/ml for coupling to EDC/NHS-activated amine-reactive biosensors (Fortébio, Menlo Park, Calif., USA). Sensors were rehydrated in 0.2 ml 0.1 M MES, pH 5.0 for 300 sec. Sensors were then activated via incubation with 0.1 ml 0.2 M EDC/0.095 M NHS mixture for 300 sec and subsequently incubated with 0.1 ml sdAb-solution for 600 sec. Unoccupied amine-reactive sites were quenched by incubating with 1M ethanolamine for 180 sec, and sensors were allowed to reach stable baseline levels via incubation with phosphate-buffered saline supplemented with 0.1% Tween-20 (PBS-T) for 300 sec. sdAb-coated sensors were then transferred to wells containing various concentrations of purified plasma-derived VWF (2.5, 25 & 250 μg/ml in PBS-T for KB-VWF-008 and -011 versus 25 & 250 μg/ml for KB-VWF-013) and incubated for 600 sec in order to visualize association of VWF to immobilized sdAbs. Following this association phase, sensors were transferred to wells containing PBS-T and incubated for 900 sec, allowing dissociation of the VWF-sdAb complex.

In another set of experiments, we determined the association and dissociation of factor VIII to immobilized recombinant human VWF via biolayer-interferometry analysis, also using Octet-QK equipment. Amine-reactive biosensors were used to immobilize recombinant VWF (50 μg/ml in 0.1 M MES, pH 5.0). After hydration of the sensors via a 600-sec incubation with 0.1 M MES pH 5.0, sensors 2were activated with 0.1 ml 0.2 M EDC/0.095 M NHS mixture for 420 sec and subsequently incubated with 0.1 ml VWF-solution for 420 sec. Unoccupied amine-reactive sites were quenched by incubating with 1M ethanolamine for 420 sec, and sensors were allowed to reach stable baseline levels via incubation with Hepes-buffer (20 mM Hepes, 0.11 M NaCl, 0.005% Tween-20, 5 mM CaCl2, pH 7.3) for 600 sec. VWF-coated sensors were then transferred to wells containing various concentrations of purified recombinant full-length factor VIII (Kogenate; diluted to 3.5 nM or 1.4 nM in Hepes-buffer) and incubated for 600 sec in order to visualize association of FVIII to immobilized VWF. Following this association phase, sensors were transferred to wells containing Hepes-buffer and incubated for 600 sec, allowing dissociation of the VWF-FVIII complex.

Association and dissociation curves are plotted in FIG. 1. When analyzing the data for the interaction between sdAbs and VWF versus the interaction between VWF and FVIII, we focused on the dissociation phase for both types of interaction. The dissociation rate constant for the VWF-FVIII interaction was calculated using an equation for a single exponential decay, and the dissociation rate constants were calculated to be $2.2 \times 10^{-3}$ s−1 and $3.0 \times 10^{-3}$ s−1 for FVIII concentrations of 3.5 nM and 1.4 nM, respectively. These values are similar to those described in the literature ($0.3-6.0 \times 10^{-3}$ s−1; Sandberg et al (2012) Thromb Res vol 130, pp 808-817; Dimitrov et al (2012) Biochemistry vol 51, pp 4108-4116; Zollner et al (2014) Thromb Res vol 134, pp 125-131). The dissociation constants for the sdAbs were could not be calculated accurately using an equation for a single exponential decay, as the dissociation was too slow during the period that was monitored. We used therefore a linear regression approach to determine the slope of the dissociation curve, which represents an apparent dissociation rate constant that probably over-estimates the true dissociation rate constant (i.e. in reality dissociation is slower than represented by the apparent dissociation rate constant). For KB-VWF-008, the apparent dissociation rate constant was $2.0 \pm 1.1 \times 10^{-5}$ s−1 (mean±standard deviation; n=3 concentrations). For KB-VWF-011, the apparent dissociation rate constant was $0.6 \pm 0.5 \times 10^{-5}$ s−1 (mean±standard deviation; n=3 concentrations). For KB-VWF-013, the apparent dissociation rate constants was $1.3 \times 10^{-5}$ s−1 and $3.5 \times 10^{-5}$ s−1 (for 250 □g/ml and 25 □g/ml, respectively). Thus, for each of the three sdAbs, the apparent dissociation rates constants for the interaction with VWF are at least 15-300-fold slower compared to those dissociation rates constants reported in the literature for the FVIII-VWF interaction, and at least 100-fold slower compared to the dissociation rate constant calculated for the VWF-FVIII interaction analyzed in the same Octet-QK equipment.

Example D: Effect of sdAbs on VWF Binding to Factor VIII

Polyclonal rabbit anti-VWF antibodies (Dako, Glostrup, Danmark) were immobilized onto microtiter wells at 5 μg/ml in 50 mM Na2CO3 (pH 9.5) overnight at 4° C. in a volume of 50 μl. After washing thrice with Tris-buffered saline supplemented with 0.1% Tween-20 (TBS-T), wells were saturated with 3% BSA in TBS-T. Then rVWF (0.03-1.0 μg/ml; 50 μl/well) was added to the wells and incubated overnight at 4° C. After washing in TBS-T, wells were incubated twice with 75 μl of 0.35 M CaCl2 for 10 min at 37° C., followed by 6 washes with TBTS-T (75 μl/well). Then rFVIII (Kogenate-FS, Bayer Healthcare) diluted to a concentration of 1.5 U/ml was added in the presence or absence of 20 μg/ml of sdAb KB-VWF-008, -11 or -013 in a total volume of 50 μl. As a control, FVIII was added in the presence of the murine monoclonal anti-VWF antibody Mab418, which blocks binding of FVIII to VWF (Takahashi Y et al. (1987) Blood vol 70, pp 1679-1682). After 2 h at 37° C. and 3 washes with TBS-T (75 μl/well), bound FVIII was probed using peroxidase-labeled polyclonal sheep-anti-FVIII antibodies (Stago BNL, Leiden, the Netherlands) and detected by measuring peroxidase-mediated hydrolysis of 3,3',5,5'-tetramethylbenzidine. For each VWF concentration, FVIII binding in the presence of sdAb or Mab418 was calculated relative to FVIII binding in the absence of sdAb or Mab418, and expressed in percentage binding (FIG. 2). Whereas the presence of Mab418 reduced binding of FVIII to VWF by 72±5% (mean±standard deviation; n=6; $p<0.001$ compared to control), the presence of each of the sdAbs left FVIII binding similar to that in the absence of any antibody ($p>0.05$ when tested using one-way ANOVA with multiple comparisons). This shows that sdAbs KB-VWF-008, -011 and -013 do not interfere with the binding of FVIII to VWF.

Example E: Factor VIII-sdAb Fusion Protein Binds to VWF cDNA constructs encoding wild-type B-domainless FVIII (WT-FVIII-SQ), B-domainless FVIII containing a Tyr to Phe replacement at position 1680 (FVIII-SQ/p.Y1680F) and FVIII-KB013bv containing a Tyr to Phe replacement at position 1680 (FVIII-KB013bv/p.Y1680F) were cloned into the pLIVE-plasmid (Mirus Bio, Madison, Wis., USA). Tyrosine at position 1680 is sulfated in WT-FVIII-SQ, a requirement for the binding to von Willebrand factor (VWF) and mutation of p.Tyr1680 to Phe is associated with a loss of VWF binding (Leyte A et al. (1991) J Biol Chem vol 266, pp 740-746). Plasmids (100 □g/mouse) were injected into factor VIII-deficient mice via hydrodynamic gene transfer: plasmids are diluted in 0.9% saline with the volume corresponding to 10% of the animal's bodyweight (i.e. 2 ml for a 20-gram mouse). The solution is injected in the tail vein within 5 seconds. Four days after gene transfer, blood was collected via retro-orbital puncture from isoflurane-anesthetized mice and plasma was prepared by centrifugation (1500 g for 20 min at 22° C.). Plasma was then used to measure VWF-FVIII complexes that were formed in the plasma of the mice. Complexes were determined as follows: microtiter wells were coated with polyclonal rabbit anti-VWF antibodies (5 μg/ml) as described in example D. After washing thrice with Tris-buffered saline supplemented with 0.1% Tween-20 (TBS-T), wells were saturated with 3% BSA in TBS-T. Then murine plasma samples (diluted 10-fold in TBS-T) were added to the wells and incubated 2 hours at 37° C. After 3 washes with TBS-T (75 μl/well), bound FVIII was probed using peroxidase-labeled polyclonal sheep-anti-FVIII antibodies (Stago BNL, Leiden, the Netherlands) and detected by measuring peroxidase-mediated hydrolysis of 3,3',5,5'-tetramethylbenzidine. The amount of VWF-complex for mutants FVIII-SQ/p.Y1680F and FVIII-KB013bv/p.Y1680F was related to that of WT-FVIII-SQ, which was arbitrarily set as 100%. As anticipated, complex formation with VWF was strongly reduced for mutant FVIII-SQ/p.Y1680F (8% compared to 100% for WT-FVIII-SQ; see FIG. 3). In contrast, binding was increased 2.4 fold (238%) for variant FVIII-KB013bv/p.Y1680F, which contains the VWF-binding sdAbs. Since the p.Y1680F mutation abrogates natural VWF binding, these data show that while incorporated in the factor VIII protein, sdAb KB-VWF-013 is able to rescue binding to VWF. Thus, in the context of the fusion protein, sdAb KB-VWF-013 contributes to VWF binding.

Example F: Expression and Functional Analysis of FVIII-KB013bv

Baby Hamster Kidney (BHK)-cells were transfected with cDNA encoding FVIII-KB013bv cloned in pcDNA3.1/Hygro and stable cell lines were obtained via selection with hygromycin. One clone was selected for the production of FVIII-KB013bv. FVIII-KB013bv was purified from the culture medium via affinity chromatography using VIIISelect-matrix as instructed by the manufacturer (GE Healthcare, Vélizy-Villacoublay, France). Purified FVIII-KB013bv was tested for activity and antigen. Five top-fractions were selected and chromogenic two-stage activity (Biophen FVIII:C; Hyphen Biomed, Neuville-sur-Oise, France) and factor VIII antigen levels (Girma J P et al (1998) Haemophilia vol 4 pp 98-103) were determined. Average activity was found to be 188±42 U/ml (mean±SD; n=5 consecutive elution fractions) and antigen was calculated to be 176±28 U/ml. Average activity/antigen ratio was 1.1±0.3, showing that FVIII-KB013bv displays full activity in the chromogenic two-stage activity assay.

In a second analysis, FVIII-KB013bv and WT-FVIII-SQ were incubated with in the absence or presence of thrombin (10 nM) for 30 min at room temperature. Subsequently samples were analyzed via Western blotting using polyclonal sheep anti-FVIII antibodies. For samples incubated in the absence of thrombin, WT-FVIII-SQ is predominantly present in a cleaved form, consisting of a 90-kDa heavy chain and an 80-kDa light chain while some uncleaved material was also present (Lane 3 in FIG. 4). In contrast, for FVIII-KB013bv >90% of the preparation was present as a single-chain protein, appearing as a doublet (Lane 1 in FIG. 4). Of note, the size of the uncleaved FVIII-013bv is slightly larger than that of WT-FVIII-SQ, due to the insertion of two copies of sdAb KB-VWF-013 between the FVIII heavy and light chain (Lanes 1 & 3 in FIG. 4). In contrast, following incubation with thrombin, WT-FVIII-SQ and FVIII-013bv displayed a similar pattern for thrombin-activated FVIII, with a 70-kDa light chain and the separate A1 and A2 domains (Lanes 2 & 4 in FIG. 4). This analysis indicates that following thrombin activation, the inserted sdAb KB-VWF-013bv is removed from the protein, giving rise to the natural heterotrimeric FVIIIa protein.

Example G: In Vivo Survival of FVIII-KB-013bv

Purified WT-FVIII-SQ or FVIII-kb013bv (both produced in BHK-M cells and purified using VIIISelect-affinity chromatography) were given intravenously (250-500 U/kg) to FVIII-deficient mice. At different time-points after injection (3 min, 30 min, 1 h, 2 h, 8 h and 24 h for WT-FVIII-SQ and 3 min, 4 h, 9 h, 21 h, 29 h and 48 h for FVIII-KB013bv) blood samples were obtained via retro-orbital puncture from isoflurane-anesthetized mice and plasma was prepared by centrifugation (1500 g for 20 min at 22° C.). Residual FVIII activity was measured using a chromogenic two-stage assay as instructed by the manufacturer (Biophen FVIII:C; Hyphen Biomed, Neuville-sur-Oise, France). Residual FVIII activity relative to activity at 3 min after injection was plotted against the time after injection (FIG. 5). This approach revealed that activity for FVIII-KB013bv remained higher WT-FVIII-SQ at later time-points. For instance, relative residual FVIII activity for WT-FVIII at 24 h was 0.72±0.23% (n=3), whereas for FVIII-KB013bv the relative residual activity at 29 h was more than 3-fold higher (2.62±0.25%; n=3; p=0.0007 in student t-test). When data where analyzed using an equation describing a single exponential decay (Graph Prism 5 for Mac OSX, GraphPad Software, La Jolla, Calif., USA), the half-life calculated for WT-FVIII-SQ was 1.1 h (95% confidence interval 0.9-1.5 h). For FVIII-KB013bv the half-life was calculated to be 2.1 h (95% confidence interval 1.7-2.9 h; p=0.0032 compared to WT-FVIII-SQ), 2-fold longer than the half-life for WT-FVIII-SQ. These results show that the presence of two copies of sdAb KB-VWF-013 has a significant beneficial effect on the survival of FVIII.

Example H: Correction of Hemostasis in Hemophilic Mice 24 h after Injection of FVIII-KB013bv 8-12 week old hemophilic mice were given WT-FVIII-SQ (Xyntha) or FVIII-KB013bv at a dose of 500 U/kg via intravenous tail injection. Twenty-four hours after injection, the terminal 3 mm of the tail-tip was amputated from ketamine/xylazine-anesthetized mice. The amputated tail was immersed immediately after transaction in a 50 ml tube full of warm physiological saline. Blood was collected for 30 min at 37° C. After 30 min, the mixture of blood and physiological saline was centrifuged at 1500 g. The red blood cells pellet was then lysed in H2O and the amount of hemoglobin was obtained by reading the absorbance at 416 nm. The volume of blood lost in each sample was calculated from a standard curve, which is obtained by lysing defined volumes (20 µl, 40 µl, 60 µl, 80 µl and 100 µl) of mouse blood in H2O to extract hemoglobin as described above. Blood loss for each mouse is presented in FIG. 6. For mice injected with FVIII-KB013bv, average blood loss was calculated to be 13±3 µl (mean±standard deviation; n=3 mice). For mice that received WT-FVIII-SQ, average blood loss was 194±146 µl (mean±standard deviation; n=5 mice), which is significantly more compared the mice injected with FVIII-KB013bv (p=0.0043 as determined using the Mann-Whitney test). Thus, FVIII-KB013bv displays hemostatic activity for a longer period of time than does WT-FVIII-SQ.

Example I: Use of FVIII-KB013bv as a Therapeutic Protein to Reduce the Formation of Allo-Antibodies Although VWF and FVIII circulate in plasma as a complex, there is a striking difference in the extent by which allo-antibodies develop following therapeutic application of these proteins. Development of allo-antibodies to VWF in response to replacement therapy is estimated to involve 5-10% of the patients with severe von Willebrand disease (James et al (2013) *Blood vol* 122, pp 636-640). In contrast, inhibitory allo-antibodies arise in up to 27% of previously untreated haemophilia A patients (Iorio et al. (2010) *JTH vol* 8, pp 1256-1265).

The underlying reason for this difference in antibody development rate is unknown. Recently, it has been shown by Sorvillo and colleagues (Haematologica 2016 in press; doi:10.3324/haematol.2015.137067) that VWF remains associated at the surface of antigen-presenting cells without being endocytosed. In contrast, FVIII that was bound to this VWF is actually taken up by these cells and processed for incorporation into MHC-class II molecules, thereby allowing presentation to CD4+ T-cells. The notion that FVIII but not VWF enters into antigen-presenting cells could explain the antibody development is increased upon FVIII replacement therapy compared to VWF replacement therapy. A method that prevents dissociation of FVIII at the surface of the antigen presenting cell, and thereby uptake of FVIII by the antigen presenting cell would thus be a means to reduce the formation of allo-antibodies upon FVIII replacement therapy. One way to reduce dissociation of FVIII from VWF is by incorporating sdAbs against VWF in the FVIII protein, and an example hereof is FVIII-KB013bv of the present invention. FVIII-KB013bv could therefore be used as a therapeutic protein that is less immunogenic compared to FVIII that displays normal association-dissociation kinetics.

Example J: Fusion of KB-VWF-013 to Coagulation Factor VII Induces Complex Formation with VWF To determine whether sdAbs recognizing VWF can mediate binding of other proteins than FVIII to VWF, a cDNA was constructed encoding the sequence of human coagulation factor VII (FVII) fused to two copies of KB-VWF-013. Sequences encoding FVII and KB-VWF-013 were separated by a linker-sequence encoding a thrombin-cleavage site. The full sequence of this cDNA and corresponding protein is referred to as FVII-KB13-bv. FVII-KB-13-bv and WT-FVII were cloned into the pLIVE-plasmid (Mirus Bio, Madison, Wis., USA). Plasmids (100 µg/mouse) were injected into wild-type C57B16-mice via hydrodynamic gene transfer: plasmids are diluted in 0.9% saline with the volume corresponding to 10% of the animal's bodyweight (i.e. 2 ml for a 20-gram mouse). The solution is injected in the tail vein within 5 seconds. Four days after gene transfer, blood was collected via retro-orbital puncture from isoflurane-anesthetized mice and plasma was prepared by centrifugation (1500 g for 20 min at 22° C.). Plasma was then used to measure complexes between VWF and FVII or FVII-KB 13-bv that were formed in the plasma of the mice. Complexes were determined as follows: microtiter wells were coated with polyclonal sheep anti-human FVII antibodies (Affinity Biologicals, Ancaster ON, Canada) at a concentration of 2.5 µg/ml in 50 µl carbonate-buffer (0.07 M NaHCO3, 0.03 M Na2HCO3, pH 9.6) overnight at 4° C. Wells were washed thrice with Tris-buffered saline supplemented with 0.1% Tween-20 (TBS-T), then saturated with 5% BSA, 1% polyvinylpyrrolidone (PVP) in TBS-T for 2 hours at 37° C. and again washed 5 times with TBS-T. Then murine plasma samples (diluted 10-fold in 50 µl TBS-T containing 1% BSA) were added to the wells and incubated 2 hours at 37° C. After 5 washes with TBS-T (75 µl/well), bound FVII or FVII-KB13-bv was probed using peroxidase-labeled polyclonal rabbit anti-VWF antibodies (Dako) and detected by measuring peroxidase-mediated hydrolysis of 3,3',5,5'-tetramethylbenzidine. Whereas for mice expressing FVII no signal above the background could be detected (OD450 nm=−0.038±0.033; mean±standard deviation; n=4 mice), suggesting the absence of complexes between VWF and FVII. In contrast, a clear signal was observed for plasma from each mouse expressing FVII-KB13-bv (OD450 nm=0.684±0.554; n=4; p=0.029 analyzed using Mann-Whitney test). This demonstrates that the fusion of FVII to sdAb KB-VWF-013 induces the protein to associate to circulating VWF.

REFERENCES

Throughout this application, various references describe the state of the art to which this invention pertains. The disclosures of these references are hereby incorporated by reference into the present disclosure.

1. Mei B, Pan C, Jiang H, et al. Rational design of a fully active, long-acting PEGylated factor VIII for hemophilia A treatment. Blood 2010; 116(2):270-279.
2. Dumont J A, Liu T, Low S C, et al. Prolonged activity of a recombinant factor VIII-Fc fusion protein in hemophilia A mice and dogs. Blood 2012; 119(13):3024-3030.
3. Yee A, Gildersleeve R D, Gu S, et al. A von Willebrand factor fragment containing the D'D3 domains is sufficient to stabilize coagulation factor VIII in mice. Blood 2014; 124(3):445-452.

The invention claimed is:

1. A chimeric polypeptide comprising a polypeptide and at least one sdAb directed against von Willebrand Factor (VFW) D'D3 domain, wherein the polypeptide encodes a clotting factor, and wherein said sdAb comprises:

i) a CDR1 having a sequence set forth as SEQ ID NO: 1, a CDR2 having a sequence set forth as SEQ ID NO: 2 and a CDR3 having a sequence set forth as SEQ ID NO: 3;

ii) a CDR1 having a sequence set forth as SEQ ID NO: 5, a CDR2 having a sequence set forth as SEQ ID NO: 6 and a CDR3 having a sequence set forth as SEQ ID NO: 7; and/or iii) a CDR1 having a sequence set forth as SEQ ID NO: 9, a CDR2 having a sequence set forth as SEQ ID NO: 10 and a CDR3 having a sequence set forth as SEQ ID NO: 11.

2. An isolated single-domain antibody (sdAb) directed against von Willebrand Factor (VWF) D'D3 domain, wherein said sdAb comprises a CDR1 having a sequence set forth as SEQ ID NO: 1, a CDR2 having a sequence set forth as SEQ ID NO: 2 and a CDR3 having a sequence set forth as SEQ ID NO: 3; wherein the sdAb is fused with a clotting factor.

3. The chimeric polypeptide according to claim 1, wherein said chimeric polypeptide has an increased affinity and/or a reduced dissociation rate constant for VWF compared to a wild-type polypeptide encoding the clotting factor.

4. The chimeric polypeptide according to claim 1, wherein the clotting factor selected from the group consisting of FVII, FVIII, protein C and protein S.

5. The chimeric polypeptide according to claim 1, wherein said at least one single-domain antibody is fused at the N terminal end, at the C terminal end, both at the N terminal end and at the C terminal end of the chimeric polypeptide or is inserted within the sequence of the chimeric polypeptide.

6. The chimeric polypeptide according to claim 1, comprising two, three, four, or five sdAb directed against VWF.

7. The chimeric polypeptide according to claim 1, wherein the chimeric polypeptide comprises two sdAb directed against VWF which:
  i) replace the C-terminal part of the B domain of factor VIII (FVIII-KB13-bv, KB-VWF-008 and/or KB-VWF-011);
  ii) are fused to the C-terminus of FVIII;
  iii) simultaneously replace the C-terminal part of the B domain of factor VIII and are fused to C-terminus of factor VIII; or
  iv) are inserted at the C-terminus of factor VII.

8. The chimeric polypeptide according to claim 1, wherein the polypeptide comprises at least one single-domain antibody directed against a first antigen and at least one further binding site directed against a second antigen.

9. A chimeric polypeptide/VWF complex comprising the chimeric polypeptide of claim 1 and a VWF polypeptide, wherein the VWF polypeptide has an extended half-life within the chimeric polypeptide/VWF complex.

10. A pharmaceutical composition comprising a chimeric polypeptide according to claim 1 or a chimeric polypeptide/VWF according to claim 9, complex comprising the chimeric polypeptide, and a pharmaceutically acceptable carrier.

* * * * *